(12) United States Patent
Vandyck et al.

(10) Patent No.: US 9,233,933 B2
(45) Date of Patent: Jan. 12, 2016

(54) 4,4-DISUBSTITUTED-1,4-DIHYDROPYRIMIDINES AND THE USE THEREOF AS MEDICAMENTS FOR THE TREATMENT OF HEPATITIS B

(71) Applicant: Janssen R&D Ireland, Co. Cork (IE)

(72) Inventors: Koen Vandyck, Paal-Beringen (BE); Geerwin Yvonne Paul Haché, Kapellen (BE); Geert Rombouts, Borsbeek (BE); Wim Gaston Verschueren, Berchem (BE); Pierre Jean-Marie Raboisson, Rosieres (BE)

(73) Assignee: Janssen Sciences Ireland UC, Little Island, Co. Cork (IE)

( * ) Notice: Subject to any disclaimer, the term of this patent is extended or adjusted under 35 U.S.C. 154(b) by 0 days.

(21) Appl. No.: 14/370,118

(22) PCT Filed: Jan. 4, 2013

(86) PCT No.: PCT/EP2013/050095
§ 371 (c)(1),
(2) Date: Jul. 1, 2014

(87) PCT Pub. No.: WO2013/102655
PCT Pub. Date: Jul. 11, 2013

(65) Prior Publication Data
US 2015/0005295 A1    Jan. 1, 2015

(30) Foreign Application Priority Data

Jan. 6, 2012 (EP) .................................. 12150384
May 8, 2012 (EP) .................................. 12167065

(51) Int. Cl.
| | |
|---|---|
| A61K 31/541 | (2006.01) |
| C07D 239/22 | (2006.01) |
| C07D 401/04 | (2006.01) |
| C07D 403/04 | (2006.01) |
| C07D 417/04 | (2006.01) |
| C07D 471/10 | (2006.01) |
| C07D 491/107 | (2006.01) |
| A61K 31/505 | (2006.01) |
| A61K 31/506 | (2006.01) |
| A61K 31/513 | (2006.01) |
| A61K 31/527 | (2006.01) |
| A61K 31/5377 | (2006.01) |
| A61K 45/06 | (2006.01) |
| C07D 487/10 | (2006.01) |

(52) U.S. Cl.
CPC ............ *C07D 239/22* (2013.01); *A61K 31/505* (2013.01); *A61K 31/506* (2013.01); *A61K 31/513* (2013.01); *A61K 31/527* (2013.01); *A61K 31/5377* (2013.01); *A61K 31/541* (2013.01); *A61K 45/06* (2013.01); *C07D 401/04* (2013.01); *C07D 403/04* (2013.01); *C07D 417/04* (2013.01); *C07D 471/10* (2013.01); *C07D 487/10* (2013.01); *C07D 491/107* (2013.01)

(58) Field of Classification Search
CPC .. C07D 239/20; C07D 239/22; C07D 401/04; C07D 413/06; C07D 403/04; C07D 417/04; C07D 471/10; C07D 491/107; C07D 487/10; A61K 31/506; A61K 31/527; A61K 31/5377; A61K 31/513; A61K 31/505; A61K 45/06; A61K 31/541
See application file for complete search history.

(56) References Cited

U.S. PATENT DOCUMENTS

| | | |
|---|---|---|
| 6,503,913 B1 | 1/2003 | Goldman |
| 7,074,784 B2 | 7/2006 | Goldman |
| 8,343,969 B2 | 1/2013 | Goldman |

FOREIGN PATENT DOCUMENTS

| | | |
|---|---|---|
| CN | 1297449 A | 5/2001 |
| DE | 19962010 A1 | 6/2001 |
| JP | 50137987 A  * | 11/1975 |
| WO | WO 00/58302 A1 | 10/2000 |
| WO | 0145712 A1 | 6/2001 |

(Continued)

OTHER PUBLICATIONS

H. Sheibani et al., 7 Journal of Chemical Research, 390-392 (2008).*
K. Joshi et al., 31B Indian Journal of Chemistry, Section B: Organic Chemistry Including Medicinal Chemistry, 280-281 (1992).*
Weber et al., "Inhibition of human hepatitis B virus (HBV) by a novel non-nucleosidic compound in a transgenic mouse model", *Antiviral Research*. 54: 69-78 (2002).
Deres et al., "Inhibition of Hepatitis B Virus Replication by Drug-Induced Depletion of Nucelocapsids", *Science* 299: 893-896 (2003).
Lehnert, Willy, "Verbesserte Variante Der Knoevenagel-Kondensation MIT Ticl₄/THF/Pyridin(I)", *Tetrahedron Letters* No. 54, pp. 4723-4724 (1970).

(Continued)

Primary Examiner — Alexander R Pagano
(74) Attorney, Agent, or Firm — Andrea Jo Kamage

(57) ABSTRACT

Inhibitors of HBV replication of formula (I) including stereochemically isomeric forms, and salts, hydrates, solvates thereof, wherein $R_1$-$R_5$, B and Z have the meaning as defined herein. The present invention also relates to processes for preparing said compounds, pharmaceutical compositions containing them and their use, alone or in combination with other HBV inhibitors, in HBV therapy.

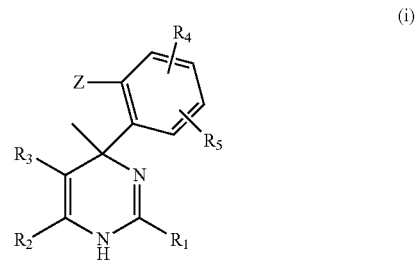

13 Claims, No Drawings

(56) References Cited

FOREIGN PATENT DOCUMENTS

| WO | WO 01/68642 A1 | 9/2001 |
|---|---|---|
| WO | 2008154817 A1 | 12/2008 |
| WO | 2010069147 A1 | 6/2010 |
| WO | WO 2010/069147 A1 | 6/2010 |

OTHER PUBLICATIONS

Hormi, Osmo, "Utilization of β-Chloro Alkylidene/Arylidene Malonates in Organic Systhesis:Ethyl Cyclopropylpropiolate ", *Organic Syntheses, Coll.* Vol. 8, p. 247 (1993).

Hormi, Osmo, "Utilization of β-Chloro Alkylidene/Arylidene Malonates in Organic Synthesis: Synthsis of Ethyl Cyclopropylpropiolate ", *Organic Syntheses*, Coll. vol. 8, vol. 66, p. 173-179 (1988).

Poondra et al., "Efficient Palladium-Catalyzed Cross-Coupling of βChloroalkylidene/arylidene Malonates Using Microwave Chemistry", *Journal of Organic Chemistry*, 69, 20, 6920-6922 (2004).

Zhang et al., "Indiium (III) mediated Markovnikov addition of malonates and β-ketoesters to terminal alkynes and the formation of Knoevenagal condensation procducts", *Tetrahedron*, 61, 32, 7807-7813 (2005).

Khorshidi et al., "Novel One-Pot Synthesis of New Oxindole Derivatives Catalyzed by PTSA", *Synthetic Communications*, 41(19), 2899-2904 (2011).

Jones, G., "The Knoevenagel Condensation", Organic Reactions, Chapter 2, pp. 204-591 (2011).

Nishimura et al., Chem Pharm Bull, vol. 59, No. 12, pp. 1458-1466 (2011).

Cho, H. et al., "Synthesis and substation reactions of 4(6)0chloro-dihydropyrimidines", Heterocycles, vol. 83, No. 8, pp. 1807-1818 (2011).

\* cited by examiner

4,4-DISUBSTITUTED-1,4-DIHYDROPYRIMIDINES AND THE USE THEREOF AS MEDICAMENTS FOR THE TREATMENT OF HEPATITIS B

CROSS-REFERENCE TO RELATED APPLICATIONS

This application is a 371 national stage entry of International Application Number PCT/EP2013/050095, filed 4 Jan. 2013, which claims the benefit of Application Number EP12150384.1, filed 6 Jan. 2012 and EP12167065.7, filed 8 May 2012. The entire contents of each of the aforesaid applications are incorporated herein by reference in their entirety.

TECHNICAL FIELD 4,4-disubstituted-1,4-dihydropyrimidines and the use thereof as medicaments for the treatment of hepatitis B.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China.

HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine. Interferon is expensive and frequently not well tolerated, and nucleosides have been shown to select for resistant mutants.

Drug screens have identified heteroaryldihydropyrimidines (HAPs) as a class of HBV inhibitors in tissue culture and animal models, effective at nanomolar concentrations (Weber et al., Antiviral Res. 54: 69-78). Further research has shown that HAPs target Cp (Deres et al., Science 299: 893-896), causing the inappropriate assembly of capsid at higher drug concentrations.

A number of patents and patent applications disclose compounds with HBV inhibitory activity, in particular dihydropyrimidine derivatives, including WO00/058302, WO01/68642 and WO2010/069147.

Amongst the problems which HBV direct antivirals may encounter are toxicity, mutagenicity, lack of selectivity, poor efficacy, poor bioavailability, racemisation of chiral centers and difficulty of synthesis.

There is a need for HBV inhibitors that may overcome at least one of these disadvantages.

DESCRIPTION OF THE INVENTION

In one aspect, the present invention provides compounds, which can be represented by the formula I:

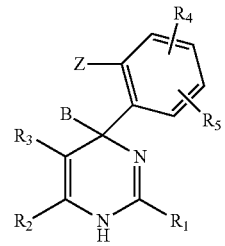

(I)

including any possible stereoisomers or tautomeric forms thereof, wherein:

B is selected from the group comprising $C_1$-$C_3$ alkyl optionally substituted with one or more Fluoro atoms;

Z is selected from H or halogen;

Or B and Z together with the carbons to which they are attached form a 4-7 membered ring, optionally containing one or more heteroatoms, wherein the 4-7 membered ring optionally is substituted with one or more substituents selected from the group comprising $C_1$-$C_3$ alkyl, oxo, OH and halogen;

$R_1$ is selected from the group comprising heteroaryl and phenyl, optionally substituted with one or more substituents selected from the group comprising halogen and $C_1$-$C_3$ alkyl;

$R_2$ is selected from the group comprising —$R_6$-$R_7$, C≡N, cyclopropyl, and $CF_3$;

$R_3$ is selected from the group comprising $C_1$-$C_3$alkoxycarbonyl, and C≡N;

$R_4$ and $R_5$ independently are selected from the group comprising H, methyl and halogen;

$R_6$ is $C_1$-$C_3$ alkyl, $C_2$-$C_3$alkenyl, both optionally substituted with one or more Fluoro;

$R_7$ is selected from the group comprising hydrogen, a hetero $C_{3-7}$cycloalkyl, cyclopropyl, $C_1$-$C_3$alkoxy and $CF_3$;

or a pharmaceutically acceptable salt or a solvate thereof.

In one embodiment,

B is selected from the group comprising $C_1$-$C_3$ alkyl optionally substituted with one or more Fluoro atoms;

Z is selected from H or halogen;

Or B and Z together with the carbons to which they are attached form a 4-7 membered ring, optionally containing one or more heteroatoms, wherein the 4-7 membered ring optionally is substituted with one or more substituents selected from the group comprising $C_1$-$C_3$ alkyl, oxo and halogen;

$R_1$ is selected from the group comprising heteroaryl and phenyl, optionally substituted with one or more substituents selected from the group comprising halogen and $C_1$-$C_3$ alkyl;

$R_2$ is selected from the group comprising —$R_6$-$R_7$, C≡N, cyclopropyl, and $CF_3$;

$R_3$ is selected from the group comprising $C_1$-$C_3$alkoxycarbonyl, and C≡N;

$R_4$ and $R_5$ independently are selected from the group comprising H and halogen;

$R_6$ is $C_1$-$C_3$ alkyl, optionally substituted with Fluoro;

And $R_7$ is selected from the group comprising hydrogen, a hetero $C_{3-7}$cycloalkyl, cyclopropyl and $CF_3$;

In a particular group of compounds of Formula I according to the invention, B is selected from the group comprising $C_1$-$C_3$ alkyl optionally substituted with one or more Fluoro atoms; Z is selected from H or halogen;

Or B and Z together with the carbons to which they are attached form a 4-7 membered ring, optionally containing one or more heteroatoms, wherein the 4-7 membered ring optionally is substituted with one or more substituents selected from the group comprising $C_1$-$C_3$ alkyl;

$R_1$ is selected from the group comprising heteroaryl and phenyl, optionally substituted with 1 or more halogen atoms;

The invention further relates to a pharmaceutical composition comprising a compound of Formula I, and a pharmaceutically acceptable carrier.

The invention also relates to the compounds of formula I for use as a medicament, preferably for use in the prevention or treatment of an HBV infection in a mammal.

In a further aspect, the invention relates to a combination of a compound of formula I, and another HBV inhibitor.

In yet another aspect, the invention relates to a compound according to formula V

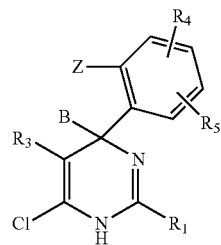

wherein B, Z, $R_1$, $R_3$, $R_4$, and $R_5$ are defined as above.

The invention further relates to the use of a compound of formula V in the synthesis of a compound according to formula I.

DEFINITIONS

The term "$C_{1-3}$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

The term "$C_{2-4}$alkenyl" as a group or part of a group defines straight and branched chained saturated hydrocarbon radicals having from 2 to 4 carbon atoms containing at least one double bond such as, for example, vinyl, propenyl, butenyl, and the like.

The term "$C_{1-3}$alkyloxy" or $C_{1-3}$alkoxy as a group or part of a group refers to a radical having the Formula —OR' wherein $R^c$ is $C_{1-3}$alkyl. Non-limiting examples of suitable $C_{1-3}$alkyloxy include methyloxy (also methoxy), ethyloxy (also ethoxy), propyloxy and isopropyloxy.

As used herein, the term carbonyl, or "(=O)" or "oxo" forms a carbonyl moiety when attached to a carbon atom. It should be noted that an atom can only be substituted with an oxo group when the valency of that atom so permits.

As used herein, the term "hetero $C_{3-7}$cycloalkyl" means saturated cyclic hydrocarbon group as defined for "hetero $C_{3-7}$cycloalkyl" wherein at least one carbon atom is replaced by a heteroatom selected from N, O and S, in particular from N and O. Examples of hetero $C_{3-7}$cycloalkyl include tetrahydro-2H-pyranyl, piperidinyl, tetrahydrofuranyl, morpholinyl and pyrrolidinyl.

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. For the purposes of the invention, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "($C_2$-$C_5$)heteroaryl".

It should be noted that different isomers of the various heterocycles may exist within the definitions as used throughout the specification. For example, pyrrolyl may be 1H-pyrrolyl or 2H-pyrrolyl.

The term halo is generic to fluoro, chloro, bromo or iodo.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

The term "B and Z together with the carbons to which they are attached form a 4-7 membered ring" indicates that B and Z together form a bridge consisting of 1, 2, 3 or 4 atoms. B and Z may together represent one atom. B and Z may be coupled via a direct saturated or unsaturated bond, or B and Z may be coupled via 1 or 2 additional atoms via saturated or unsaturated bonds. Graphically, this is represented below by the following structural formulas (I)4, (I)5, (I)6 and (I)7, wherein $R_1$-$R_5$ have the meaning as defined in the present application and X, B and Z represent a carbon or heteroatom, preferably carbon or oxygen:

For a 4 membered ring:

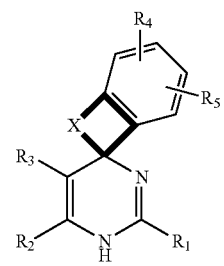

(I)4

For a 5 membered ring:

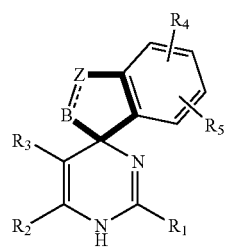

(I)5

For a 6 membered ring:

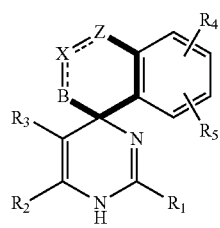

And for a 7 membered ring:

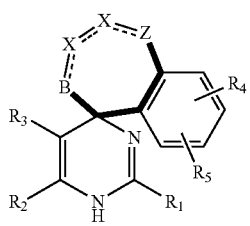

When any variable (e.g. halogen or $C_{1-4}$alkyl) occurs more than one time in any constituent, each definition is independent.

For therapeutic use, the salts of the compounds of formula (I) are those wherein the counter ion is pharmaceutically or physiologically acceptable. However, salts having a pharmaceutically unacceptable counter ion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

DETAILED DESCRIPTION OF THE INVENTION

Whenever used hereinafter, the term "compounds of formula (I)",

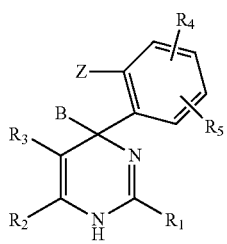

or "the present compounds" or similar term is meant to include the compounds of general formula (I), salts, stereoisomeric forms and racemic mixtures or any subgroups thereof.

The present invention provides compounds, which can be represented by formula I:

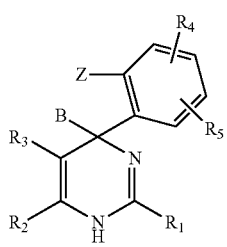

including any possible stereoisomers or tautomeric forms thereof, wherein:
B is selected from the group comprising $C_1$-$C_3$ alkyl optionally substituted with one or more Fluoro atoms;
Z is selected from H or halogen;
Or B and Z together with the carbons to which they are attached form a 4-7 membered ring, optionally containing one or more heteroatoms, wherein the 4-7 membered ring optionally is substituted with one or more substituents selected from the group comprising $C_1$-$C_3$ alkyl, oxo, OH and halogen;
$R_1$ is selected from the group comprising heteroaryl and phenyl, optionally substituted with one or more substituents selected from the group comprising halogen and $C_1$-$C_3$ alkyl;
$R_2$ is selected from the group comprising —$R_6$-$R_7$, C≡N, cyclopropyl, and $CF_3$;
$R_3$ is selected from the group comprising $C_1$-$C_3$alkoxycarbonyl, and C≡N;
$R_4$ and $R_5$ independently are selected from the group comprising H, methyl and halogen;
$R_6$ is $C_1$-$C_3$ alkyl, $C_2$-$C_3$alkenyl, both optionally substituted with one or more Fluor;
$R_7$ is selected from the group comprising hydrogen, a hetero $C_{3-7}$cycloalkyl, cyclopropyl, $C_1$-$C_3$alkoxy and $CF_3$;
or a pharmaceutically acceptable salt or a solvate thereof.

An interesting subgroup of compounds according to the invention are compounds of formula (I),
including any possible stereoisomers or tautomeric forms thereof, wherein:
B is selected from the group comprising $C_1$-$C_3$ alkyl optionally substituted with one or more Fluoro atoms;
Z is selected from H or halogen;
Or B and Z together with the carbons to which they are attached form a 4-7 membered ring, optionally containing one or more heteroatoms, wherein the 4-7 membered ring optionally is substituted with one or more substituents selected from the group comprising $C_1$-$C_3$ alkyl;
$R_1$ is selected from the group comprising heteroaryl and phenyl, optionally substituted with 1 or more halogen atoms;
$R_2$ is selected from the group comprising —$R_6$-$R_7$, C≡N, cyclopropyl, and $CF_3$;
$R_3$ is selected from the group comprising $C_1$-$C_3$alkoxycarbonyl, and C≡N;
$R_4$ and $R_5$ independently are selected from the group comprising H and halogen;
$R_6$ is $C_1$-$C_3$ alkyl, optionally substituted with Fluoro;
$R_7$ is selected from the group comprising hydrogen, a hetero $C_{3-7}$cycloalkyl, cyclopropyl and $CF_3$;

Another interesting subgroup of the compounds of formula (I) are those compounds of formula (I) where:
B and Z together with the carbons to which they are attached form a 5- or 6-membered ring, optionally containing one or more heteroatoms, wherein the 5- or 6-membered ring optionally is substituted with one or more substituents selected from the group comprising $C_1$-$C_3$ alkyl, oxo and halogen;
$R_1$ is heteroaryl, optionally substituted with 1 or more halogen atoms;
$R_2$ is selected from the group comprising —$R_6$-$R_7$, C≡N, cyclopropyl, and $CF_3$;
$R_3$ is selected from the group comprising $C_1$-$C_3$alkoxycarbonyl, and C≡N;
$R_4$ and $R_5$ independently are selected from the group comprising H and halogen;
$R_6$ is $C_1$-$C_3$ alkyl, optionally substituted with Fluoro;
$R_7$ is selected from the group comprising hydrogen, a hetero $C_{3-7}$cycloalkyl or $CF_3$;

In an embodiment of this subgroup, B and Z together with the carbons to which they are attached form a 5-6 membered ring, optionally containing one or more heteroatoms, wherein the 5-6 membered ring optionally is substituted with one or more substituents selected from the group comprising $C_1$-$C_3$ alkyl.

A particular group of compounds are those compounds of formula (I) wherein the heteroaryl of $R_1$ comprises a nitrogen atom adjacent to the carbon attached to the 4,4-disubstituted-1,4-dihydropyrimidine (e.g. $R_1$ is 2-pyridinyl or 2-thiazolyl).

Another particular group of compounds are those compounds of formula (I) wherein —$R_6$-$R_7$ represents Methyl.

An interesting subgroup of the compounds of formula (I) are those compounds of formula (I) or subgroups thereof wherein any combination of the following restrictions applies:
B and Z together with the carbons to which they are attached form a 5 or 6 membered ring, optionally substituted with one or more $CH_3$ or Fluoro substituents;
$R_1$ is selected from pyridinyl or thiazolyl;
$R_2$ is selected from the group comprising —$R_6$-$R_7$, C≡N, cyclopropyl, and $CF_3$;
$R_3$ is $C_1$- or $C_2$-alkyloxycarbonyl, preferably $C_1$-alkyloxycarbonyl;
$R_6$ is $CH_2$
$R_7$ is selected from hydrogen, morpholinyl or piperidinyl;
$R_4$ and $R_5$ independently are selected from the group H and Fluoro.

A preferred subgroup of the present invention is a compound according to formula Ia

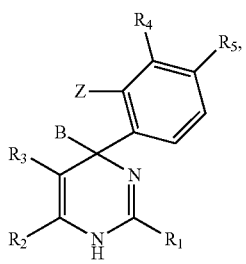
(Ia)

including any possible stereoisomers or tautomeric forms thereof, wherein:

B is selected from the group comprising $C_1$-$C_3$ alkyl optionally substituted with one or more Fluoro atoms;

Z is selected from H or halogen;

Or B and Z together with the carbons to which they are attached form a 4-7 membered ring, optionally containing one or more heteroatoms, wherein the 4-7 membered ring optionally is substituted with one or more substituents selected from the group comprising $C_1$-$C_3$ alkyl, oxo and halogen;

$R_1$ is selected from the group comprising heteroaryl and phenyl, optionally substituted with one or more substituents selected from the group comprising halogen and $C_1$-$C_3$ alkyl;

$R_2$ is selected from the group comprising —$R_6$-$R_7$, cyclopropyl, and $CF_3$;

$R_3$ is selected from the group comprising $C_1$-$C_3$alkoxycarbonyl, and C≡N;

$R_4$ and $R_5$ independently are selected from the group comprising H and halogen;

$R_6$ is $C_1$-$C_3$ alkyl, optionally substituted with Fluoro;

$R_7$ is selected from the group comprising hydrogen, a hetero $C_{3-7}$cycloalkyl, cyclopropyl and $CF_3$;

or a pharmaceutically acceptable salt or a solvate thereof.

An interesting subgroup of compounds according to the invention are compounds of formula (Ia), including any possible stereoisomers or tautomeric forms thereof, wherein:

B is selected from the group comprising $C_1$-$C_3$ alkyl optionally substituted with one or more Fluoro atoms;

Z is selected from H or halogen;

Or B and Z together with the carbons to which they are attached form a 4-7 membered ring, optionally containing one or more heteroatoms, wherein the 4-7 membered ring optionally is substituted with one or more substituents selected from the group comprising $C_1$-$C_3$ alkyl;

$R_1$ is selected from the group comprising heteroaryl and phenyl, optionally substituted with 1 or more halogen atoms;

$R_2$ is selected from the group comprising —$R_6$-$R_7$, C≡N, cyclopropyl, and $CF_3$;

$R_3$ is selected from the group comprising $C_1$-$C_3$alkoxycarbonyl, and C≡N;

$R_4$ and $R_5$ independently are selected from the group comprising H and halogen;

$R_6$ is $C_1$-$C_3$ alkyl, optionally substituted with Fluoro;

$R_7$ is selected from the group comprising hydrogen, a hetero $C_{3-7}$cycloalkyl, cyclopropyl and $CF_3$;

or a pharmaceutically acceptable salt or a solvate thereof.

An interesting subgroup of the compounds of formula (Ia) are those compounds of formula (Ia) where:

B and Z together with the carbons to which they are attached form a 5- or 6-membered ring, optionally containing one or more heteroatoms, wherein the 5- or 6-membered ring optionally is substituted with one or more substituents selected from the group comprising $C_1$-$C_3$ alkyl, oxo and halogen;

$R_1$ is heteroaryl, optionally substituted with 1 or more halogen atoms;

$R_2$ is selected from the group comprising —$R_6$-$R_7$, C≡N and $CF_3$;

$R_3$ is selected from the group comprising $C_1$-$C_3$alkoxycarbonyl, and C≡N;

$R_4$ and $R_5$ independently are selected from the group comprising H and halogen;

$R_6$ is $C_1$-$C_3$ alkyl, optionally substituted with Fluoro;

$R_7$ is selected from the group comprising hydrogen, a hetero $C_{3-7}$cycloalkyl or $CF_3$;

In an embodiment of this subgroup, B and Z together with the carbons to which they are attached form a 5-6 membered ring, optionally containing one or more heteroatoms, wherein the 5-6 membered ring optionally is substituted with one or more substituents selected from the group comprising $C_1$-$C_3$ alkyl.

A particular group of compounds are those compounds of formula (Ia) wherein the heteroaryl of $R_1$ comprises a nitrogen atom adjacent to the carbon attached to the 4,4-disubstituted-1,4-dihydropyrimidine (e.g. $R_1$ is 2-pyridinyl or 2-thiazolyl)

Another particular group of compounds are those compounds of formula (Ia) wherein —$R_6$-$R_7$ represents Methyl.

An interesting subgroup of the compounds of formula (Ia) are those compounds of formula (Ia) or subgroups thereof wherein any combination of the following restrictions applies:

B and Z together with the carbons to which they are attached form a 5 or 6 membered ring, optionally substituted with one or more $CH_3$ or Fluoro substituents;

$R_1$ is selected from pyridinyl or thiazolyl;

$R_2$ is selected from the group comprising —$R_6$-$R_7$, C≡N, cyclopropyl, and $CF_3$;

$R_3$ is $C_1$- or $C_2$-alkyloxycarbonyl, preferably $C_1$-alkyloxycarbonyl;

$R_6$ is $CH_2$ $R_7$ is selected from hydrogen, morpholinyl or piperidinyl;

$R_4$ and $R_5$ independently are selected from the group H and Fluoro.

Most preferred are the compounds as shown in table 1.

In a further aspect, the present invention concerns a pharmaceutical composition comprising a therapeutically or prophylactically effective amount of a compound of formula I as specified herein, including the additional compounds of Formula (I) wherein $R_1$ is S-Methyl, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of formula I, including the additional compounds of Formula (I) wherein $R_1$ is S-Methyl, as specified herein.

Therefore, the compounds of the present invention, including the additional compounds of Formula (I) wherein $R_1$ is S-Methyl, or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I, including the additional compounds of Formula (I) wherein $R_1$ is S-Methyl, are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of formula I, including the additional compounds of Formula (I) wherein $R_1$ is S-Methyl, or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of formula I including the additional compounds of Formula (I) wherein $R_1$ is S-Methyl.

The compounds of formula I, as specified herein, including the additional compounds of Formula (I) wherein $R_1$ is S-Methyl, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of formula (I), including the additional compounds of Formula (I) wherein $R_1$ is S-Methyl, or any subgroup thereof, as specified herein with other anti-HBV agents. The term "combination" may relate to a product or kit containing (a) a compound of formula I, including the additional compounds of Formula (I) wherein $R_1$ is S-Methyl, as specified above, and (b) at least one other compound capable of treating HBV infection (herein designated as anti-HBV agent), as a combined preparation for simultaneous, separate or sequential use in treatment of HBV infections.

In an embodiment, the invention concerns combination of a compound of formula (I), including the additional compounds of Formula (I) wherein $R_1$ is S-Methyl or any subgroup thereof with at least one anti-HBV agent. In a particular embodiment, the invention concerns combination of a compound of formula (I), including the additional compounds of Formula (I) wherein $R_1$ is S-Methyl or any subgroup thereof with at least two anti-HBV agents. In a particular embodiment, the invention concerns combination of a compound of formula (I), including the additional compounds of Formula (I) wherein $R_1$ is S-Methyl, or any subgroup thereof with at least three anti-HBV agents. In a particular embodiment, the invention concerns combination of a compound of formula (I), including the additional compounds of Formula (I) wherein $R_1$ is S-Methyl, or any subgroup thereof with at least four anti-HBV agents.

The combination of previously known anti-HBV agents, such as interferon-α (IFN-α), pegylated interferon-α, 3TC, adefovir or a combination thereof, and, a compound of formula (I) or any subgroup thereof can be used as a medicine in a combination therapy.

In a further aspect, the invention relates to a compound according to formula V

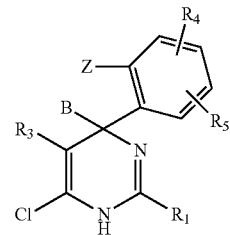

(V)

wherein $R_1$, $R_3$, $R_4$, and $R_5$ are defined as above for Formula I and Ia.

The invention further relates to the use of a compound of formula V in the synthesis of a compound according to formula I. The general synthesis is shown in Scheme 1 below. Examples of suitable reaction conditions are shown in the general synthetic methods part and in more detail in the experimental section.

An interesting subgroup of the compounds of formula (V) are those compounds of formula (V) where:

B and Z together with the carbons to which they are attached form a 5- or 6-membered ring, optionally containing one or more heteroatoms, wherein the 5- or 6-membered ring optionally is substituted with one or more substituents selected from the group comprising $C_1$-$C_3$ alkyl;

$R_1$ is heteroaryl, optionally substituted with 1 or more halogen atoms;

$R_2$ is selected from the group comprising —$R_6$-$R_7$, C≡N and $CF_3$;

$R_3$ is selected from the group comprising $C_1$-$C_3$alkoxycarbonyl, and C≡N;

$R_4$ and $R_5$ independently are selected from the group comprising H and halogen;

$R_6$ is $C_1$-$C_3$ alkyl, optionally substituted with Fluoro;

$R_7$ is selected from the group comprising hydrogen, a hetero $C_{3-7}$cycloalkyl or $CF_3$;

A particular group of compounds are those compounds of formula (V) wherein the heteroaryl of $R_1$ comprises a nitrogen atom adjacent to the carbon attached to the 4,4-disubstituted-1,4-dihydropyrimidine (e.g. $R_1$ is 2-pyridinyl or 2-thiazolyl)

An interesting subgroup of the compounds of formula (V) are those compounds of formula (V) or subgroups thereof wherein any combination of the following restrictions applies:

B and Z together with the carbons to which they are attached form a 5- or 6-membered ring, optionally. substituted with one or more $CH_3$ substituents;

$R_1$ is selected from pyridinyl or thiazolyl;

$R_3$ is $C_1$- or $C_2$-alkyloxycarbonyl, preferably $C_1$-alkyloxycarbonyl;

$R_6$ is $CH_2$ $R_7$ is selected from hydrogen, morpholinyl or piperidinyl;

$R_4$ and $R_5$ independently are selected from the group H and Fluoro.

General Synthetic Methods

A possible synthesis of a compound of formula I is described in Scheme 1.

A compound of general formula II is reacted with an amidine compound of general formula III, possibly in the presence of a base (for example $Na_2CO_3$, KOtBu or $NaHCO_3$) resulting in a cyclic compound of general formula IV. This compound of general formula IV can be chlorinated to a compound of general formula V, for example by heating in $POCl_3$. The compound of general formula V can then be transformed to compounds of general formula I, for example by a Suzuki type coupling in case $R_2$ equals —$CH_2$-Het, wherein het represents a hetero-$C_{3-7}$cycloalkyl or cyclopropyl; a Stille type coupling in case $R_2$ equals Me; a substitution in case $R_2$ equals CN or as exemplified in the experimental section. Alternatively one of the two amidine-nitrogens in compound V can be protected with for example a Boc-group, after which for example a Suzuki or Stille coupling can be performed, followed by deprotection of the nitrogen, resulting in compound I.

Scheme 1:

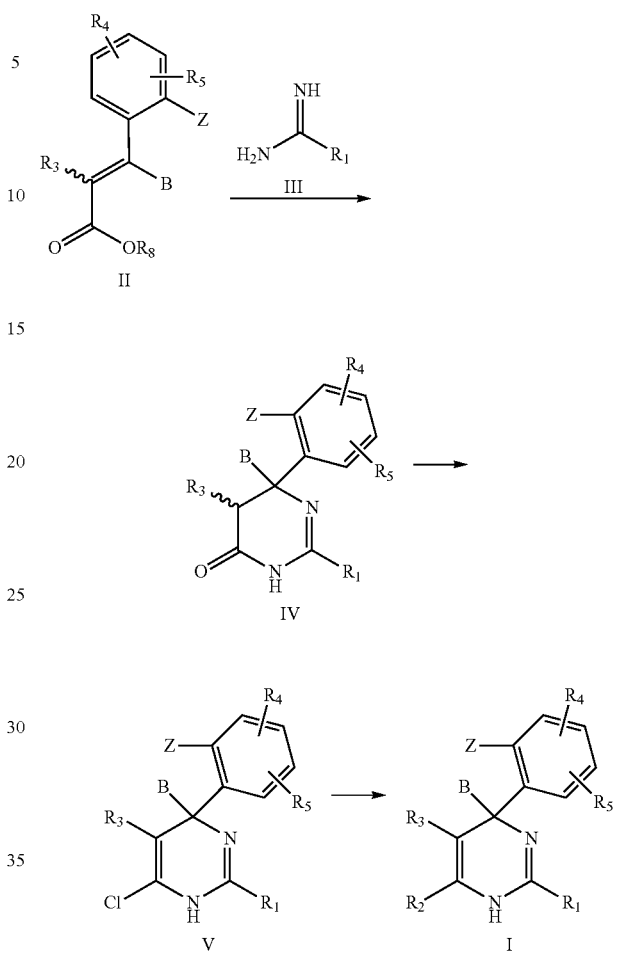

Compound of general formula II can be synthesized as described in Scheme 2 (a, b, c, d), the conditions used are depending on the substituents Z, B and $R_3$ on compound of general formula II. $R_8$ represents $C_1$-$C_3$alkyl, preferably methyl or ethyl.

A possible method is described in Scheme 2a for the synthesis of compound with general formula IIa. In case B equals $C_{1-3}$alkyl or $CF_3$, or B and Z are connected so that the compound of general formula VI is a indan-1-one derivative, Lehnnert conditions ($TiCl_4$/pyridine, for example described in Tetrahedron Letters No. 34, pp. 4723-4724, 1970 or modifications hereof) can be used for the knoevenagel condensation of VI and VII. Alternatively, in case B equals $C_{1-3}$alkyl, compound of general formula IIb can be synthesized as described in Scheme 2b, via a Suzuki type reaction of a boronic acid (or other boron derivative) of general formula IX and a vinylic chloride of general formula VIII (prepared as described in literature, conditions similar to *Organic Syntheses, Coll. Vol.* 8, p. 247 (1993); *Vol.* 66, p. 173 (1988)) as described in *Journal of Organic Chemistry* 2004, 69, 20, 6920-6922. Another alternative is described in Scheme 2c, reactions of an alkyne of general formula X and a malonate of general formula VII in the presence of $InCl_3$ as described in *Tetrahedron* 2005, 61, 32, 7807-7813, resulting in a compound of general formula IIc.

Scheme 2a

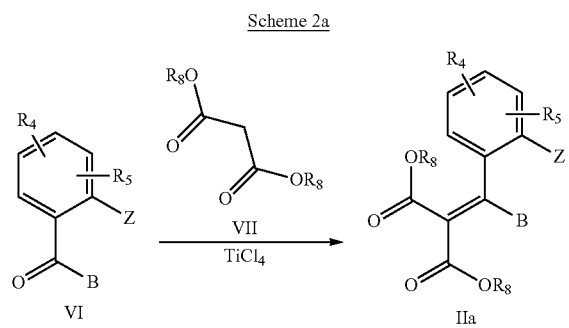

Scheme 2d

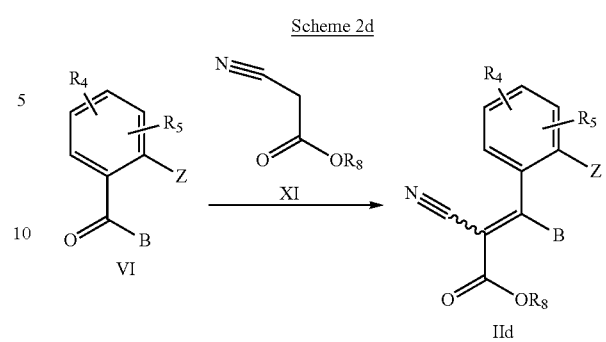

Scheme 2b

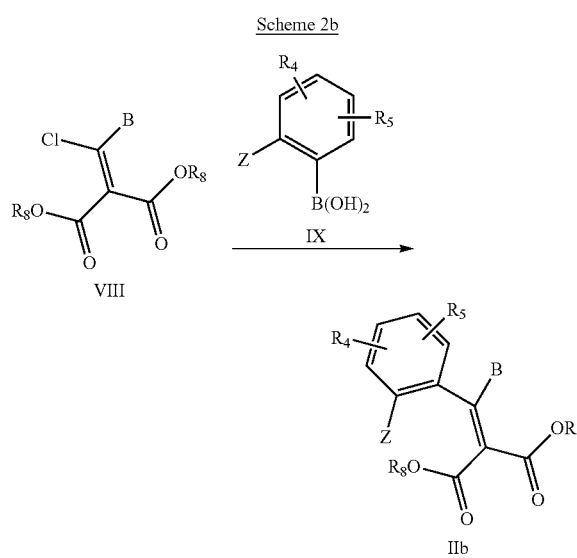

Further examples for the synthesis of compounds of general formula II can be found in: Jones, G. 2011. The Knoevenagel Condensation. Organic Reactions. 204-599. In case the compound of general formula IId is reacted with an amidine of general formula III, possibly in the presence of a base like for example KOAc, NaHCO$_3$ or Na$_2$CO$_3$, a compound of formula IVa can be formed as described in Scheme 3. Besides using this compound directly in the reaction sequence as described in Scheme 1, it can also be converted into an ester derivative of general formula IVb, by performing a nitrile alcoholysis for example by using hydrochloric acid in MeOH or EtOH, followed by reaction with water, resulting in compound IVb as described in Scheme 3.

Scheme 3

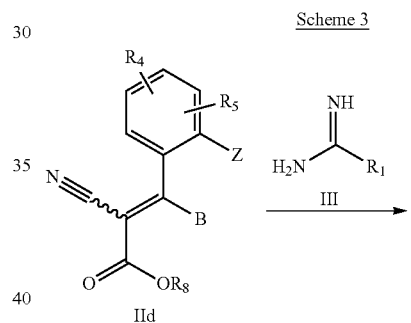

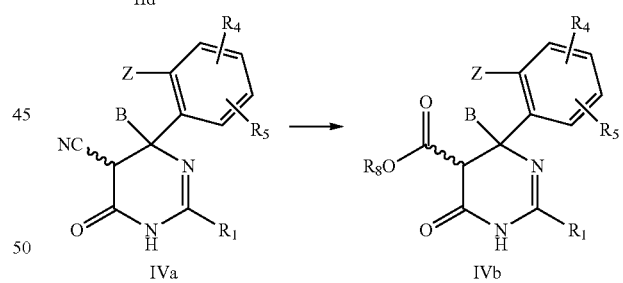

Scheme 2c

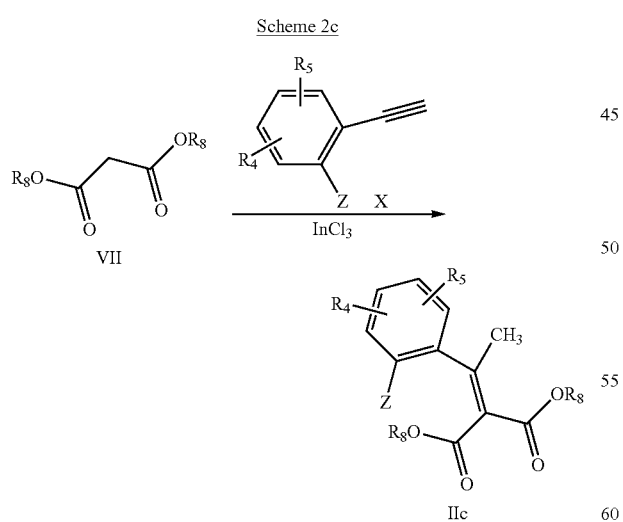

In case the Knoevenagel condensation is performed with an alkyl 2-cyanoacetate of general formula XI and the compound of general formula VI, as described in Scheme 2d, for example β-alanine/acetic acid in benzene can be used as a condition to form the adduct of general formula IId.

Scheme 4

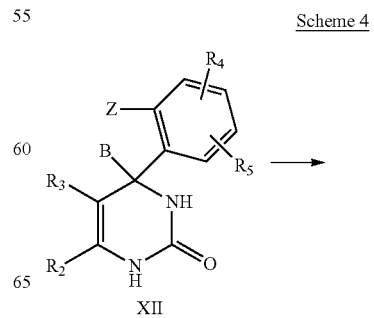

-continued

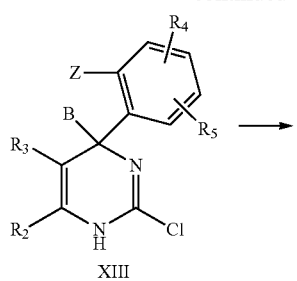

XIII → I

Scheme 6

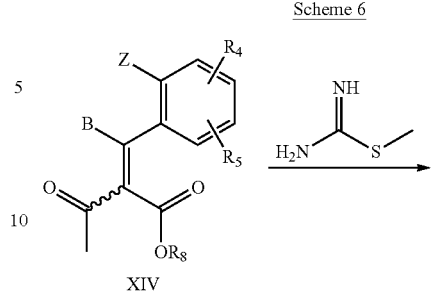

Alternatively, a compound of general formula XII, may be transformed to a compound of general formula XIII as described in Scheme 4, for example by heating in POCl$_3$. The compound of formula XIII can then be transformed in a compound of general formula I by a transition metal catalyzed reaction, for example a Stille-type coupling with R$_1$Sn(Bu)$_3$ and a catalyst like bis(tri-tert-butylphosphine)palladium (0). During this sequence, a protecting group strategy can be used in case functional groups are not compatible with the conditions used, for example a p-Methoxybenzyl protection on a NH functionality.

Scheme 5

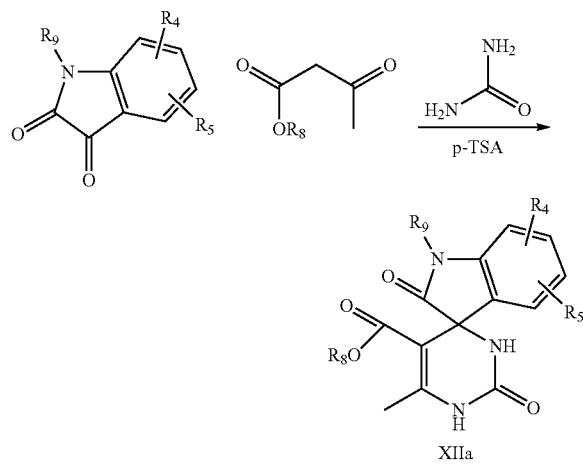

XIIa

A compound of formula XIIa can be synthesized as described in Scheme 5, according to conditions described in Synthetic Communications, 41(19), 2899-2904; 2011. R$_9$ is R$_8$ or H An example of the synthesis of compounds of general formula Ib is depicted in scheme 6. Compound XIV is condensed with 2-methyl-2-thiopseudourea, for example by treating with the hemisulfate of 2-methyl-2-thiopseudourea and sodium bicarbonate in DMF at 50° C., resulting in the formation of compound XV. XV can be further transformed to a compound with general structure Ib for example by using a transition metal catalyzed C—C bond formation, like for example coupling with R$_1$—Sn(Bu)$_3$ in the presence of palladium(II) acetate/butyldi-1-adamantylphosphine and copper (I) bromide-dimethyl sulfide at 140° C. by microwave irradiation.

Examples for the synthesis of compounds with general formula XIV are described in scheme 7a and 7b. In case B equals —CH$_3$, an InCl$_3$ catalyzed coupling of an alkyne X and a C$_1$-C$_3$alkyl-3-oxobutanoate, result in an adduct of general formula XIVc.

Scheme 7a

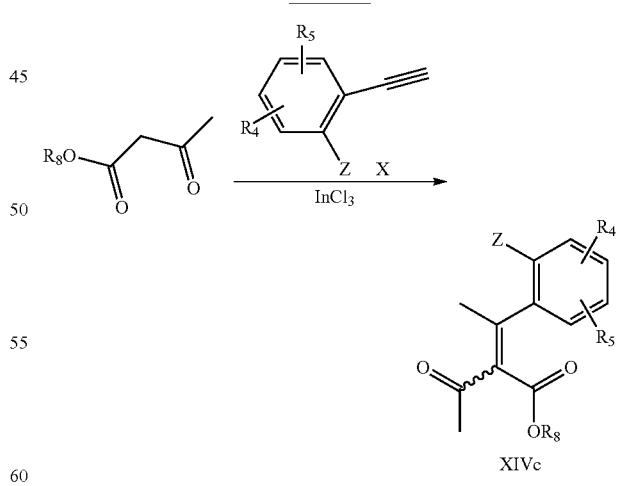

XIVc

Alternatively, condensation of compound VI and a C$_1$-C$_3$alkyl-3-oxobutanoate under Lehnnert conditions (TiCl$_4$/pyridine or modifications hereof), result in a compound of general formula XIV. Examples of suitable compounds represented by VI in this case, are 2,2-difluoro-2,3-dihydro-1H-inden-1-one derivatives.

Scheme 7b

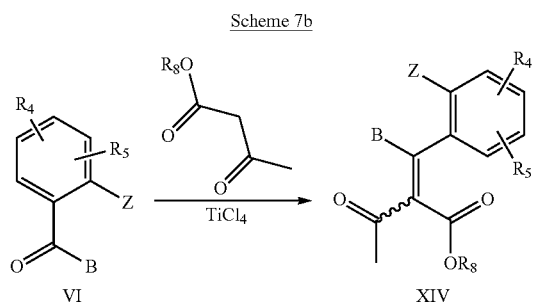

Experimental Part

LCMS Methods

Method A

The LC measurement was performed using an Acquity UPLC (Waters) system. Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 mL/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used. Cone voltage was 10 V for positive ionization mode.

Method B mobile phase A: $H_2O$ (0.1% TFA; B:$CH_3CN$ (0.05% TFA) Stop Time: 2 min; gradient time(min) [% A/% B] 0.01 [90/10] to 0.9 [20/80] to 1.5[20/80] to 1.51 [90/10]; flow: 1.2 mL/min; column temp.: 50° C., Xtimate C18 2.1*30 mm, 3 µm Method C mobile phase A: $H_2O$ (0.1% TFA); B:$CH_3CN$ (0.05% TFA) Stop Time: 10 min; gradient time(min) [% A/% B] 0.0 [90/10] to 0.8 [90/10] to 4.5 [20/80] to 7.5 [20/80]; 9.5 [90/10] flow: 0.8 mL/min; column temp.: 50° C., Agilent TC-C18, 2.1*50 mm, 5 µm Method D The LC measurement was performed using an Acquity UPLC (Waters) system. Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 mL/min. Two mobile phases (mobile phase A: 10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.2 minutes. An injection volume of 0.5 µl was used. Cone voltage was 10 V for positive ionization mode.

Method E

The LC measurement was performed using an Acquity UPLC (Waters) system. Reversed phase UPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 mL/min. Two mobile phases (10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 µl was used.

Cone voltage was 10 V for positive ionization mode

Method F

The HPLC measurement was performed using an Alliance HT 2790 (Waters) system. Reversed phase HPLC was carried out on an Xterra MS C18 column (3.5 µm, 4.6×100 mm) with a flow rate of 1.6 mL/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

Method G

Agilent TC-C18, 50×2.1 mm, 5 µm, mobile phase A: $H_2O$ (0.1% TFA; B:$CH_3CN$ (0.05% TFA) Stop Time: 10 min; Post Time: 0.5 min; gradient time(min) [% A/% B]0 [100/0] to 1 [100/0] to 5 [40/60] to 7.5 [15/85] to 9.5 [100/0]; flow: 0.8 mL/min; column temp.: 50° C.

Method H

YMC-PACK ODS-AQ, 50×2.0 mm, 5 µm, mobile phase A: $H_2O$ (0.1% TFA; B:$CH_3CN$ (0.05% TFA) Stop Time: 10 min; gradient time(min) [% A/% B] 0.0 [90/10] to 0.8 [90/10] to 4.5 [20/80] to 7.5 [20/80] to 8.0 [90/10]; flow: 0.8 mL/min; column temp.: 50° C.

Method I

YMC-PACK ODS-AQ, 50×2.0 mm, 5 µm, mobile phase A: $H_2O$ (0.1% TFA; B:$CH_3CN$ (0.05% TFA) Stop Time: 10 min; gradient time(min) [% A/% B] 0.0 [100/0] to 1 [100/0] to 5 [40/60] to 7.5 [40/60] to 8.0 [100/0]; flow: 0.8 mL/min; column temp.: 50° C.

Method J

XBridge ShieldRP18, 50*2.1 mm, 5 µm; mobile phase: A: $H_2O$ (0.05% $NH_3.H_2O$); B:$CH_3CN$; Stop Time: 10 min; gradient time(min) [% A/% B] 0.0 [100/0] to 1 [100/0] to 5 [40/60] to 7.5 [40/60] to 8.0 [100/0]; flow: 0.8 mL/min; column temp.: 40° C.

Method K

The LC measurement was performed using an Acquity UPLC (Waters) system comprising a binary pump, a sample organizer, a column heater (set at 55° C.), a diode-array detector (DAD). Reversed phase UPLC (Ultra Performance Liquid Chromatography) was carried out on a Acquity UPLC HSS T3 column (1.8 µm, 2.1×100 mm; Waters Acquity) with a flow rate of 0.8 mL/min. Two mobile phases (A: 10 mM ammonium acetate in $H_2O$/acetonitrile 95/5; mobile phase B: acetonitrile) were used to run a gradient condition from 95%

A and 5% B to 0% A and 100% B in 2.5 minutes and subsequently to 5% A and 95% B in 0.5 minutes. An injection volume of 1 μl was used. Cone voltage was 30 V for positive ionization mode and 30 V for negative ionization mode.

Method L

The LC measurement was performed using an Acquity UPLC (Waters) system comprising a binary pump, a sample organizer, a column heater (set at 55° C.), a diode-array detector (DAD). Reversed phase UPLC (Ultra Performance Liquid Chromatography) was carried out on a Acquity UPLC HSS T3 column (1.8 μm, 2.1×100 mm; Waters Acquity) with a flow rate of 0.8 ml/min. Two mobile phases (A: 10 mM ammonium acetate in H$_2$O/acetonitrile 95/5; mobile phase B: acetonitrile) were used to run a gradient condition from 100% A and 0% B to 5% A and 95% B in 2.1 minutes and subsequently to 0% A and 100% B in 0.9 minutes to 5% A and 95% B in 0.5 min. An injection volume of 1 μl was used. Cone voltage was 30 V for positive ionization mode and 30 V for negative ionization mode.

ABBREVIATIONS/TERMS

NMP: 1-Methyl-2-pyrrolidinone
DME: 1,2-dimethoxyethane
POPd: [(t-Bu)$_2$P(OH)]$_2$PdCl$_2$
Isolute® HMN: Disposable liquid-liquid extraction columns containing a modified form of diatomaceous earth
PEPPSI™-IPr: [1,3-Bis(2,6-Diisopropylphenyl)imidazol-2-ylidene](3-chloro-pyridyl)palladium(II) dichloride Compound 1

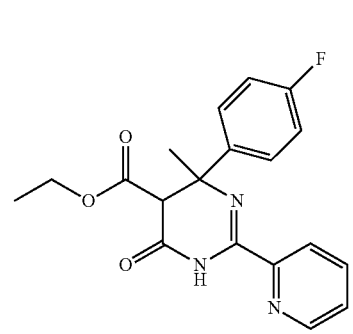

A pressure tube was charged with xylene (30 mL), diethyl malonate (13.3 g, 83.3 mmol), indium chloride (368.2 mg, 1.66 mmol) and 4-fluorophenylacetylene (15 g, 125 mmol). The tube was flushed with nitrogen, closed and stirred in an oil bath at 135° C. for 17 hours. The reaction mixture was cooled to room temperature and the solution was used as such below. A pressure tube was charged with Pyridine-2-carboximidamide hydrochloride (14.2 g, 90.3 mmol) and 1-Methyl-2-pyrrolidinone (NMP, 100 mL). Potassium tert-butoxide (18.42 g, 164 mmol) was added under nitrogen and the reaction mixture was stirred for 30 minutes. Then the above obtained solution in xylene was added, the pressure tube was heated and stirred in an oil bath at 80° C. for 5 hours.

The reaction mixture was cooled in an ice bath and concentrated in vacuo until only NMP remained. The mixture was poured into ice-water and was stirred for 30 minutes. After extraction with diisopropylether (3×100 mL). The combined extracts were washed with brine, dried (MgSO$_4$), filtered and concentrated in vacuo yielding a brown oil. This oil was purified by silica gel column chromatography (gradient CH$_2$Cl$_2$-heptane 50:50 to 100:0). The desired fractions were collected and concentrated in vacuo, yielding compound 1 as a yellow oil which solidified upon standing (21.3 g) Method A; Rt: 1.03 and 1.07 min. m/z: 356.3 (M+H)$^+$ Exact mass: 355.1

Compound 2

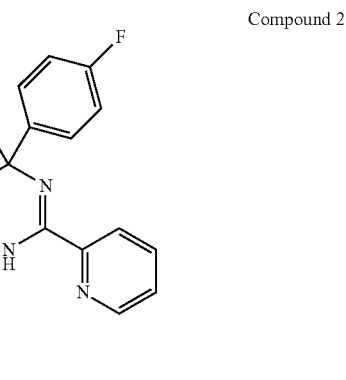

Compound 1 (420 mg, 1.18 mmol), methanol (15 mL) and potassium tert-butoxide (199 mg, 1.77 mmol) were stirred in an oil bath at 80° C. for 17 hours.

The resulting reaction mixture was diluted with water and extracted with CH$_2$Cl$_2$ (3×100 mL). The combined extracts were dried (MgSO$_4$), filtered and concentrated in vacuo yielding a residue as a mixture of a methyl ester (major) and ethyl ester (minor). This mixture and phosphorus oxychloride (2 mL, 21.5 mmol) was refluxed for 1 hour. The mixture was concentrated in vacuo. The resulting residue was taken up in CH$_2$Cl$_2$ and washed with NaHCO$_3$ (sat/aq). The organic layer was dried using (MgSO4), concentrated in vacuo yielding a mixture of the methyl ester (major) and the ethyl ester (minor). To this obtained residue in a microwave vial, cesium carbonate (4.08 g, 12.51 mmol), potassium (morpholin-4-yl) methyltrifluoroborate (0.86 g, 4.17 mmol), water (distilled 1.1 mL, 62.5 mmol) and DME (11 mL) were added. This mixture was purged with nitrogen for 5 minutes. Then, palladium(II) acetate (47 mg, 0.21 mmol) and butyldi-1-adamantylphosphine (120 mg, 0.33 mmol) were added and the reaction mixture was purged with nitrogen for another 2 minutes. The vial was capped and heated under microwave irradiation to 140° C. for 30 minutes. The resulting reaction mixture was concentrated in vacuo and the residue was taken up in water-dichloromethane (50 mL/50 mL). The water layer was further extracted with dichloromethane (2×50 mL). The combined extracts were dried (MgSO$_4$) and concentrated in vacuo. The residue was purified by silica gel column chromatography (gradient ethylacetate-heptane 10:90 to 50:50). The desired fractions were concentrated in vacuo yielding compound 2 as a clear oil which was further purified by preparative HPLC (Uptisphere C18 ODB—10 μm, 200 g, 5 cm). Mobile phase (0.25% NH$_4$HCO$_3$ solution in water, CH$_3$CN) The relevant fraction were concentrated in vacuo, co-evaporated with MeOH (2×10 mL) at 50° C. and dried in a vacuum oven at 55° C. overnight, resulting in compound 2 (170 mg) as a white powder. Method A; Rt: 1.16 min. m/z: 425.5 (M+H)$^+$ Exact mass: 424.2; $^1$H NMR (400 MHz, CHLOROFORM-d) ppm 1.91 (s, 3H), 2.52-2.66 (m, 4H), 3.48 (s, 3H), 3.66 (d, J=16.3 Hz, 1H), 3.73 (d, J=16.3 Hz, 1H), 3.82 (t, J=4.8 Hz, 4H), 6.88-7.04 (m, 2H), 7.37 (ddd, J=7.5, 4.8, 1.0 Hz, 1H), 7.40-7.49 (m, 2H), 7.74 (td, J=7.5, 1.8 Hz, 1H), 8.21 (d, J=7.8 Hz, 1H), 8.50-8.69 (m, 1H), 10.02 (s, 1H)

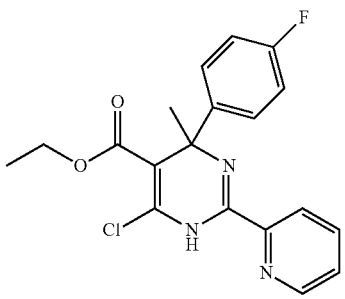

Compound 3

Condition A:

A flask was charged with compound 1 (4 g, 11.0 mmol) and phosphorus oxychloride (10.3 mL, 110.3 mmol). The reaction mixture was stirred in an oil bath at 120° C. for 30 minutes. The reaction mixture was then concentrated in vacuo. The residue was dissolved in dichloromethane (100 mL) and washed with saturated NaHCO$_3$ (50 mL). The organic layer was separated and washed with water, dried (MgSO$_4$), filtered and concentrated in vacuo. The crude was purified by silica gel chromatography (isocratic CH$_2$Cl$_2$) yielding compound 3 as a clear oil which became a solid after standing (2.73 g). Method A; Rt: 1.18 min. m/z: 374.3 (M+H)$^+$ Exact mass: 373.1

Condition B:

A 50 mL round bottomed flask was loaded with a stirring bar, compound 1 (10.0 g, 28.1 mmol) and mixed with phosphorus oxychloride (26.2 mL, 281 mmol). The mixture was stirred at reflux for 30 minutes under a nitrogen atmosphere. The reaction mixture was evaporated to dryness in vacuo. The residue was stored at −20° C. for 40 hours, dissolved in dichloromethane (200 mL) and washed with saturated aqueous sodium bicarbonate (2×100 mL), dried (MgSO$_4$) and evaporated to dryness in vacuo, resulting in compound 3 (9.9 g) as a brown oil which was used as such in next steps.

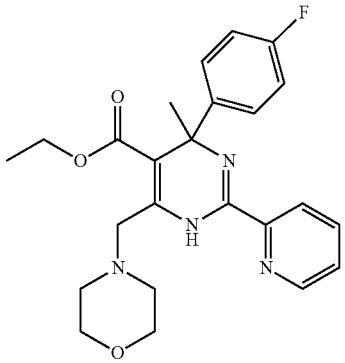

Compound 4

Enantiomers of racemic compound 4: compound 4a and compound 4b

A 10 mL microwave tube was loaded with a stirring bar, potassium (morpholin-4-yl)-methyltrifluoroborate (665 mg, 3.05 mmol), compound 3 (obtained via condition B, 600 mg, 1.53 mmol), cesium carbonate (2.98 g, 9.15 mmol), distilled water (826 µl, 45.7 mmol) and 1,2-dimethoxyethane (7.92 mL, 76.2 mmol) and nitrogen gas was bubbled through during 10 minutes. Under Nitrogen atmosphere palladium(II) acetate (34.5 mg, 0.152 mmol) and butyldi-1-adamantylphosphine (87.5 mg, 0.244 mmol) were added and the reaction mixture was stirred at 140° C. for 10 minutes in microwave oven under nitrogen atmosphere. 1,2-dimethoxyethane was decanted and the water layer was extracted with dichloromethane. The organic layers were combined and evaporated to dryness and the obtained residue was purified using silica gel column chromatography (ethyl acetate:heptane 30-100%) resulting in racemic compound 4 (683 mg), which was further purified using prep SFC separation on (Chiralcel Diacel OJ 20×250 mm). Mobile phase (carbon dioxide, ethanol with 0.2% isopropyl amine). The desired fractions were collected, the solvent was removed in vacuo and the obtained residue dissolved in methanol and evaporated again. Resulting in compound 4a (243 mg) and compound 4b (238 mg), enantiomers of the racemic compound 4. Method E; Rt: 1.21 min. m/z: 439.3 (M+H)$^+$ Exact mass: 438.2. $^1$H NMR (600 MHz, CHLOROFORM-d) ppm 0.99 (t, J=7.1 Hz, 3H), 1.90 (s, 3H), 2.52-2.66 (m, 4H), 3.67 (d, J=16.4 Hz, 1H), 3.75 (d, J=16.3 Hz, 1H), 3.81 (t, J=4.6 Hz, 4H), 3.86-3.97 (m, 2H), 6.96 (t, J=8.8 Hz, 2H), 7.36 (ddd, J=7.4, 4.9, 1.0 Hz, 1H), 7.43 (dd, J=8.8, 5.4 Hz, 2H), 7.72 (td, J=7.7, 1.8 Hz, 1H), 8.18 (d, J=7.9 Hz, 1H), 8.59 (ddd, J=4.8, 1.6, 0.9 Hz, 1H), 10.00 (s, 1H); Columns: OJ-H 500 mm×4.6 mm; Flow: 3 mL/min; Mobile phase: 5% EtOH (containing 0.2% iPrNH$_2$) hold 15.00 min; Column Temperature: 30° C.; Rt, Compound 4a: 3.40 min; Compound 4b: 4.43 min.

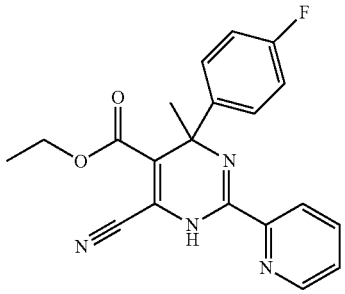

Compound 5

Compound 3 (obtained via condition A, 0.5 g, 1.34 mmol), 1,4-diazabicyclo[2.2.2]-octane (0.23 g, 2.01 mmol), tetrabutylammonium cyanide (0.54 g, 2.01 mmol) and acetonitrile (25 mL) were stirred and heated to 100° C. in a pressure tube for 17 hours. The reaction mixture was concentrated in vacuo and the obtained residue was taken up in dichloromethane/water (50 mL/50 mL). The water layer was extracted with dichloromethane (2×50 mL) and the combined extracts were washed with brine (50 mL), dried (MgSO$_4$), filtered and concentrated in vacuo. The obtained residue was purified by silica gel column chromatography (gradient elution CH$_2$Cl$_2$-heptane 50:50 to 100:0) The desired fractions were concentrated in vacuo, resulting in a yellow oil. The oil was dissolved in diisopropylether and the formed precipitate was filtered on a glass filter and dried in a vacuum oven at 55° C. overnight, resulting in compound 5 (80 mg) as an off white solid. Method D; Rt: 1.10 min. m/z: 365.0 (M+H)$^+$ Exact mass: 364.1.

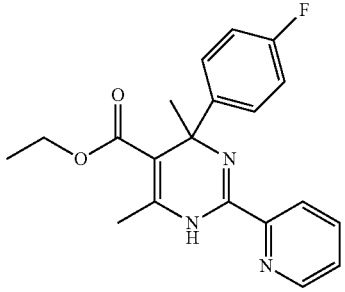

Compound 6

A 10 mL microwave tube was loaded with a stirring bar, potassium (morpholin-4-yl)-methyltrifluoroborate (144 mg, 1.18 mmol), compound 3 (obtained via condition B 170 mg, 0.455 mmol), cesium carbonate (889 mg, 2.73 mmol), distilled water (200 µL, 11.1 mmol) and toluene (2 mL, 18.8 mmol) and nitrogen gas was bubbled through for 10 minutes. Under Nitrogen atmosphere palladium(II) acetate (20.6 mg, 0.0910 mmol) and butyldi-1-adamantylphosphine (52.2 mg, 0.146 mmol) were added and the reaction mixture was stirred at 100° C. for 30 minutes in microwave oven under nitrogen atmosphere and allowed to reach room temperature and the reaction mixture was stirred at 125° C. for 30 minutes in microwave oven under nitrogen atmosphere and allowed to reach room temperature. Palladium(II) acetate (20.6 mg, 0.0910 mmol) and butyldi-1-adamantylphosphine (52.2 mg, 0.146 mmol) were added and the reaction mixture was stirred at 125° C. for 1 hour in microwave oven under nitrogen atmosphere. Potassium (morpholin-4-yl)methyltrifluoroborate (144 mg, 1.18 mmol) and cesium carbonate (889 mg, 2.73 mmol), were added under nitrogen atmosphere.

The reaction mixture was stirred at 125° C. for 10 hours in microwave oven under nitrogen atmosphere. The reaction mixture was diluted with dichloromethane (100 mL) and washed with saturated aqueous sodium carbonate (2×20 mL) and water (20 mL). The organic layer was dried over an isolute HM-N cartridge and concentrated to dryness to afford a brown sticky residue, which was purified using silica gel column chromatography (gradient elution; methanol:dichloromethane 0 to 7%) to afford a dark yellow sticky powder which was dissolved in diethyl ether (2 mL) and petroleum ether (10 mL) was added. The solvent was concentrated (rotavap) to keep 2 mL of solvent which resulted in precipitation of a dark orange solid. The solvent was decanted and the solids were washed with petroleum ether. The combined solutions were concentrated to dryness and the powder was dried in vacuum oven at 50° C. overnight resulting in compound 6 (57 mg) as a yellow powder. Method A; Rt: 1.15 min. m/z: 354.6 (M+H)$^+$ Exact mass: 353.2.

Compound 7

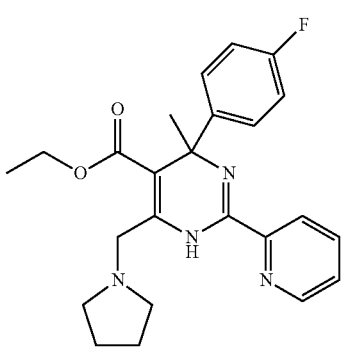

A 10 mL microwave tube was loaded with a stirring bar, potassium (pyrrolidin-1-yl)methyltrifluoroborate (204 mg, 1.07 mmol), compound 3 (obtained via condition A, 200 mg, 0.535 mmol), cesium carbonate (1.05 g, 3.21 mmol), distilled water (290 µl, 16.1 mmol) and 1,2-dimethoxyethane (2.78 mL, 26.8 mmol) and nitrogen gas was bubbled through for 10 minutes. Under nitrogen atmosphere palladium(II) acetate (12.1 mg, 0.0535 mmol) and butyldi-1-adamantylphosphine (30.7 mg, 0.0856 mmol) were added and the reaction mixture was stirred at 140° C. for 20 minutes in microwave oven under nitrogen atmosphere. 1,2-Dimethoxyethane was decanted, the water layer was extracted with dichloromethane and the organic layers were combined and evaporated to dryness. The obtained residue was purified using silica gel column chromatography (gradient elution; ethyl acetate:heptane 10-80%) resulting in compound 7 (119 mg). Method A; Rt: 1.01 min. m/z: 423.4 (M+H)$^+$ Exact mass: 422.2.

Compound 8

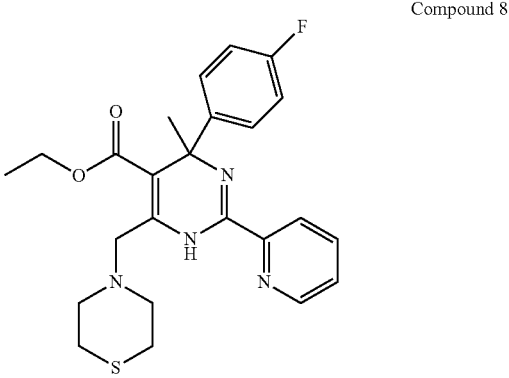 [SMILES: CCOC(=O)C1=C(CN2CCSCC2)NC(c2ccccn2)=NC1(C)c1ccc(F)cc1]

A 10 mL microwave tube was loaded with a stirring bar, potassium (thiomorpholin-4-yl)methyltrifluoroborate (227 mg, 1.02 mmol), compound 3 (obtained via condition B, 200 mg, 0.508 mmol), cesium carbonate (994 mg, 3.05 mmol), distilled water (275 µl, 15.2 mmol) and 1,2-dimethoxyethane (2.64 mL, 25.4 mmol) and nitrogen gas was bubbled through during 10 minutes. Under Nitrogen atmosphere palladium(II) acetate (11.5 mg, 0.0508 mmol) and butyldi-1-adamantylphosphine (29.2 mg, 0.0813 mmol) were added and the reaction mixture was stirred at 140° C. for 10 minutes in microwave oven under nitrogen atmosphere. The product was extracted with dichloromethane and the organic layers were combined and evaporated to dryness. The obtained residue was purified using silica gel column chromatography (ethyl acetate:heptane 5-70%) the desired fractions were collected and concentrated in vacuo, dried overnight in vacuum oven at 50° C., resulting in compound 8 (172 mg). Method A; Rt: 1.38 min. m/z: 423.4 (M+H)$^+$ Exact mass: 422.2.

Compound 9

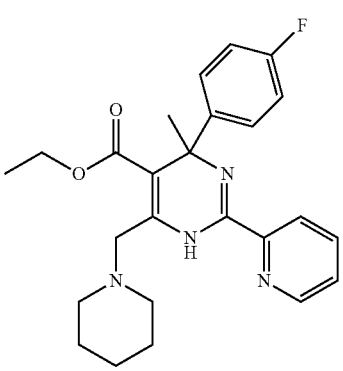

A 10 mL microwave tube was loaded with a stirring bar, potassium (thiomorpholin-4-yl)methyltrifluoroborate (227 mg, 1.02 mmol), compound 3 (obtained via condition B, 200 mg, 0.508 mmol), cesium carbonate (994 mg, 3.05 mmol), distilled water (275 µl, 15.2 mmol) and 1,2-dimethoxyethane (2.64 mL) and nitrogen gas was bubbled through during 10 minutes. Under Nitrogen atmosphere palladium(II) acetate (11.5 mg, 0.0508 mmol) and butyldi-1-adamantylphosphine (29.2 mg, 0.0813 mmol) were added and the reaction mixture was stirred at 140° C. for 10 minutes in microwave oven under nitrogen atmosphere. The product was extracted with dichloromethane and the organic layers were combined and evaporated to dryness and purified twice using silica gel column chromatography (first; ethyl acetate:heptane 5-70%; second; ammonia in methanol (7N)/CH$_2$Cl$_2$ 0-5%) resulting in compound 9 (127 mg) after drying overnight in vacuum oven at 50° C. Method A; Rt: 1.33 min. m/z: 437.4 (M+H)$^+$ Exact mass: 436.2.

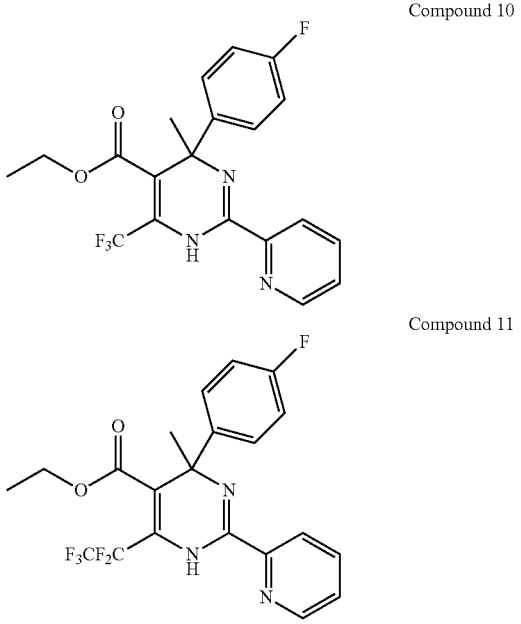

Compound 10

Compound 11

A mixture of potassium fluoride (75 mg, 1.29 mmol) and copper(i) iodide (250 mg, 1.31 mmol) was stirred and heated in vacuo until a homogeneous green color of the mixture was obtained. The reaction was cooled to room temperature, and the same procedure was done three times. After cooling to room temperature, N-Methylpyrrolidone (2.00 mL, 20.8 mmol) and trimethyl(trifluoromethyl)silane (74.2 mg, 1.00 mmol) were added under nitrogen. The reaction mixture was stirred at 50° C. for 45 minutes. It was cooled to room temperature and compound 3 (393 mg, 1.00 mmol) was added under nitrogen. The reaction mixture was stirred at 50° C. for 44 hours and cooled to room temperature and aqueous ammonia was added. The organic layer was separated. The aqueous layer was washed with ethyl acetate (3×10 mL). The combined organic layers were dried with sodium sulphate. The solvent was removed by evaporation in vacuo. The crude product was purified using silica gel column chromatography (ethyl acetate:heptane 5%-50%). The desired fractions were collected and concentrated to dryness resulting in compound 10 (1.2 mg) (Method A; Rt: 1.26 min. m/z: 408.5 (M+H)$^+$ Exact mass: 407.1). and compound 11 (43 mg) (Method A; Rt: 1.36 min. m/z: 458.5 (M+H)$^+$ Exact mass: 457.1). as light yellow oil.

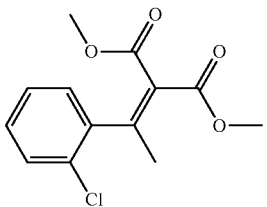

Compound 12

A pressure tube was charged with a stirring bar, dimethyl malonate (4.03 g, 30.5 mmol), 1-chloro-2-ethynylbenzene (5.00 g, 36.6 mmol), indium(III) chloride (162 mg, 0.731 mmol), xylene (15 mL) and flushed with nitrogen and closed. The reaction mixture was then stirred at 135° C. for 17 hours and allowed to reach room temperature. Indium(III) chloride (405 mg, 1.83 mmol) was added to the reaction mixture and flushed with nitrogen and closed. The reaction mixture was then stirred at 130° C. for 16 hours and allowed to reach room temperature and evaporated to dryness. The residue was purified using silica gel column chromatography (gradient elution; 20 to 80% dichloromethane in heptane) resulting in compound 12 (1.26 g) as an oil.

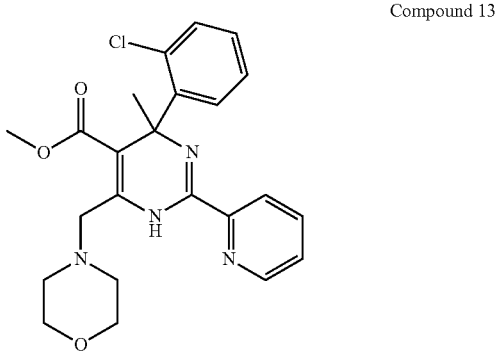 [SMILES: COC(=O)C1=C(CN2CCOCC2)NC(c2ccccn2)=NC1(C)c1ccccc1Cl]

Compound 13

To pyridine-2-carboximidamide hydrochloride (0.813 g, 5.16 mmol), Dimethylformamide (22 mL, 281 mmol) and sodium carbonate (0.994 g, 9.38 mmol) under nitrogen atmosphere and the reaction mixture was stirred for 5 minutes. Then compound 12 (1.26 g, 4.69 mmol) was added and the reaction mixture was heated and stirred at 60° C. for 90 hours and sonicated and the suspension was brought over into a 50 mL round bottomed flask and stirred 18 hours at 68° C. and allowed to come to room temperature. The reaction mixture was poured onto ice water and stirred for 30 minutes. Extracted with diisopropyl ether (3×50 mL). The combined organic extracts were dried (Na$_2$SO$_4$), and concentrated under reduced pressure to afford a sticky oil which was purified using silica gel column chromatography (gradient elution, 30-100% dichloromethane in heptane) The desired fractions were collected and concentrated in vacuo resulting in a residue (356 mg). This residue (356 mg, 0.995 mmol) was dissolved in phosphorous oxychloride (1.61 mL, 22.4 mmol) and heated at 120° C. for 1 hour. The reaction mixture was concentrated to dryness using a nitrogen flow, overnight at 40° C. The obtained residue was dissolved in dichloromethane and washed with aqueous saturated sodium bicarbonate, brine, dried (Na$_2$SO$_4$) and evaporated to dryness resulting in a residue (219 mg) as a dark brown sticky oil which was used as such in the next step. A 10 mL microwave tube was loaded with a stirring bar, potassium (morpholin-4- yl)methyltrifluoroborate (254 mg, 1.16 mmol), the above obtained residue (219 mg), distilled water (315 µl, 17.5 mmol) and 1,2-dimethoxyethane (3 mL). Nitrogen gas was bubbled through during 10 minutes. Under nitrogen atmosphere cesium carbonate (1.14 g, 3.49 mmol), palladium (II) acetate (13.2 mg, 0.0582 mmol) and butyldi-1-adamantylphosphine (33.4 mg, 0.0931 mmol) were added and the reaction mixture was stirred at 140° C. for 10 minutes in microwave oven under nitrogen atmosphere. The product was extracted with dichloromethane and the organic layers were combined, dried (Na$_2$SO$_4$) and concentrated to dryness. The residue was purified by silica gel column chromatography (gradient elution, 5 to 100% ethyl acetate in heptane) resulting in compound 13 (59 mg) as a white powder.

Method A; Rt: 1.17 min. m/z: 441.5 (M+H)$^+$ Exact mass: 440.2

Compound 14

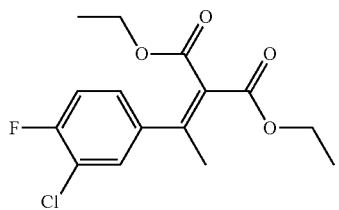

POPd (582 mg, 1.16 mmol) was added to a N$_2$-purged stirring mixture of diethyl 2-(1-chloroethylidene)malonate (3.00 g, 13.6 mmol), 3-chloro-4-fluorophenylboronic acid (3.55 g, 20.4 mmol), and potassium carbonate (5.64 g, 40.8 mmol) in tetrahydrofurane (16 mL) and water (3 mL) in a microwave tube and sealed with a silicon septum. The reaction mixture was subjected to microwave irradiation for 30 minutes at 100° C. The reaction vessel was allowed to reach room temperature and diluted with dichloromethane (150 mL) and washed with water, saturated aqueous sodium carbonate and water (3×40 mL) dried (Na$_2$SO$_4$) and the solvents were removed. The residue was purified using silica gel column chromatography (gradient elution, 0 to 15% ethyl acetate in heptane) resulting in compound 14 (1.89 g).

Compound 15

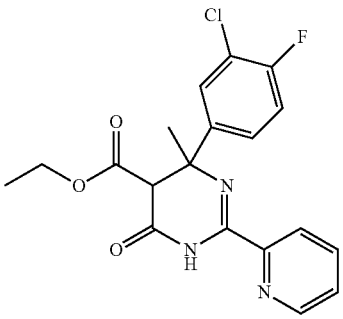

In a sealed pressure tube was loaded under nitrogen atmosphere a stirring bar compound 14 (939 mg, 2.98 mmol), pyridine-2-carboximidamide hydrochloride (470 mg, 2.98 mmol), dry N,N-Dimethylformamide (23.1 mL, 298 mmol) and Potassium tert-butoxide (670 mg, 5.97 mmol). The reaction mixture was stirred at 60° C. for 45 hours, allowed to reach room temperature and poured into ice water. The emulsion was neutralized (pH=7) using aqueous hydrochloric acid (1M) (pH paper check) and extracted with dichloromethane. The combined organic layers were dried (Na$_2$SO$_4$) and concentrated to dryness. N,N-Dimethylformamide was azeotropically removed using toluene to afford a pale yellow oil, which was purified using silica gel column chromatography (10 to 40% ethyl acetate in heptane) resulting in compound 15 (681 mg) which was used as such in the next reaction. Method E; Rt: 1.15 and 1.17 min. m/z: 390.1 (M+H)$^+$ Exact mass: 389.1

Compound 16

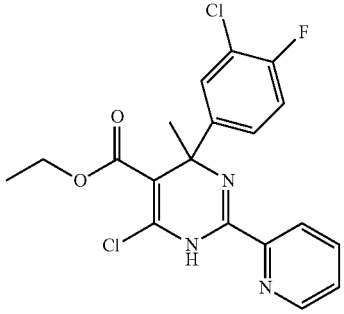

To compound 15 (650 mg, 1.67 mmol), phosphorous oxychloride (2.14 mL, 23.0 mmol) was added in a closed vial. The reaction mixture was stirred and heated at reflux for 30 minutes, cooled to room temperature and concentrated to dryness. The residue was dissolved in dichloromethane and washed with sodium bicarbonate (3×10 mL) dried over an isolate HMN and concentrated to dryness, resulting in compound 16 (724 mg) as a yellow foam which was used as such in next steps. Method E; Rt: 1.23 min. m/z: 408.1 (M+H)$^+$ Exact mass: 407.1

Compound 17

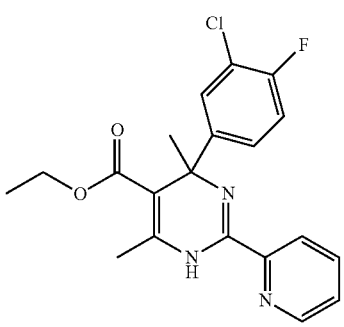

A 10 mL microwave tube was loaded with a stirring bar, potassium methyltrifluoroborate (389 mg, 3.18 mmol) compound 16 (250 mg, 0.612 mmol), cesium carbonate (2.39 g, 7.35 mmol), distilled water (500 µL, 27.7 mmol) and toluene (5 mL, 47.0 mmol) and nitrogen gas was bubbled through for 10 minutes. Under Nitrogen atmosphere palladium(II) acetate (27.7 mg, 0.122 mmol) and butyldi-1-adamantylphosphine (70.3 mg, 0.196 mmol) were added and the reaction mixture was stirred at 125° C. for 10 hours in microwave oven under a nitrogen atmosphere. The reaction mixture was further conventionally heated at 120° C. for 24 hours, cooled to room temperature, diluted with CH$_2$Cl$_2$ (40 mL) and washed with saturated aqueous sodium carbonate (2×5 mL) and water (5 mL). The organic layer was dried over an isolute HMN cartridge and concentrated to dryness to afford a brown sticky residue which was purified using silica gel column chromatography (gradient elution, 0-5% methanol: in dichloromethane) resulting in compound 17 (94 mg).

Method A; Rt: 1.27 min. m/z: 388.3 (M+H)⁺ Exact mass: 387.1

Compound 18

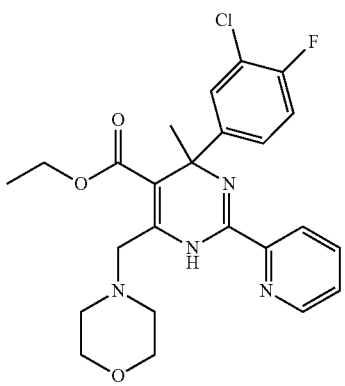

A 10 mL microwave tube was loaded with a stirring bar, potassium (morpholin-4-yl)methyltrifluoroborate (159 mg, 0.767 mmol), compound 16 (222 mg, 0.511 mmol), cesium carbonate (500 mg, 1.53 mmol), water (417 μl, 23.1 mmol) and toluene (3 mL) and purged with nitrogen for 5 minutes. Under nitrogen atmosphere palladium (II) acetate (11.6 mg, 0.051 mmol) and butyldi-1-adamantylphosphine (29.3 mg, 0.082 mmol) were added and the reaction mixture was stirred at 115° C. for 1 hour under a nitrogen atmosphere. Under nitrogen atmosphere more palladium (II) acetate (11.6 mg, 0.051 mmol) and butyldi-1-adamantylphosphine (29.3 mg, 0.082 mmol) were added and the reaction mixture was stirred at 110° C. for 9 hours and then allowed to cool to room temperature. The mixture was diluted with dichloromethane (30 mL) and washed with saturated aqueous sodium carbonate (2×5 mL) and water (5 mL). The organic layer was dried over an isolute HMN cartridge and concentrated to dryness to afford a brown sticky residue which was purified using column chromatography (0-2% MeOH in CH₂Cl₂) and (gradient elution with 10-100% ethyl acetate in heptane). The product fractions were combined, concentrated and dried in a vacuum oven at 50° C. overnight, resulting in compound 18 (71 mg) as a light yellow sticky oil. Method A; Rt: 1.33 min. m/z: 473.4 (M+H)⁺ Exact mass: 472.2; ¹H NMR (400 MHz, 86.7° C., DMSO-d6) ppm 1.01 (t, J=7.0 Hz, 3H), 1.81 (s, 3H), 2.51 (m, 4H), 3.53-3.75 (m, 6H), 3.93 (q, J=7.0 Hz, 2H), 7.20-7.30 (m, 1H), 7.33-7.43 (m, 1H), 7.45-7.58 (m, 2H), 7.89 (td, J=7.7, 1.6 Hz, 1H), 8.08 (d, J=7.8 Hz, 1H), 8.65 (d, J=4.3 Hz, 1H), 9.85 (br. s., 1H)

Compound 19

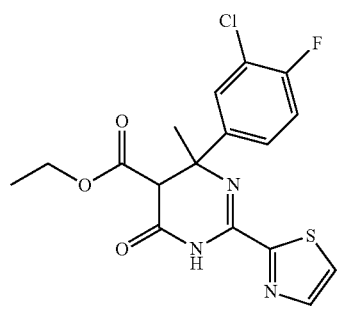

In a sealed pressure tube was loaded under nitrogen atmosphere a stirring bar compound 14 (952 mg, 3.297 mmol), 2-thiazolecarboximidamide hydrochloride (539 mg, 3.30 mmol), dry N,N-Dimethylformamide (25 mL) and Potassium tert-butoxide (740 mg, 6.59 mmol). The reaction mixture was stirred at 60° C. for 112 hours and poured into water and the emulsion was neutralized (pH=5-6) using aqueous hydrochloric acid (1M) (pH paper check) and extracted with dichloromethane. The combined organic layers were dried (Na₂SO₄) and concentrated to dryness and N,N-Dimethylformamide was azeotropically removed using toluene to afford a pale yellow oil which was purified using column chromatography (ethyl acetate:heptane 10 to 40%) to afford compound 19 (379 mg) as a light yellow powder which was used as such in the next reaction.

Compound 20

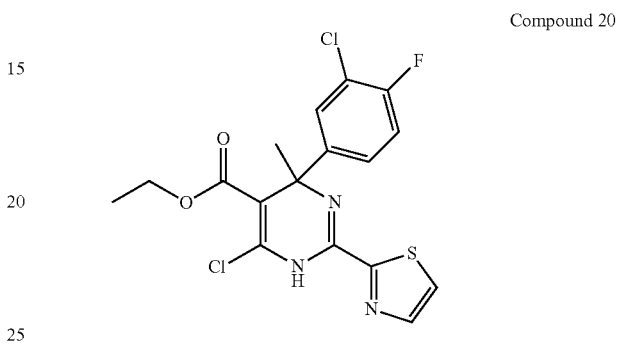

To compound 19 (335 mg, 0.846 mmol) was added phosphorus oxychloride (1.10 mL, 11.8 mmol) and the reaction mixture was stirred heated at reflux for 30 minutes and allowed to cool to room temperature and concentrated to dryness under a nitrogen flow. The residue was dissolved in dichloromethane and washed with saturated sodium bicarbonate and water and dried over an isolute HMN cartridge and concentrated to dryness to afford compound 20 as yellow foam which was used as such in next steps.

Compound 21

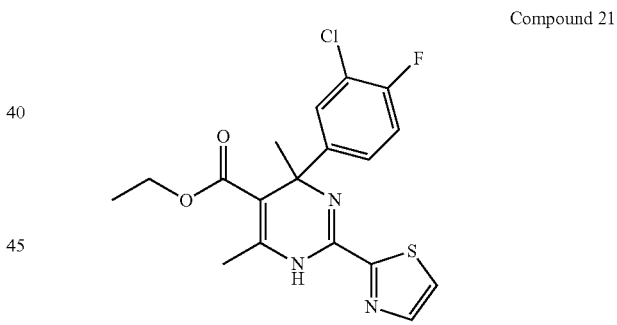

A microwave vial was charged with toluene (4 mL) and water (4004) and this was purged with nitrogen for 5 minutes. Then compound 20 (100 mg) was added followed by cesium carbonate (944 mg, 2.9 mmol) and potassium methyltrifluoroborate (153 mg, 1.26 mmol) and the reaction mixture was purged for another two minutes. Then palladium(II) acetate (10.9 mg, 0.048 mmol) and butyldi-1-adamantylphosphine (27.7 mg, 0.077 mmol) were added and the reaction mixture was purged for another two minutes. The microwave vial was flushed with nitrogen and capped. The reaction mixture was heated under microwave irradiation to 140° C. for 1 hour. The reaction mixture was cooled to room temperature and poured into dichloromethane-water (50 mL-50 mL). The layers were separated and the water layer was extracted twice using dichloromethane (2×50 mL). The combined extracts were washed with brine, dried (MgSO₄), filtered and concentrated in vacuo. The filtrate was concentrated and purified by silica gel column chromatography by gradient elution with 10% to 100% EtOAc in heptanes and further purified by preparative HPLC (Uptisphere C18 ODB—10 μm, 200 g, 5 cm). Mobile phase (0.25% NH$_4$HCO$_3$ solution in water, CH$_3$CN), resulting in compound 21 (4.6 mg).

Compound 22

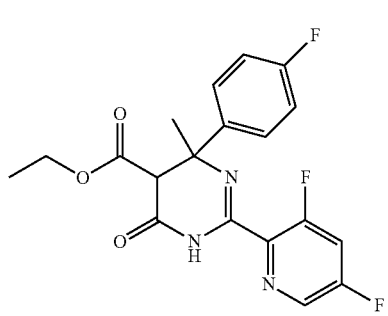

A pressure tube was charged with a stirring bar, diethyl malonate (15.4 g, 96.1 mmol), 4-fluorophenylacetylene (15.0 g, 125 mmol), indium(III) chloride (1.06 g, 4.80 mmol) and o-Xylene (35 mL) and flushed with nitrogen and closed. The reaction mixture was then stirred in an oil bath at 135° C. for 17 hours and cooled to room temperature. The reaction mixture was used as such in the next step.

A pressure tube was charged with 3,5-fluoro-Pyridine-2-carboximidamide (2.91 g, 15.0 mmol), NMP (16.6 mL, 173 mmol) and Potassium tert-butoxide (3.06 g, 27.3 mmol) under a nitrogen atmosphere and the reaction mixture was stirred for 30 minutes. Then part of the above obtained reaction mixture in o-xylene (13.6 mmol, 5 mL reaction mixture in o-xylene) was added and the reaction mixture was heated and stirred in an oil bath at 80° C. for 3 hours. After cooling to room temperature, the reaction mixture was concentrated in vacuo to remove o-xylene. Then it was poured into ice-cold water and neutralized (pH=7) using aqueous hydrochloric acid (1M) (pH paper check). The mixture was stirred for 30 minutes and then extracted with diisopropyl ether (3×50 mL). The combined organic extracts were washed with brine, dried (Na$_2$SO$_4$), concentrated in vacuo and dried over weekend in vacuum oven at 50° C. The obtained brown oil was purified by silica gel column chromatography (40-100% dichloromethane in heptane). The desired fractions were concentrated in vacuo resulting in compound 22 (740 mg) as a white powder.

Compound 23

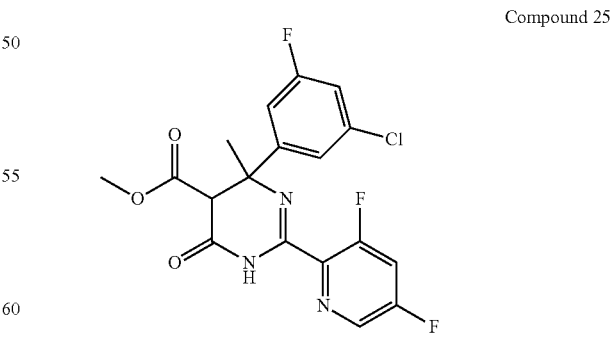

To a tube with a stirring bar, compound 22 (740 mg, 1.86 mmol) and phosphorous oxychloride (1.34 mL, 18.6 mmol) were added and the tube was closed with a Teflon cap. The reaction mixture was heated at 120° C. for 30 minutes and concentrated to dryness using a nitrogen flow at 40° C. The residue was dissolved in dichloromethane and washed with aqueous saturated sodium bicarbonate and brine, dried (Na$_2$SO$_4$) and evaporated to dryness resulting in compound 23 (750 mg) as a dark brown sticky oil which was used as such in the next step.

Compound 24

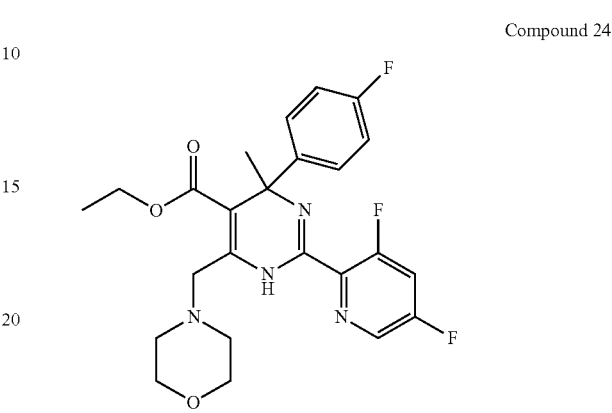

A 10 mL microwave tube was loaded with a stirring bar, potassium (morpholin-4-yl)-methyltrifluoroborate (189 mg, 0.869 mmol), compound 23 (250 mg, 0.58 mmol), distilled water (314 μl, 17.4 mmol) and 1,2-dimethoxyethane (3 mL) and nitrogen gas was bubbled through during 10 minutes. Under Nitrogen atmosphere cesium carbonate (944 mg, 2.90 mmol), palladium(II) acetate (13.1 mg, 0.058 mmol) and butyldi-1-adamantylphosphine (33.2 mg, 0.0927 mmol) were added and the reaction mixture was stirred at 140° C. for 10 minutes in microwave oven. The product was extracted with dichloromethane, the organic layers were combined, dried over sodium sulphate and evaporated to dryness and purified using silica gel column chromatography (gradient elution with 5-80% ethyl acetate in heptane) resulting in compound 24 (65 mg) as a white powder which was dried overnight in vacuum oven at 50° C. Method A; Rt: 1.21 min. m/z: 475.5 (M+H)$^+$ Exact mass: 474.2; $^1$H NMR (400 MHz, DMSO-d$_6$) ppm 0.95 (t, J=7.0 Hz, 3H), 1.79 (s, 3H), 2.37-2.48 (m, 4H), 3.52 (d, J=15.6 Hz, 1H), 3.57-3.69 (m, 5H), 3.79-3.96 (m, 2H), 7.09 (t, J=8.9 Hz, 2H), 7.36-7.46 (m, 2H), 8.05 (ddd, J=10.9, 9.0, 2.3 Hz, 1H), 8.65 (d, J=2.0 Hz, 1H), 9.61 (s, 1H)

Compound 25

A microwave tube was charged with a stirring bar, dimethyl malonate (0.712 g, 5.39 mmol), 3-chloro-5-fluorophenylacetylene (1.00 g, 6.47 mmol), indium(III) chloride (71.5 mg, 0.324 mmol), xylene (3 mL) and flushed with nitrogen and closed. The reaction mixture was then stirred at 135° C.

for 17 hours and allowed to cool to room temperature. Indium (III) chloride (71.5 mg, 0.324 mmol) was added and the reaction mixture was stirred at 135° C. for 17 hours and next cooled to room temperature. The reaction mixture was used as such.

To a pressure tube charged with 3,5-fluoro-Pyridine-2-carboximidamide (1.15 g, 5.93 mmol), N-Methylpyrrolidone (6.57 mL, 68.2 mmol) under a nitrogen atmosphere was added potassium tert-butoxide (1.21 g, 10.8 mmol). The reaction mixture was stirred for 30 minutes. Then part of the above reaction mixture in xylene (5.39 mmol, 3 mL solution in xylene) was added and the pressure tube was heated and stirred in an oil bath at 80° C. for 4 hours. The reaction mixture was poured onto ice water and neutralized (pH=7) using aqueous hydrochloric acid (1M) (pH paper check). The mixture was stirred 30 minutes and then it was extracted with diisopropylether (3×50 mL). The combined extracts were washed with brine, dried ($Na_2SO_4$), filtered and concentrated in vacuo and the residue was purified using silica gel column chromatography (gradient elution 40-100% dichloromethane in heptane). The desired fractions were concentrated in vacuo resulting in compound 25 (400 mg) as a brownish sticky oil.

Compound 26

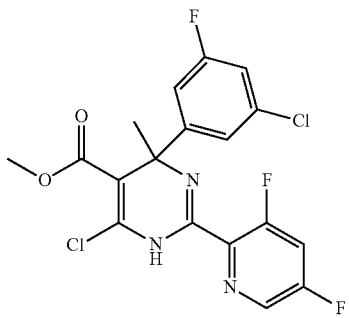

A tube was charged with a stirring bar, compound 25 (400 mg, 0.826 mmol), phosphorous oxychloride (1.19 mL, 16.5 mmol) and heated at 120° C. for 45 minutes. The reaction mixture was concentrated to dryness using a nitrogen flow overnight at 40° C. The residue was dissolved in dichloromethane and washed with aqueous saturated sodium bicarbonate, brine, dried ($Na_2SO_4$) and evaporated to dryness resulting in compound 26 (239 mg) as a dark brown oil which was used as such in the next step.

Compound 27

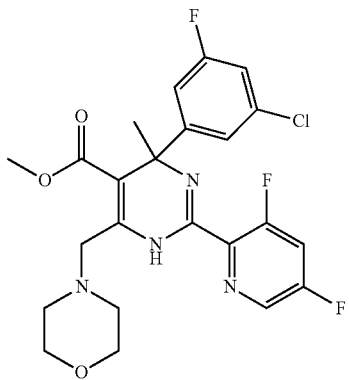

A 10 mL microwave tube was loaded with a stirring bar, potassium (morpholin-4-yl)methyltrifluoroborate (182 mg, 0.833 mmol), compound 26 (239 mg, 0.556 mmol), distilled water (301 µl, 16.7 mmol) and 1,2-dimethoxyethane (2.88 mL) and nitrogen gas was bubbled through during 10 minutes. Under nitrogen atmosphere, cesium carbonate (905 mg, 2.78 mmol), palladium(II) acetate (12.6 mg, 0.0556 mmol) and butyldi-1-adamantylphosphine (31.9 mg, 0.0889 mmol) were added and the reaction mixture was stirred at 140° C. for 10 minutes in microwave oven under a nitrogen atmosphere. The product was extracted with dichloromethane and the organic layers were combined, dried ($Na_2SO_4$) and evaporated to dryness. The obtained residue was purified using silica gel column chromatography (5 to 70% ethyl acetate in heptane) to afford compound 27 (19 mg) as a yellow-white powder. Method A; Rt: 1.26 min. m/z: 495.5 $(M+H)^+$ Exact mass: 494.1; $^1H$ NMR (400 MHz, CHLOROFORM-d) ppm 1.89 (s, 3H), 2.48-2.65 (m, 4H), 3.53 (s, 3H), 3.67 (d, J=16.6 Hz, 1H), 3.72 (d, J=16.6 Hz, 1H), 3.78 (t, J=4.6 Hz, 4H), 6.90 (dt, J=8.3, 2.1 Hz, 1H), 7.24-7.27 (m, 1H), 7.30 (ddd, J=10.0, 7.9, 2.4 Hz, 1H), 8.35 (d, J=2.0 Hz, 1H), 9.69 (s, 1H)

Compound 28

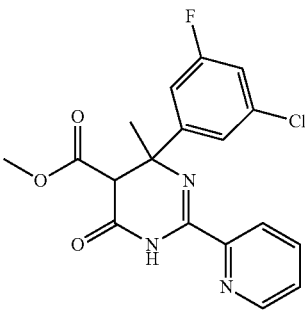

A 10 ml microwave tube was charged with dimethyl malonate (1.21 g, 9.17 mmol), 3-chloro-5-fluorophenylacetylene (1.70 g, 11.0 mmol), indium(III) trichloride (243 mg, 1.10 mmol), xylene (6 mL) and flushed with nitrogen and closed. The reaction mixture was stirred at 135° C. for 40 hours, allowed to cool to room temperature and used as such in next step. A 50 mL round bottomed flask was charged with pyridine-2-carboximidamide hydrochloride (1.52 g, 9.62 mmol), dimethylformamide (8.98 mL), and sodium carbonate (2.91 g, 27.5 mmol) under a nitrogen atmosphere and the reaction mixture was stirred for 10 minutes zy room temperature. Then the reaction mixture in xylene obtained above (9.17 mmol) was added and the obtained mixture was heated and stirred at 60° C. overnight. The mixture was poured into ice water and stirred for 30 minutes and extracted with diisopropyl ether (3×50 mL). The combined organic extracts were dried ($Na_2SO_4$), concentrated under reduced pressure and the residue was purified using silica gel column chromatography (gradient elution 30 to 100% dichloromethane: in heptane) The desired fractions were concentrated in vacuo resulting in compound 28 (1.14 g) as a brown oil.

Compound 29

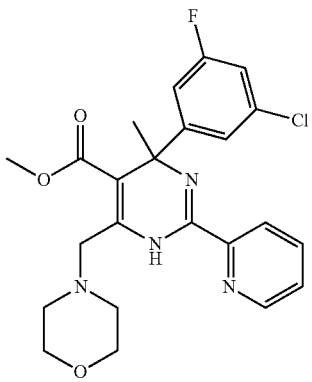

Under a nitrogen atmosphere a tube was loaded with a stirring bar, compound 28 (1.14 g, 3.03 mmol) and phosphorous oxychloride (4.37 mL, 60.7 mmol) and heated at 120° C. for 45 minutes. The reaction mixture was concentrated to dryness using a nitrogen flow overnight at 40° C. The residue was dissolved in dichloromethane and washed with aqueous saturated sodium bicarbonate and brine, dried (Na$_2$SO$_4$) and evaporated to dryness to afford a residue which was used as such in next step. A 20 mL microwave tube was loaded with a stirring bar, potassium (morpholin-4-yl)methyltrifluoroborate (1.03 g, 4.72 mmol), the above obtained residue (969 mg, 2.36 mmol), distilled water (1.28 mL, 70.9 mmol) and 1,2-dimethoxyethane (12.3 mL, 118 mmol). Nitrogen gas was bubbled through during 10 minutes. Under nitrogen atmosphere, cesium carbonate (4.62 g, 14.2 mmol), palladium (II) acetate (53.5 mg, 0.236 mmol) and butyldi-1-adamantylphosphine (135 mg, 0.378 mmol) were added and the reaction mixture was stirred at 140° C. for 10 minutes in microwave oven under nitrogen atmosphere. The water layer was extracted with dichloromethane, the organic layers were combined and washed with aqueous saturated sodium carbonate, dried (Na$_2$SO$_4$) and evaporated to dryness. The residue was purified using silica gel column chromatography (gradient elution 5 to 50% ethyl acetate in heptane) resulting in compound 29 (453 mg). Method A; Rt: 1.30 min. m/z: 459.5 (M+H)$^+$ Exact mass: 458.2; $^1$H NMR (400 MHz, CHLOROFORM-d) ppm 1.87 (s, 3H), 2.52-2.69 (m, 4H), 3.50 (s, 3H), 3.69 (d, J=16.8 Hz, 1H), 3.76 (d, J=16.6 Hz, 1H), 3.82 (t, J=4.5 Hz, 4H), 6.90 (dt, J=8.3, 2.0 Hz, 1H), 7.07 (dt, J=10.1, 1.9 Hz, 1H), 7.24 (t, J=1.8 Hz, 1H), 7.38 (ddd, J=7.5, 5.0, 0.9 Hz, 1H), 7.75 (td, J=7.7, 1.6 Hz, 1H), 8.18 (d, J=7.8 Hz, 1H), 8.60 (d, J=4.8 Hz, 1H), 10.14 (s, 1H).

Compound 30

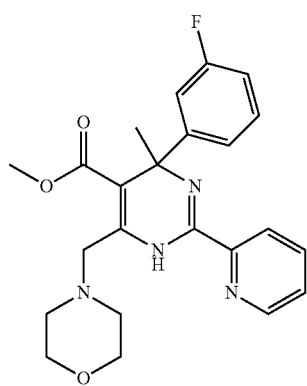

Compound 31

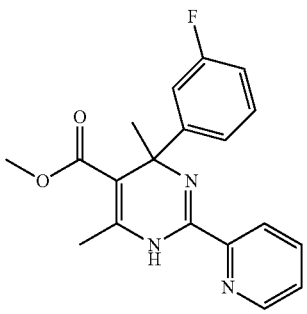

Compound 29 (175 mg, 0.378 mmol) and potassium acetate (148 mg, 1.51 mmol) were dissolved in methanol (50 mL) and the reaction mixture was stirred and purged with nitrogen gas for 5 minutes. Palladium on carbon (10%, 201 mg, 0.189 mmol) was added to the solution which was stirred under hydrogen atmosphere for 2 hours. The reaction mixture was filtered on dicalite under a nitrogen atmosphere and the solids were washed with methanol. The filtrate was concentrated to dryness and the obtained residue was purified using silica gel column chromatography (gradient elution 5-65% ethyl acetate in heptanes) resulting in compound 30 (66 mg) and compound 31 (13 mg). Compound 30: Method A; Rt: 1.18 min. m/z: 425.5 (M+H)$^+$ Exact mass: 424.2; $^1$H NMR (400 MHz, CHLOROFORM-d) ppm 1.90 (s, 3H), 2.51-2.68 (m, 4H), 3.47 (s, 3H), 3.67 (d, J=16.6 Hz, 1H), 3.74 (d, J=16.6 Hz, 1H), 3.81 (t, J=4.5 Hz, 4H), 6.79-6.91 (m, 1H), 7.13-7.20 (m, 1H), 7.21-7.26 (m, 2H), 7.36 (ddd, J=7.5, 5.0, 1.1 Hz, 1H), 7.73 (td, J=7.8, 1.8 Hz, 1H), 8.19 (dt, J=8.0, 1.0 Hz, 1H), 8.59 (ddd, J=4.8, 1.8, 0.8 Hz, 1H), 10.05 (s, 1H)

Compound 31: Method A; Rt: 1.12 min. m/z: 340.4 (M+H)$^+$ Exact mass: 339.1

Compound 32

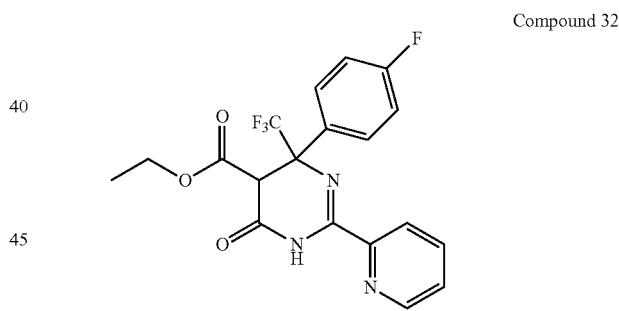

THF (300 mL) was slowly added to TiCl$_4$ (1 M in dichloromethane; 20.3 mL 184.0 mmol) in an icebath. CCl$_4$ (4 mL) was added. Then a mixture of 2,2,2,4'-tetrafluoro-acetophenone (18.9 g, 98.1 mmol) and diethylmalonate (15.7 g, 98.1 mmol) was added at a temperature between 0-5° C. The recipient was rinsed with CCl$_4$ (1 mL). The reaction mixture was stirred 90 minutes at room temperature. Then pyridine (30.7 mL) was added dropwise during 5 minutes. The reaction mixture was stirred 90 minutes at room temperature. Water was added until the white precipitate dissolved completely. The mixture was extracted twice with diethylether (250 mL). The organic layer was separated, dried over sodium sulphate, filtered and concentrated. The residue was purified by silica gel column chromatography using a gradient elution from 0 till 10% EtOAc in heptane. The pure fractions were combined and concentrated resulting in diethyl 2-(2,2,2-trifluoro-1-(4-fluorophenyl)ethylidene)malonate as a clear liquid (5.35 g). $^1$H NMR (400 MHz, DMSO-d$_6$) ppm 0.88 (t, J=1.0 Hz, 3H), 1.27 (t, J=7.0 Hz, 3H), 3.99 (q, J=7.2 Hz, 2H), 4.33 (q, J=7.1 Hz, 2H), 7.28-7.37 (m, 2H), 7.37-7.45 (m, 2H).

Diethyl 2-(2,2,2-trifluoro-1-(4-fluorophenyl)ethylidene) malonate (15.4 mmol), (2.43 g, 15.4 mmol), pyridine-2-carboximidamide hydrochloride, potassium acetate (2.27 g; 23.1 mmol) in DMF (23 mL) was stirred and heated at 110° C. in during 2 hours. The reaction mixture was concentrated in vacuo. The residue was taken up in water (50 mL) and dichloromethane (50 mL). The organic layer was dried over an HM-N isolute cartridge and concentrated. The residue was purified by silica gel column chromatography using a gradient from 1 till 10% methanol. The product fractions were collected and concentrated. Impure fractions were crystallized from 90/10 heptane/ethylacetate mixtures. The white powders were filtered off and dried in vacuum overnight at 50° C. resulting in compound 32 (2.33 g). The filtrates were combined and concentrated resulting in an oily residue (2.06 g) which was further purified by Prep HPLC on (RP Vydac Denali C18-10 µm, 200 g, 5 cm). Mobile phase (0.25% $NH_4HCO_3$ solution in water, $CH_3CN$), the desired fractions were collected, evaporated, dissolved in MeOH and evaporated again, resulting in more compound 32 (1.48 g) as a white powder. $^1$H NMR (400 MHz, DMSO-$d_6$) ppm 0.74 (t, J=7.0 Hz, 2H), 1.14 (t, J=7.2 Hz, 1H), 3.68-3.83 (m, 1H), 4.07-4.19 (m, 1H), 4.57-4.65 (m, 1H), 7.20-7.37 (m, 2H), 7.61-7.81 (m, 2H), 8.00 (dd, J=8.8, 5.5 Hz, 1H), 8.05-8.14 (m, 1H), 8.37 (dt, J=8.0, 1.0 Hz, 1H), 8.47 (dt, J=7.8, 1.0 Hz, 1H), 8.68-8.78 (m, 1H), 11.25 (s, 1H), 11.42 (s, 1H)

Compound 33

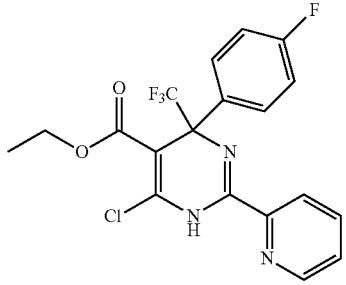

Compound 32 (2.29 g, 5.48 mmol) dissolved in phosphorus oxychloride (30 mL) was refluxed overnight. The reaction mixture was concentrated and the residue was dissolved in $CH_2Cl_2$ (50 mL) and poured in $NaHCO_3$ solution. The mixture was stirred vigorously for 5 minutes. The organic layer was dried over an isolute HM-N cartridge and concentrated. The residue was dissolved in a small amount of $CH_2Cl_2$ and subjected to silica gel column chromatography using a gradient from 10 till 100% EtOAc. The product fractions were collected and concentrated resulting in compound 33, which was used as such in the next reaction.

Compound 34

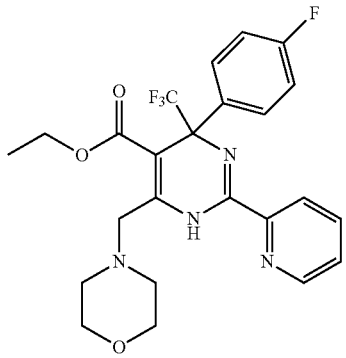

Enantiomers of Racemic Compound 34: Compound 34a and Compound 34b

Nitrogen was bubbled through a mixture of compound 33 (0.48 g, 1.04 mmol), potassium (morpholin-4-yl)methyltrifluoroborate (0.34 g, 1.56 mmol) potassium carbonate (0.216 g, 1.56 mmol), dioxane (47 mL) and distilled water (9 mL). bis(tri-t-butylphosphine)palladium(0)(0.16 g, 0.31 mmol) was added and the reaction mixture was heated in a microwave at 140° C. during 30 minutes. The reaction mixture was concentrated, dissolved in water and $CH_2Cl_2$. The organic layer wad dried over an HM-N cartridge and concentrated. The residue was purified by column chromatography yielding compound 34 (320 mg) was used for enantiomer separation on SFC. Part of the residue (253 mg) was separated in enantiomers by Preperative SFC (Chiralcel Diacel OJ 20×250 mm). Mobile phase ($CO_2$, MeOH), the desired fractions were collected, evaporated, dissolved in MeOH and evaporated again, resulting in compound 34a (98.5 mg) and compound 34b (89 mg) $^1$H NMR (400 MHz, $CDCl_3$-d) ppm 1.00 (t, J=7.0 Hz, 3H), 2.51-2.65 (m, 4H), 3.70 (s, 2H), 3.81 (t, J=4.5 Hz, 4H), 3.95 (dddd, J=18.3, 11.1, 7.2, 3.6 Hz, 2H), 6.95-7.04 (m, 2H), 7.42 (ddd, J=7.5, 4.9, 1.1 Hz, 1H), 7.50 (dd, J=8.3, 5.3 Hz, 2H), 7.79 (td, J=7.7, 1.6 Hz, 1H), 8.29 (d, J=8.0 Hz, 1H), 8.62 (d, J=4.8 Hz, 1H), 10.39 (br. s., 1H). Method E; Rt: 1.26 min. m/z: 493.2 (M+H)$^+$ Exact mass: 492.2; SFC: OJ-H 500 mm×4.6 mm; Flow: 3 mL/min; Mobile phase: 5% MeOH (containing 0.2% $iPrNH_2$) hold 15.00 min.; Column Temperature: 30° C. 34a: 2.57 min; 34b: 3.55 min.

Compound 35

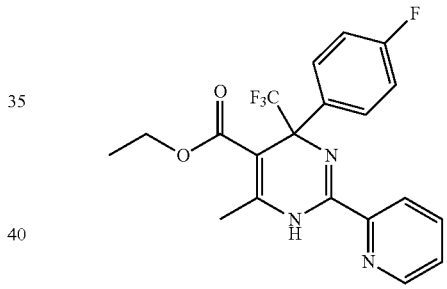

Nitrogen was bubbled through a solution of compound 33 (145 mg, 0.314 mmol), and $SnMe_4$ (112 mg, 0.628 mmol) in DMF (2 mL) during 10 minutes. Then bis(tri-t-butyl-phosphine)palladium(0) (80.3 mg, 0.157 mmol) was added and the reaction mixture was stirred under microwave irradiation at 140° C. for 10 minutes. The reaction mixture was concentrated and the obtained residue was dissolved in $CH_2Cl_2$ (25 mL), washed with water (2×), dried over an HM-N isolute cartridge and concentrated. The residue was dissolved in dichloromethane, filtered and concentrated to dryness in vacuo. The obtained residue was purified by silica gel column chromatography using gradient elution 10 to 50% EtOAc in heptane. The product fractions were collected and concentrated to dryness. The residue was purified again by silica gel column chromatography using $CH_2Cl_2$ as eluent. The product fractions were collected and concentrated. The resulting residue was purified by Prep HPLC on (RP SunFire Prep C18 OBD-10 µm, 30×150 mm). Mobile phase (0.25% $NH_4HCO_3$ solution in water, $CH_3CN$), resulting in compound 35 (36 mg). Method E; Rt: 1.19 min. m/z: 408.2 (M+H)$^+$ Exact mass: 407.1; $^1$H NMR (400 MHz, DMSO-$d_6$) ppm 1.00 (t, J=7.2 Hz, 3H), 2.22 (s, 3H), 3.87-4.02 (m, 2H), 7.12-7.23 (m, 2H), 7.53 (dd, J=8.5, 5.5 Hz, 2H), 7.59-7.66 (m, 1H), 7.94-8.01 (m, 1H), 8.13 (d, J=8.0 Hz, 1H), 8.65-8.74 (m, 1H), 10.10 (s, 1H)

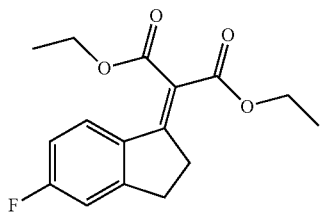

Compound 36

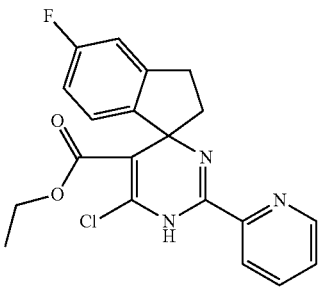

Compound 38

5-fluoro-2,3-dihydro-1H-inden-1-one (20 g, 133 mmol) and diethyl malonate (13.5 g, 146 mmol) were dissolved in dry THF (560 mL). TiCl$_4$ (29.3 g, 266 mmol) in dry CH$_2$Cl$_2$ (260 mL) was added dropwise at 0° C. under N$_2$. After addition, pyridine (56 mL) was added dropwise at 0° C. under N$_2$. The mixture was stirred overnight at 20° C. The solid was filtered off. The filtrate was concentrated in vacuo and ethyl acetate (400 mL) was added. The resulting precipitate was filtered off. The filtrate was washed with brine (2×200 mL) and dried over Na$_2$SO$_4$. The solvent was removed under high vacuum. The residue was purified by silica gel chromatography (gradient eluent:petroleum ether:ethyl acetate: from 100:0 to 10:1) resulting in a residue (9.8 g). The obtained product was further purified by high-performance liquid chromatography (C18, eluent: CH$_3$CN/H$_2$O from 15/85 to 45/55 with 0.1% HCl as buffer). The pure fractions were collected and the mixture was basified with NaHCO$_3$ to pH=8. The volatiles were removed in vacuo. The aqueous layer was extracted with ethyl acetate (200 mL). The organic layer was washed with brine and dried over Na$_2$SO$_4$. The solvent was removed in vacuo, resulting in compound 36 (5 g).

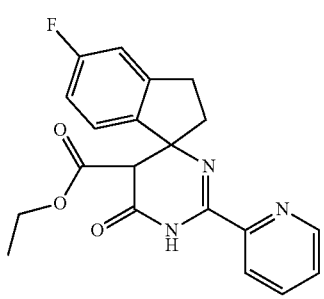

Compound 37

A mixture of compound 36 (7 g, 23.9 mmol), pyridine-2-carboximidamide hydrochloride (5.7 g) and Na$_2$CO$_3$ (7.6 g, 71.8 mmol) in DMF (70 mL) was stirred overnight at 60° C. under N$_2$. The solvent was removed in vacuo. The obtained residue was suspended in dichloromethane (100 mL) and the precipitate was filtered off. The filtrate was concentrated and purified by silica gel column chromatography. (Gradient eluent:petroleum ether:ethyl acetate: from 100:0 to 60:40) resulting in compound 37 (1.78 g). Method B; Rt: 1.12 min. m/z: 368.1 (M+H)$^+$ Exact mass: 367.1

Compound 37 (1.58 g, 4.3 mmol) in POCl$_3$ (7.9 mL, 86 mmol) was stirred for 2 hours at 120° C. The reaction mixture was concentrated to dryness. The obtained residue was dissolved in dichloromethane (50 mL). The organic layer was washed with saturated aqueous NaHCO$_3$ (3×20 mL) and brine and dried over Na$_2$SO$_4$. The solvent was removed in vacuo. The obtained residue was purified by silica gel column chromatography (gradient eluent:petroleum ether:ethyl acetate: from 100:0 to 70:30), resulting in compound 38 (1.1 g). Method B; Rt: 1.19 min. m/z: 386.1 (M+H)$^+$ Exact mass: 385.1

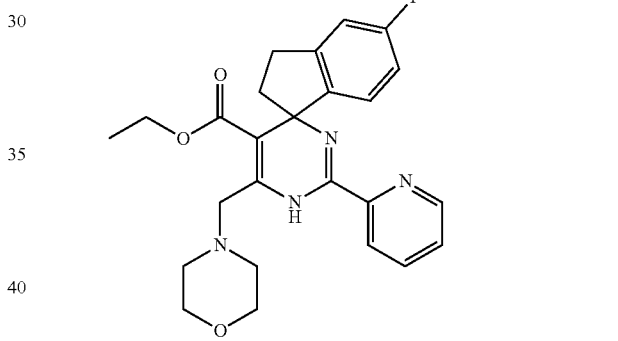

Compound 39

A mixture of compound 38 (0.1 g, 0.26 mmol), Potassium trifluoro(morpholino-methyl)borate (0.11 g, 0.52 mmol), Pd(OAc)$_2$ (0.006 g, 0.026 mmol), butyldi-1-adamantylphosphine (0.015 g, 0.042 mmol) and Cs$_2$CO$_3$ (0.51 g, 1.55 mmol) in DME (1.4 mL) and H$_2$O (0.14 mL) was stirred under microwave irradiation for 20 minutes at 140° C. under N$_2$. Water (5 mL) and dichloromethane (5 mL) were added. The organic layer was separated and washed with water (2×5 mL). The organic layer was washed with 1N HCl (5 mL). The aqueous layer was washed with dichloromethane (2×5 mL) and basified with NaHCO$_3$ to pH=7-8. The mixture was extracted with dichloromethane (15 mL). The organic layer was washed with brine and dried over Na$_2$SO$_4$. The solvent was removed in vacuo resulting in compound 39 (0.1 g). Method C; Rt: 3.24 min. m/z: 451.2 (M+H)$^+$ Exact mass: 450.2

$^1$H NMR (400 MHz, CHLOROFORM-d) ppm 9.99 (br. s, 1H) 8.49-8.69 (m, 1H) 8.16 (dt, J=8.0, 1.0 Hz, 1H) 7.71 (td, J=7.8, 1.8 Hz, 1H) 7.35 (ddd, J=7.5, 5.0, 1.1 Hz, 1H) 7.04 (dd, J=8.3, 5.5 Hz, 1H) 6.86-6.96 (m, 1H) 6.73-6.86 (m, 1H) 3.88 (q, J=7.3 Hz, 2H) 3.80-3.85 (m, 4H) 3.81 (d, J=16.6 Hz, 1H) 3.71 (d, J=16.6 Hz, 1H) 3.16-3.27 (m, 1H) 2.92-3.03 (m, 1H) 2.64-2.71 (m, 1H) 2.57-2.63 (m, 4H) 2.28-2.38 (m, 1H) 0.89 (t, J=7.2 Hz, 3H)

Compound 40

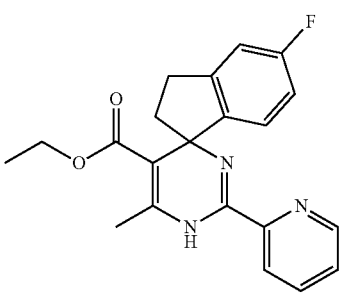

A mixture of compound 38 (0.2 g, 0.52 mmol), 2,4,6-trimethyl-1,3,5,2,4,6-trioxatriborinane (0.13 g, 1.04 mmol), PEPPSI™-IPr catalyst (0.035 g, 0.052 mmol) and K$_2$CO$_3$ (0.21 g, 1.55 mmol) in dry THF (4 mL) was stirred under microwave irradiation for 5 minutes at 150° C. under N$_2$ atmosphere. The mixture was filtered. The filtrate was concentrated to dryness and purified by thin layer chromatography (eluent:petroleum ether:ethyl acetate=2:1). The obtained product was further purified by high-performance liquid chromatography (C18, eluent: CH$_3$CN/H$_2$O from 15/85 to 45/55 with 0.1% HCl as buffer). The pure fractions were collected and the mixture was evaporated to dryness, resulting in compound 40 (as a HCl salt) (60 mg). Method C; Rt: 3.05 min. m/z: 366.1 (M+H)$^+$ Exact mass: 365.2

Compound 41

POPd (126 mg, 0.250 mmol) and potassium carbonate (2.08 g, 15.0 mmol) were added to a nitrogen purged stirring mixture of diethyl 2-(1-chloroethylidene)malonate (1.10 g, 5.00 mmol), 2-chloro-4-fluorophenylboronic acid (1.57 g, 9.00 mmol), tetrahydrofurane (10.0 mL) and water (1.0 mL) in a microwave tube. The reaction mixture was sealed with a silicon septum and subjected to microwave irradiation for 60 minutes at 100° C. The reaction was repeated in total 5 times, the separated reaction vessels were allowed to cool to room temperature, the reaction mixtures were combined, diluted with heptane (600 mL) and washed with sodium carbonate (2×100 mL), water (1×50 mL) and Brine (50 mL). After drying (MgSO$_4$) the solvents were removed in vacuo. The residue was purified using silica gel column chromatography by gradient elution with 0 to 6% ethyl acetate in heptane resulting in diethyl 2-(1-(2-chloro-4-fluoro-phenyl)ethylidene)malonate as a liquid (860 mg). A pressure tube with a magnetic stirring bar, pyridine-2-carboximidamide hydrochloride (0.594 g, 3.77 mmol) and N-Methyl-2-Pyrrolidone (10 mL) under a nitrogen atmosphere was cooled to 0° C. Potassium tert-butoxide (0.564 g, 5.03 mmol) was added under a nitrogen atmosphere and the reaction mixture was stirred for 15 minutes at room temperature. Diethyl 2-(1-(2-chloro-4-fluorophenyl)ethylidene)malonate (860 mg, 2.51 mmol) in N-Methyl-2-Pyrrolidone (5 mL) was added and the pressure tube was heated and stirred in an oil bath at 88° C. for 44 hours. After cooling to room temperature; the reaction mixture was poured into water (200 mL) and hydrochloric acid (1N, 4 mL) was added. The mixture was stirred for 5 minutes and extracted with diisopropyl ether (3×100 mL). The combined organic extracts were dried (Na$_2$SO$_4$) and concentrated under reduced pressure. The obtained residue was purified using silica gel column chromatography by gradient elution with 30 to 100%. dichloromethane in heptanes. The desired fractions were concentrated in vacuo, resulting in ethyl 4-(2-chloro-4-fluorophenyl)-4-methyl-6-oxo-2-(pyridin-2-yl)-1,4,5,6-tetrahydropyrimidine-5-carboxylate (311 mg). Under a nitrogen atmosphere, ethyl 4-(2-chloro-4-fluorophenyl)-4-methyl-6-oxo-2-(pyridin-2-yl)-1,4,5,6-tetrahydropyrimidine-5-carboxylate (311 mg, 0.798 mmol) and phosphorous oxychloride (1.48 mL, 16.0 mmol) where stirred and heated at 110° C. for 30 minutes. After cooling, the reaction mixture was concentrated to dryness in vacuo. The obtained residue was dissolved in dichloromethane (50 mL), washed with saturated aqueous sodium bicarbonate (2×20 mL) and brine (20 mL). After drying (Na$_2$SO$_4$) the volatiles were removed in vacuo resulting in a residue (260 mg) which was used as such in the next step. A microwave (10 mL) tube was loaded with a stirring bar, potassium (morpholin-4-yl)methyltrifluoroborate (128 mg, 0.588 mmol), the above obtained residue (260 mg, 0.452 mmol), water (245 μL, 13.6 mmol) and 1,2-dimethoxyethane (2.35 mL) and purged with nitrogen for 10 minutes. Under nitrogen atmosphere Bis(tri-tert-butylphosphine) palladium (0) (23.1 mg, 0.0452 mmol) and potassium carbonate (281 mg, 2.04 mmol) were added and the reaction mixture was stirred under microwave irradiation at 140° C. for 10 minutes. After cooling, nitrogen gas was bubbled through the reaction mixture and more butyldi-1-adamantylphosphine (24.3 mg, 0.0678 mmol) and palladium (II) acetate (10.2 mg, 0.0452 mmol) were added. The reaction mixture was stirred under microwave irradiation at 140° C. for 10 minutes under a nitrogen atmosphere. The water layer was extracted with dichloromethane, the organic layers were combined and washed with sodium carbonate, dried (Na$_2$SO$_4$) and evaporated to dryness. The residue was purified using silica gel column chromatography by gradient elution with 5% to 50% ethyl acetate in heptane resulting in compound 41 (73 mg). Method D; Rt: 1.22 min. m/z: 473.1 (M+H)$^+$ Exact mass: 472.2 $^1$H NMR (400 MHz, CHLOROFORM-d) ppm 0.92 (t, J=7.0 Hz, 3H), 1.92 (s, 3H), 2.53-2.67 (m, 4H), 3.67 (d, J=16.8 Hz, 1H), 3.77-3.90 (m, 7H), 6.97 (td, J=8.4, 2.8 Hz, 1H), 7.04 (dd, J=8.8, 2.8 Hz, 1H), 7.36 (ddd, J=7.5, 5.0, 1.1 Hz, 1H), 7.61 (dd, J=9.0, 6.3 Hz, 1H), 7.72 (td, J=7.8, 1.8 Hz, 1H), 8.13 (br. d, J=7.8 Hz, 1H), 8.61 (br. d, J=4.5 Hz, 1H), 10.19 (s, 1H)

Compound 42

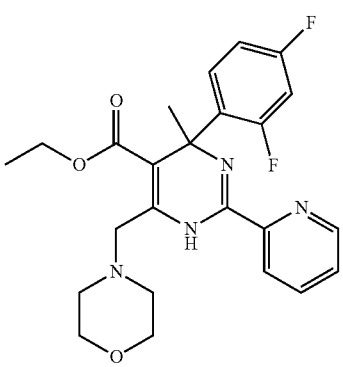

POPd (582 mg, 1.16 mmol) was added to a nitrogen purged stirred mixture of diethyl 2-(1-chloroethylidene)malonate (3.00 g, 13.6 mmol), 2,4-difluorophenylboronic acid (3.22 g, 20.4 mmol), potassium carbonate (5.64 g, 40.8 mmol), tetrahydrofuran (16.0 mL) and water (3.00 mL) in a microwave tube. The reaction mixture was sealed and subjected to microwave irradiation for 1 hour at 100° C. After cooling to room temperature the reaction mixture was diluted with dichloromethane (150 mL), washed with water, saturated aqueous sodium carbonate and water (3×40 mL), dried (Na$_2$SO$_4$) and evaporated to dryness. The residue was purified using silica gel column chromatography by gradient elution with 0 to 15% ethyl acetate in heptane resulting in diethyl 2-(1-(2,4-difluorophenyl)ethylidene)malonate as an oil (1.06 g).

Under a nitrogen atmosphere, a pressure tube was charged with a magnetic stirring bar, pyridine-2-carboximidamide hydrochloride (268 mg, 1.70 mmol), N,N-Dimethylformamide (13.2 mL), potassium tert-butoxide (382 mg, 3.41 mmol) and diethyl 2-(1-(2,4-difluorophenyl)ethylidene)malonate (508 mg, 1.70 mmol). The reaction mixture was sealed and stirred at 60° C. for 45 hours. After cooling to room temperature, the reaction mixture was poured into ice water (200 mL) and the resulting emulsion was neutralized (pH=7) using hydrochloric acid (1N). The mixture was extracted with dichloromethane. The combined organic extracts were dried (Na$_2$SO$_4$) and concentrated under reduced pressure. N,N-Dimethylformamide was co evaporated using toluene and the resulting yellow oil was purified using silica gel column chromatography with ethyl acetate in heptane in a gradient from 10 to 40%. The desired fractions were concentrated in vacuo yielding ethyl 4-(2,4-difluorophenyl)-4-methyl-6-oxo-2-(pyridin-2-yl)-1,4,5,6-tetrahydropyrimidine-5-carboxylate (203 mg). Under a nitrogen atmosphere, a tube was charged with a stirring bar, ethyl 4-(2,4-difluorophenyl)-4-methyl-6-oxo-2-(pyridin-2-yl)-1,4,5,6-tetrahydropyrimidine-5-carboxylate (137 mg, 0.367 mmol) and phosphorous oxychloride (0.509 mL, 5.48 mmol). The mixture was stirred and heated at reflux for 30 minutes. After cooling to room temperature, the reaction mixture was concentrated to dryness. The obtained residue was dissolved in dichloromethane and washed with saturated aqueous sodium bicarbonate (3×10 mL), dried (isolute HM-N) and evaporated to resulting in ethyl 6-chloro-4-(2,4-difluorophenyl)-4-methyl-2-(pyridin-2-yl)-1,4-dihydropyrimidine-5-carboxylate (154 mg) as a yellow powder which was used as such in the next step.

A 10 mL microwave tube was loaded with a stirring bar, potassium (morpholin-4-yl)-methyltrifluoroborate (381 mg, 1.84 mmol), ethyl 6-chloro-4-(2,4-difluorophenyl)-4-methyl-2-(pyridin-2-yl)-1,4-dihydropyrimidine-5-carboxylate (154 mg, 0.354 mmol), cesium carbonate (1.38 g, 4.25 mmol), distilled water (300 μL) and toluene (3 mL). Nitrogen gas was bubbled through for 5 minute and under a nitrogen atmosphere palladium(II) acetate (16.0 mg, 0.0708 mmol) and butyldi-1-adamantylphosphine (40.6 mg, 0.113 mmol) were added. The reaction mixture was stirred at 120° C. for 18 hours under a nitrogen atmosphere. The reaction mixture was cooled to room temperature and diluted with dichloromethane (50 mL). The mixture was washed with saturated aqueous sodium carbonate (2×5 mL) and water (5 mL). The organic layer was dried over an HM-N cartridge and concentrated to dryness to afford a brown sticky residue. This residue was purified using silica gel column chromatography by gradient elution with 0 to 2% methanol (7 N ammonia) in dichloromethane and again by gradient elution with 0 to 2% methanol in dichloromethane resulting in compound 42 (81 mg) after drying overnight in vacuum oven at 50° C. Method A;

Rt: 1.23 min. m/z: 457.4 (M+H)$^+$ Exact mass: 456.2; $^1$H NMR (400 MHz, CHLOROFORM-d): ppm 1.00 (t, J=7.2 Hz, 3H), 1.91 (s, 3H), 2.54-2.65 (m, 4H), 3.65 (d, J=16.8 Hz, 1H), 3.77-3.85 (m, 5H), 3.92 (m, 2H), 6.69 (ddd, J=11.7, 9.0, 2.6 Hz, 1H), 6.78-6.86 (m, 1H), 7.36 (ddd, J=7.5, 4.8, 1.3 Hz, 1H), 7.44 (td, J=9.0, 6.5 Hz, 1H), 7.72 (td, J=7.7, 1.6 Hz, 1H), 8.14 (dt, J=7.8, 1.1 Hz, 1H), 8.60 (ddd, J=4.8, 1.5, 0.8 Hz, 1H), 10.10 (br. s, 1H)

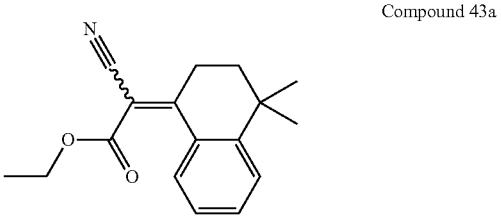 [SMILES: CCOC(=O)C(C#N)=C1CCC(C)(C)c2ccccc21]

Compound 43a

Procedure C:

A mixture of HOAc (3.82 mL, 66.74 mmol), 4,4-dimethyl-3,4-dihydro-2H-naphthalen-1-one (5 g, 28.7 mmol), ethyl cyanoacetate (3.37 mL, 31.6 mmol), benzene (19 mL), beta-alanine (0.639 g, 7.17 mmol) was heated at reflux in a Dean Stark apparatus for ~65 hours. The reaction mixture was poured slowly into of H$_2$O (100 mL) containing NaHCO$_3$ (12.6 g) and stirred for 20 minutes. The resulting water layer was extracted with toluene. The combined extracts were washed with brine, dried on MgSO$_4$, filtered and concentrated in vacuo resulting in compound 43a as an oil which was used as such.

Other compounds obtained by using similar conditions as described in procedure C:

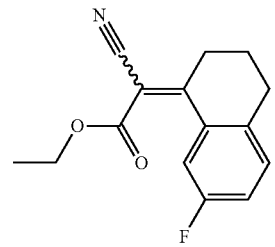 [SMILES: CCOC(=O)C(C#N)=C1CCCc2ccc(F)cc21]

Compound 43b using 7-fluoro-3,4-dihydronaphthalen-1 (2H)-one as starting material

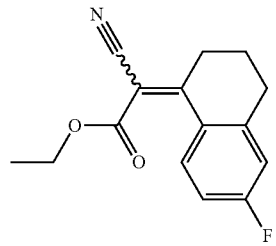 [SMILES: CCOC(=O)C(C#N)=C1CCCc2cc(F)ccc21]

Compound 43c using 6-fluoro-3,4-dihydronaphthalen-1 (2H)-one as starting material

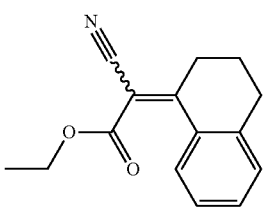 [SMILES: CCOC(=O)C(C#N)=C1CCCc2ccccc21]

Compound 43d using 3,4-dihydronaphthalen-1(2H)-one as starting material and 17 hours reaction time.

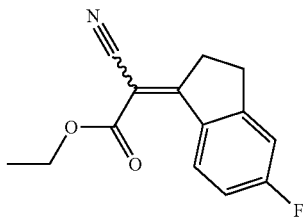 [SMILES: CCOC(=O)C(C#N)=C1CCc2cc(F)ccc21]

Compound 43e using 5-fluoro-2,3-dihydro-1H-inden-1-one as starting material

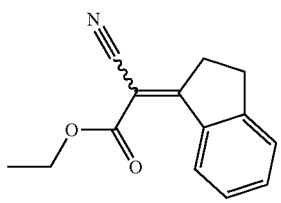 [SMILES: CCOC(=O)C(C#N)=C1CCc2ccccc21]

Compound 43f using 2,3-dihydro-1H-inden-1-one as starting material

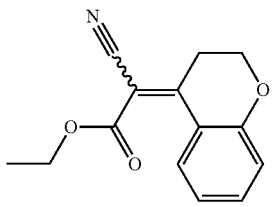 [SMILES: CCOC(=O)C(C#N)=C1CCOc2ccccc21]

Compound 43g using chroman-4-one as starting material and 20 hours reaction time Compound 44

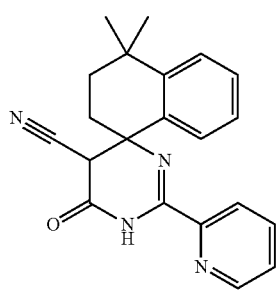 [SMILES: CC1(C)CCC2(N=C(c3ccccn3)NC(Cl)=C2C#N)c2ccccc21]

Compound 43a (crude mixture, 3 g, 11.14 mmol), pyridine-2-carboximidamide hydrochloride (1.93 g, 12.25 mmol), Na$_2$CO$_3$ (1.77 g, 16.7 mmol) and DMF (13.6 mL) were heated in a pressure tube in an oil bath at 75° C. for 1 hour. The resulting reaction mixture was cooled to room temperature and concentrated in vacuo. The resulting residue was taken up in water-CH$_2$Cl$_2$ (150 mL/150 mL) and the water layer was extracted with CH$_2$Cl$_2$ (2×100 mL). The combined extracts were washed with brine, dried (MgSO$_4$), filtered and concentrated in vacuo. The obtained residue was chromatographed by silica gel column chromatography (isocratic CH$_2$Cl$_2$)

The desired fractions were concentrated in vacuo yielding compound 44, which was used as such. Method A; Rt: 1.09 min. m/z: 345.4 (M+H)$^+$ Exact mass: 344.2;

Compound 45

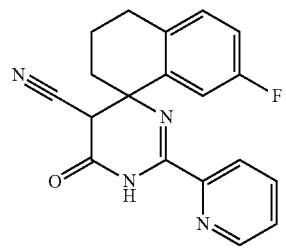

Procedure D:

Compound 43b (9.4 g, 36.3 mmol), pyridine-2-carboximidamide hydrochloride (6.86 g, 43.5 mmol), KOAc (5.34 g, 54.4 mmol) and DMF (87 mL) were heated in a pressure tube to 110° C. for 1 hour. The resulting reaction mixture was cooled to room temperature and concentrated in vacuo. The residue was taken up in water-CH$_2$Cl$_2$ (150 mL-150 mL). The water layer was extracted twice (CH$_2$Cl$_2$, 2×100 mL) and the combined extracts were washed with brine, dried (MgSO$_4$), filtered and concentrated in vacuo yielding a brown oil. This oil was purified by silicagel column chromatography (gradient elution:EtOAc-heptane 1:9 to 3:7) yielding compound 45 (4.7 g) which was used as such. Method E; Rt: 0.95 min. m/z: 335.1 (M+H)$^+$ Exact mass: 334.1;

Compound 46

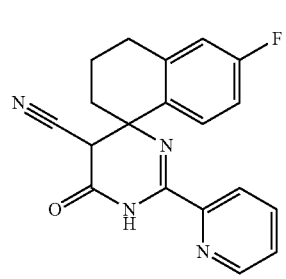

Prepared according to procedure D, starting from compound 43c, purification by silicagel column chromatography (gradient elution: CH$_2$Cl$_2$-MeOH 100:0→98:2).

Method A; Rt: 0.99 min. m/z: 335.3 (M+H)$^+$ Exact mass: 334.1;

Compound 47

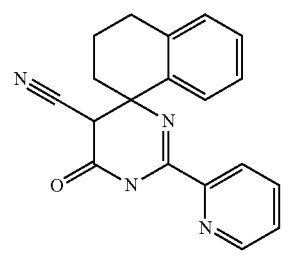

Prepared according to procedure D, starting from compound 43d

Method A; Rt: 0.97 min. m/z: 317.3 (M+H)⁺ Exact mass: 316.1;

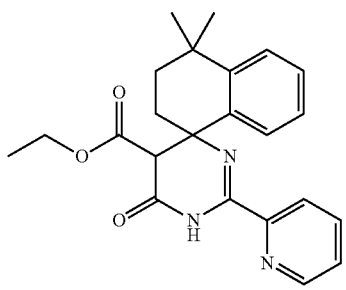

Compound 48

Procedure E:

EtOH (30 mL) was saturated with HCl (gas bubbled through) for 90 minutes. Compound 44 (0.5 g, 1.45 mmol) was added and the reaction mixture was stirred for 20 hours in an oil bath at 60° C. The resulting reaction mixture was concentrated in vacuo and taken up in CH$_2$Cl$_2$ (50 mL)/H$_2$O (50 mL). The layers were separated and the water layer was extracted with CH$_2$Cl$_2$ (2×50 mL). The combined extracts were dried (MgSO$_4$), filtered and concentrated in vacuo yielding compound 48 (560 mg) as an oil which was used as such. Method A; Rt: 1.24 min. m/z: 392.5 (M+H)⁺ Exact mass: 391.2;

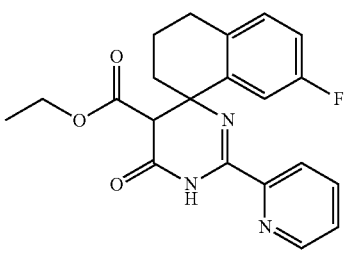

Compound 49

Compound 45 (1 g, 2.991 mmol) in EtOH (10 mL) in a pressure tube was cooled in an ice bath under a gentle flow of nitrogen. The mixture was treated dropwise with concentrated H$_2$SO$_4$ (3.2 mL, 59.8 mmol) and the vial was capped. The resulting reaction mixture was heated in an oil bath at 40° C. for 20 hour. The resulting reaction mixture was cooled to room temperature and H$_2$O (20 mL) was added. NaHCO$_3$ (10.05 g, 119.6 mmol) was added portion wise under stirring. The water layer was extracted (3×100 mL) and the combined extracts were dried (MgSO$_4$), filtered and concentrated in vacuo. The obtained residue was chromatographed using silica gel column chromatography (isocracic CH$_2$Cl$_2$-MeOH 98:2). The desired fractions were concentrated in vacuo yielding compound 49, which was used as such.

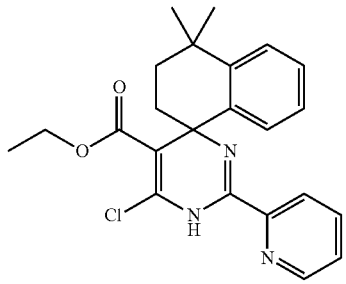

Compound 50

Procedure F:

Compound 48 (560 mg) was treated with POCl$_3$ (5 mL, 53.8 mmol) and this was stirred in an oil bath at 105-110° C. for 1 hour. The resulting reaction mixture was concentrated in vacuo. The residue was treated with ice-water and then extracted with CH$_2$Cl$_2$ (3×50 mL). The combined extracts were dried on MgSO$_4$ and concentrated in vacuo. The residue was purified by silica gel column chromatography (isocratic CH$_2$Cl$_2$) yielding compound 50 (359 mg) as a yellow solid which was used as such. Method E; Rt: 1.34 min. m/z: 410.2 (M+H)⁺ Exact mass: 409.2;

Prepared similar to described in Procedure F:

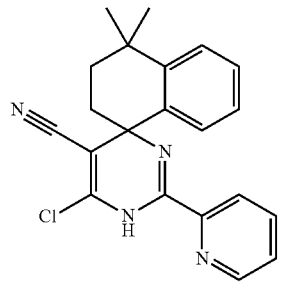

Compound 51 starting from compound 44. Method A; Rt: 1.28 min. m/z: 363.4 (M+H)⁺ Exact mass: 362.1;

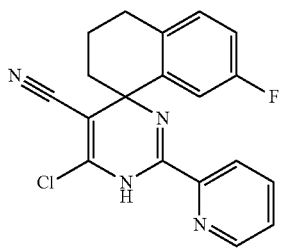 [SMILES: N#CC1=C(Cl)NC(c2ccccn2)=NC12CCCc1ccc(F)cc12]

Compound 52 starting form compound 45. This compound was used as such without column chromatrography. Method A; Rt: 1.17 min. m/z: 353.3 (M+H)⁺ Exact mass: 352.1;

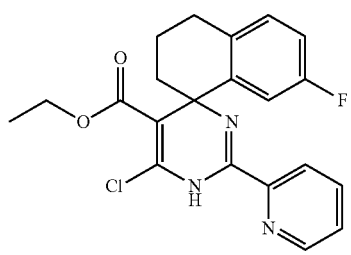 [SMILES: CCOC(=O)C1=C(Cl)NC(c2ccccn2)=NC12CCCc1ccc(F)cc12]

Compound 53 starting form compound 49. Method D; Rt: 1.29 min. m/z: 400.0 (M+H)⁺ Exact mass: 399.1;

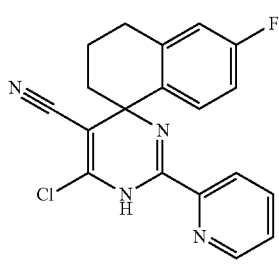 [SMILES: N#CC1=C(Cl)NC(c2ccccn2)=NC12CCCc1cc(F)ccc12]

Compound 54 starting from compound 46.

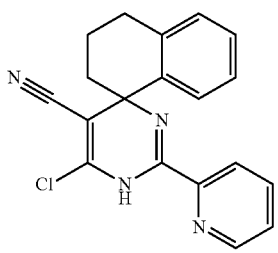 [SMILES: N#CC1=C(Cl)NC(c2ccccn2)=NC12CCCc1ccccc12]

Compound 55 starting from compound 47. Stirred at 120° C. instead of 105° C. for 1 hour, compound used as such, without silica gel column chromatography. Method A; Rt: 1.17 min. m/z: 335.3 (M+H)⁺ Exact mass: 334.1;

Compound 56

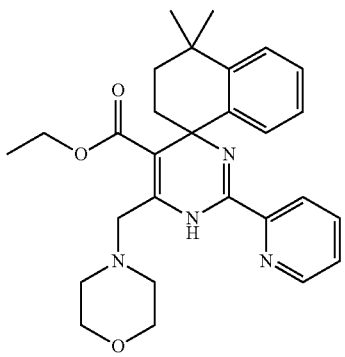

Procedure G:
A microwave vial was charged with compound 50 (0.1 g, 0.244 mmol), Cs$_2$CO$_3$ (0.477 g, 1.464 mmol), potassium (morpholin-4-yl)methyltrifluoroborate (0.101 g, 0.488 mmol), water (0.13 mL, 7.32 mmol) and DME (1.3 mL, 12.2 mmol). This mixture was purged with nitrogen for 5 minutes. Then palladium(II) acetate (0.0055 g, 0.0244 mmol) and butyldi-1-adamantylphosphine (0.014 g, 0.039 mmol) was added and the reaction mixture was purged for another 2 minutes. The vial was capped and stirred under microwave irradiation at 140° C. for 30 minutes. The resulting reaction mixture was concentrated in vacuo and the residue was taken up in H$_2$O—CH$_2$Cl$_2$ (50 mL/50 mL) and the water layer was further extracted with CH$_2$Cl$_2$ (2×50 mL). The combined extracts were dried (MgSO$_4$) and concentrated in vacuo. The residue was purified by silica gel column chromatography (gradient elution EtOAc-heptane 10:90→50:50). The desired fractions were concentrated in vacuo yielding compound 56 as a yellow powder (44.7 mg). Method A; Rt: 1.34 min. m/z: 475.3 (M+H)⁺ Exact mass: 474.3;

¹H NMR (600 MHz, CHLOROFORM-d): ppm 0.70 (t, J=7.1 Hz, 3H), 1.35 (s, 3H), 1.39-1.43 (m, 1H), 1.44 (s, 3H), 1.90-1.99 (m, 1H), 2.45-2.55 (m, 2H), 2.57-2.68 (m, 4H), 3.68-3.74 (m, 1H), 3.71 (d, J=16.5 Hz, 1H), 3.83 (t, J=4.6 Hz, 4H), 3.85-3.91 (m, 1H), 3.88 (d, J=16.4 Hz, 1H), 7.05 (ddd, J=7.6, 7.2, 1.4 Hz, 1H), 7.13 (ddd, J=7.9, 7.1, 1.5 Hz, 1H), 7.17 (dd, J=7.8, 1.5 Hz, 1H), 7.32 (ddd, J=7.5, 4.8, 1.2 Hz, 1H), 7.35 (dd, J=7.9, 1.4 Hz, 1H), 7.68 (td, J=7.7, 1.7 Hz, 1H), 8.18 (dt, J=8.0, 1.1 Hz, 1H), 8.57 (ddd, J=4.8, 1.7, 0.9 Hz, 1H), 10.01 (s, 1H)

Prepared according to procedure G:

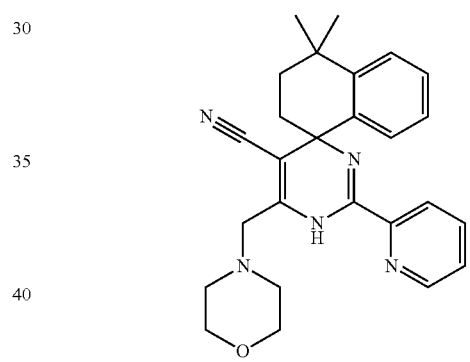

Compound 57 starting from compound 51. Method F; Rt: 6.63 min. m/z: 428.2 (M+H)⁺ Exact mass: 427.2;

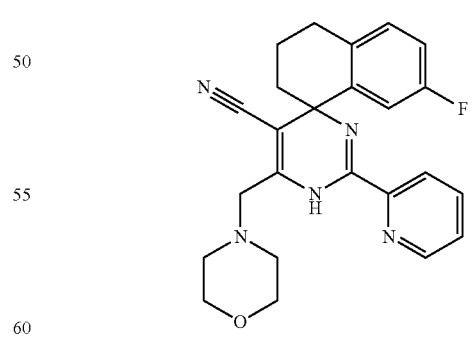

Compound 58 starting from compound 52

Purified using silica gel column chromatography with CH$_2$Cl$_2$-MeOH 100:0→98:2), Triturated with heptane/Diisopropylether. Method A; Rt: 1.20 min. m/z: 418.5 (M+H)⁺ Exact mass: 417.2;

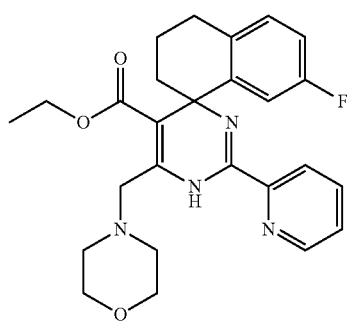 [SMILES: CCOC(=O)C1=C(CN2CCOCC2)NC(c2ccccn2)=NC12CCCc1ccc(F)cc12]

Compound 59 starting form compound 53; ¹H NMR (600 MHz, CHLOROFORM-d) ppm 0.83 (t, J=7.1 Hz, 3H), 1.71-1.78 (m, 1H), 2.02-2.09 (m, 1H), 2.23-2.30 (m, 1H), 2.30-2.36 (m, 1H), 2.56-2.68 (m, 4H), 2.74-2.88 (m, 2H), 3.74 (d, J=16.8 Hz, 1H), 3.80-3.86 (m, 6H), 3.90 (d, J=16.8 Hz, 1H), 6.77 (td, J=8.4, 2.8 Hz, 1H), 6.89 (dd, J=10.3, 2.7 Hz, 1H), 7.03 (dd, J=8.4, 5.8 Hz, 1H), 7.34 (ddd, J=7.5, 4.8, 1.2 Hz, 1H), 7.70 (td, J=7.7, 1.7 Hz, 1H), 8.16 (dt, J=8.0, 1.1 Hz, 1H), 8.58 (ddd, J=4.8, 1.7, 1.0 Hz, 1H), 10.09 (s, 1H); Method A; Rt: 1.38 min. m/z: 465.2 (M+H)⁺ Exact mass: 464.2;

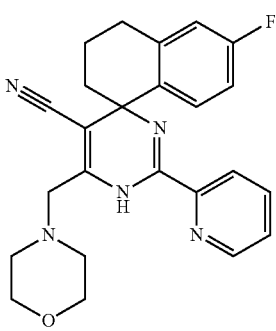 [SMILES: N#CC1=C(CN2CCOCC2)NC(c2ccccn2)=NC12CCCc1cc(F)ccc12]

Compound 60 starting from compound 54

Purified using silica gel column chromatography by gradient elution with EtOAc-heptane 10:90 to 50:50.

¹H NMR (400 MHz, CHLOROFORM-d) ppm 1.93-2.29 (m, 4H), 2.54-2.61 (m, 4H), 2.83-2.95 (m, 2H), 3.52 (d, Jab=15.1 Hz, 1H), 3.56 (d, Jab=15.1 Hz, 1H), 3.77-3.82 (m, 4H), 6.80-6.91 (m, 2H), 7.24 (dd, J=8.7, 5.9 Hz, 1H), 7.37-7.41 (m, 1H), 7.75 (td, J=7.8, 1.5 Hz, 1H), 8.20 (d, J=8.0 Hz, 1H), 8.59 (d, J=4.8 Hz, 1H), 9.70 (s, 1H). Method A; Rt: 1.19 min. m/z: 418.5 (M+H)⁺ Exact mass: 417.2;

The racemic mixture was separated in enantiomers 60a and 60b by preparative SFC on Chiralpak Diacel AD (30×250 mm). Mobile phase (CO₂, iPrOH with 0.2% iPrNH₂), yielding compound 60a and compound 60b both as yellow powders. SFC: Column: AD-H 250 mm×4.6 mm; Flow: 3 mL/min; Mobile phase: 10% iPrOH (containing 0.2% iPrNH₂) in CO₂, hold 15.00 min, Temperature: 30° C., Rt: Compound 60a: 5.62 min, 60b: 8.72 min

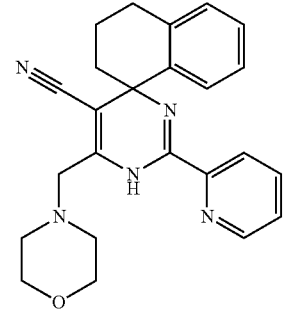 [SMILES: N#CC1=C(CN2CCOCC2)NC(c2ccccn2)=NC12CCCc1ccccc12]

Compound 61 starting from compound 55; Purified using silica gel column chromatography by gradient elution with EtOAc-heptane 10:90 to 50:50. Precipitated from Diisopropylether-CH₃CN.

Method A; Rt: 1.17 min. m/z: 400.5 (M+H)⁺ Exact mass: 399.2;

Compound 62

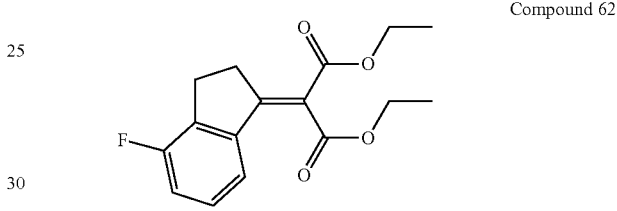

A solution of 4-fluoro-1-indanone (10 g, 66.6 mmol), diethylmalonate (11.734 g, 73.3 mmol) in tetrahydrofurane (278 mL) was cooled to 0° C. under a nitrogen atmosphere. Titanium tetrachloride (140 mL, 140 mmol, 1 M in dichloromethane) was added drop wise followed by pyridine (27.8 mL, 345 mmol). The resulting mixture was stirred overnight at room temperature. After filtration, the filtrate was diluted with ethyl acetate (300 mL). The organic layer was washed with brine (3×200 mL), dried (Na₂SO₄) and evaporated. The residue was purified using silica gel column chromatography with ethyl acetate in heptane in a gradient from 0 to 10%. All desired fractions were combined and evaporated until a volume of ~200 mL was obtained. More heptane was added and the formed orange precipitate was filtered and washed with Heptane. The obtained filtrate was concentrated to dryness in vacuo resulting in compound 62 (8.81 g) as an orange oil which solidified upon standing.

Compound 63

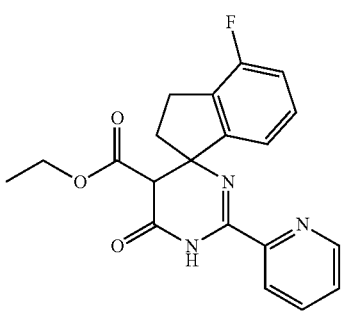

Under a nitrogen atmosphere, a round bottom flak was charged with a magnetic stirring bar, pyridine-2-carboximidamide hydrochloride (9.50 g, 60.3 mmol), N,N-Dimethylformamide (120 mL) and sodium carbonate (12.8 g, 121 mmol). The reaction mixture was stirred for 10 minutes at room temperature. Compound 62 (8.81 g, 30.1 mmol) was added, the reaction mixture was sealed with a rubber septum and heated at 70° C. for 17 hours. After cooling to room temperature, the reaction mixture was poured into ice water (300 mL) and extracted with diisopropyl ether (3×200 mL). The combined organic extracts were dried ($Na_2SO_4$) and concentrated under reduced pressure. The residue was purified using silica gel column chromatography with ethyl acetate in heptane in a gradient from 0 to 100%. The desired fractions were concentrated in vacuo and the residue was purified using silica gel column chromatography with ethyl acetate in heptane 30%. The desired fractions were concentrated in vacuo and the residue was purified using silica gel column chromatography with dichloromethane 100% resulting in compound 63 (430 mg)

Compound 64

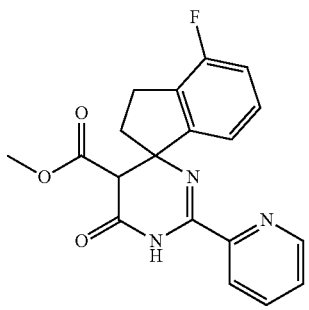

A 100 mL round bottom flask was charged with compound 63 (430 mg, 1.17 mmol), methanol (14.9 mL) and KOtBu (197 mg, 1.76 mmol). The reaction mixture was stirred and heated at 80° C. for 17 hours. The mixture was concentrated in vacuo and the obtained residue was diluted with water and extracted with dichloromethane (3×100 mL). The combined extracts were dried ($Na_2SO_4$), concentrated and dried in resulting in compound 64 (300 mg) as a solid foam which was used as such.

Compound 65

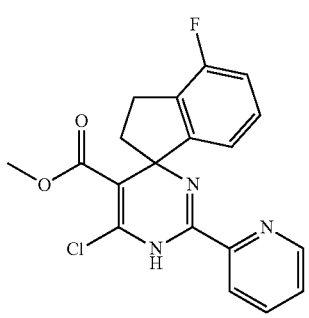

Under a nitrogen atmosphere, a tube was charged with a stirring bar, compound 64 (300 mg, 0.841 mmol) and phosphorous oxychloride (1.17 mL, 12.6 mmol). The mixture was stirred and heated at 120° C. for 30 minutes. After cooling to room temperature the reaction mixture was concentrated to dryness. The obtained residue was dissolved in dichloromethane and washed with saturated aqueous sodium bicarbonate, dried ($Na_2SO_4$) and evaporated to dryness in vacuo, resulting in compound 65 (311 mg) as a yellow brown foam which was used as such in the next step.

Compound 66

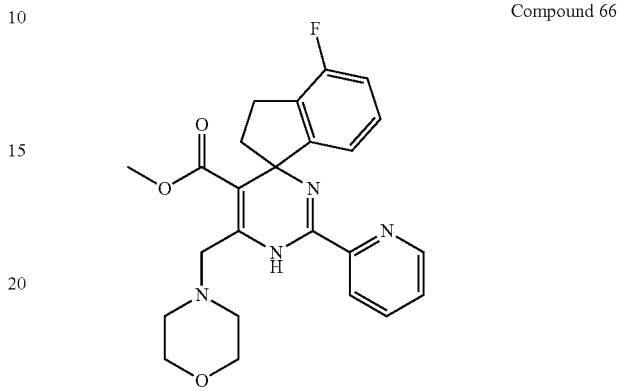

Enantiomers of racemic compound 66: Compound 66a and Compound 66b

A 10 mL microwave tube was loaded with a stirring bar, (morpholin-4-yl)methyltrifluoroborate internal salt (287 mg, 1.61 mmol), compound 65 (300 mg, 0.807 mmol), cesium carbonate (1.57 g, 4.84 mmol), water (0.44 µL) and 1,2-dimethoxyethane (4 mL) and nitrogen gas was bubbled through for 10 minutes. Under a nitrogen atmosphere, palladium (II) acetate (18.3 mg, 0.0807 mmol) and butyldi-1-adamantylphosphine (46.3 mg, 0.129 mmol) were added together and the reaction mixture was stirred at 140° C. in a microwave oven. The reaction mixture was cooled to room temperature. The water layer was extracted with dichloromethane and the organic layers were combined and washed with saturated aqueous sodium carbonate (2×5 mL) and water (5 mL). The organic layer was dried ($Na_2SO_4$) and concentrated to dryness. The residue was purified using silica gel column chromatography with ethyl acetate in heptane in a gradient from 5 to 100% resulting in compound 66 (250 mg) Compound 66 (200 mg) was further purified by Prep SFC on (Chiralcel Diacel OJ 20×250 mm). Mobile phase ($CO_2$, methanol with 0.2% $iPrNH_2$), the desired fractions were collected, evaporated, dissolved in methanol and evaporated again, yielding compound 66a (70 mg) and compound 66b (80 mg) after drying overnight in a vacuum oven at 50° C.

Method A; Rt: 1.23 min. m/z: 437.5 $(M+H)^+$ Exact mass: 436.2;

$^1$H NMR (400 MHz, CHLOROFORM-d) ppm 2.35 (ddd, J=13.1, 9.1, 3.9 Hz, 1H), 2.56-2.68 (m, 5H), 2.96-3.12 (m, 1H), 3.14-3.32 (m, 1H), 3.42 (s, 3H), 3.71 (d, J=16.8 Hz, 1H), 3.79 (d, J=16.8 Hz, 1H), 3.83 (t, J=4.5 Hz, 4H), 6.80-6.93 (m, 2H), 7.12 (td, J=7.8, 5.0 Hz, 1H), 7.34 (ddd, J=7.4, 4.9, 1.0 Hz, 1H), 7.70 (td, J=7.7, 1.6 Hz, 1H), 8.15 (dt, J=8.0, 1.0 Hz, 1H), 8.58 (br. d, J=4.3 Hz, 1H), 10.03 (br. s., 1H); SFC: Column: OJ-H 250 mm×4.6 mm; Flow: 3 mL/min; Mobile phase: 5% EtOH (containing 0.2% $iPrNH_2$) in $CO_2$, hold 15.00 min, Temperature: 30° C., Rt: Compound 66a: 5.26 min, 66b: 8.34 min Compound 67

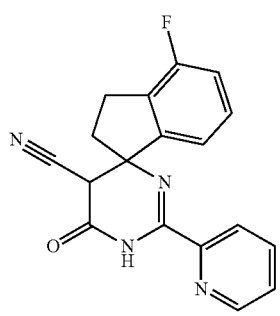

Starting from Compound 43e using procedure D, using Na₂CO₃ instead of KOAc, heating at 70° C. for 1 hour instead of 110° C. for 1 hour. Purification was performed using silica gel column chromatography with CH₂Cl₂ as eluent.

Compound 68

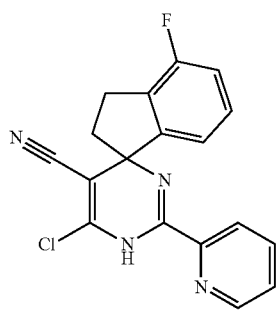

Prepared from compound 67 using procedure F, heating 1.5 hours at 100° C.

Compound 69

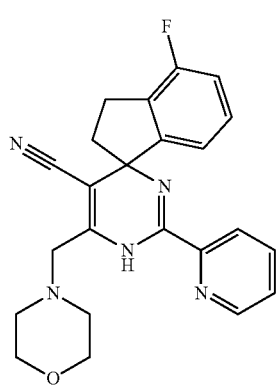

Prepared according to procedure G. The compound was purified using silica gel column chromatography (gradient elution:CH₂Cl₂-MeOH 100:0 to 98:2).
Method A; Rt: 1.14 min. m/z: 404.2 (M+H)⁺ Exact mass: 403.2;
$^1$H NMR (400 MHz, CHLOROFORM-d) ppm 2.45 (ddd, J=13.2, 8.5, 5.8 Hz, 1H), 2.50-2.67 (m, 5H), 3.04-3.22 (m, 2H), 3.52 (s, 2H), 3.79 (t, J=4.8 Hz, 4H), 6.88 (td, J=8.7, 2.3 Hz, 1H), 6.95 (dd, J=8.8, 2.3 Hz, 1H), 7.10 (dd, J=8.4, 5.1 Hz, 1H), 7.39 (ddd, J=7.5, 4.8, 1.0 Hz, 1H), 7.75 (td, J=7.8, 1.8 Hz, 1H), 8.19 (d, J=7.8 Hz, 1H), 8.57-8.62 (m, 1H), 9.67 (br. s., 1H)

Compound 70

Prepared according to procedure E starting from compound 44, using MeOH instead of EtOH. The obtained residue was further used without purification.

Compound 71

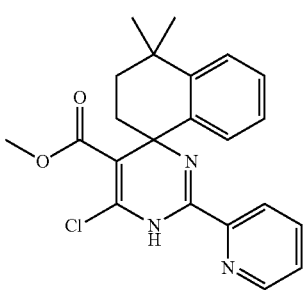

Prepared according to procedure F starting from compound 70 at 110° C. for 1 hour. Method A; Rt: 1.33 min. m/z: 396.2 (M+H)⁺ Exact mass: 395.1

Compound 72

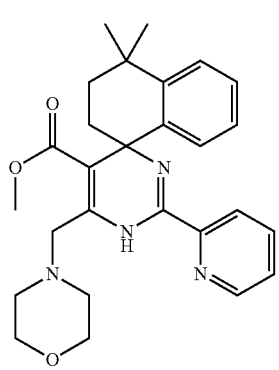

Prepared according to procedure G starting from compound 71, purified by silica gel column chromatography using gradient EtOAc-Heptane 0:100 to 50:50 elution. Method A; Rt: 1.39 min. m/z: 461.2 (M+H)⁺ Exact mass: 460.3; $^1$H NMR (400 MHz, CHLOROFORM-d) ppm 1.34 (s, 3H), 1.40-1.47 (m, 1H), 1.44 (s, 3H), 1.90-1.97 (m, 1H), 2.44-2.57 (m, 2H), 2.57-2.68 (m, 4H), 3.29 (s, 3H), 3.55-3.98 (d, J=16.6 Hz, 1H), 3.80-3.88 (m, 5H), 7.03-7.19 (m, 3H), 7.29-7.39 (m, 2H), 7.68 (td, J=7.8, 1.8 Hz, 1H), 8.17 (dt, J=8.0 Hz, 1.0 Hz, 1H), 8.55-8.58 (m, 1H), 10.00 (s, 1H)

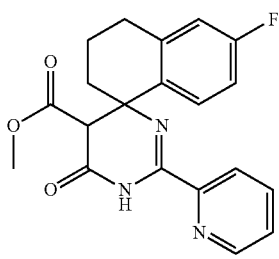

Compound 73

Prepared according to procedure E starting from compound 46, using MeOH instead of EtOH and stirring for 16 hours at 60° C.

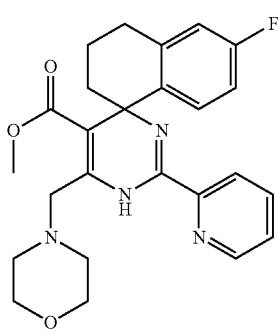

Compound 74

Prepared according to procedure F followed by procedure G, starting from compound 73, purified by silica gel column chromatography using gradient elution with $CH_2Cl_2$-MeOH 100:0 to 98:2). Method A; Rt: 1.27 min. m/z: 451.2 $(M+H)^+$ Exact mass: 450.2; $^1$H NMR (400 MHz, CHLOROFORM-d): ppm 1.72-1.82 (m, 1H), 2.03-2.10 (m, 1H), 2.25-2.38 (m, 2H), 2.59-2.67 (m, 4H), 2.83-2.90 (m, 2H), 3.38 (s, 3H), 3.73 (d, J=16.6 Hz, 1H), 3.80-3.87 (m, 5H), 6.74-6.83 (m, 2H), 7.14-7.19 (m, 1H), 7.32-7.37 (m, 1H), 7.71 (td, J=7.8, 1.5 Hz, 1H), 8.18 (d, J=8.0 Hz, 1H), 8.57-8.61 (m, 1H), 9.99 (s, 1H)

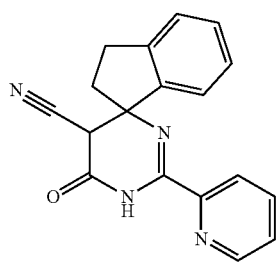

Compound 75

Prepared starting from Compound 43f according to procedure D, using $Na_2CO_3$ instead of KOAc, heating at 75° C. for 2 hours instead of 110° C. for 1 hour. Purification was performed using silica gel column chromatography with $CH_2Cl_2$ as eluent.

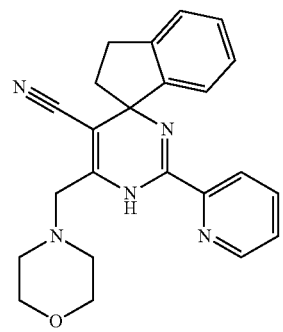

Compound 76

Prepared according to procedure F followed by procedure G, starting from compound 75, purified by silica gel column chromatography using gradient elution with $CH_2Cl_2$-MeOH 100:0 to 98:2). Method A; Rt: 1.11 min. m/z: 386.2 $(M+H)^+$ Exact mass: 385.2; $^1$H NMR (400 MHz, CHLOROFORM-d) ppm 2.37-2.49 (m, 1H), 2.50-2.61 (m, 5H), 3.02-3.25 (m, 2H), 3.52 (s, 2H), 3.79 (t, J=4.8 Hz, 4H), 7.12-7.34 (m, 4H), 7.38 (ddd, J=7.5, 4.8, 1.0 Hz, 1H), 7.74 (td, J=7.8, 1.8 Hz, 1H), 8.20 (d, J=8.0 Hz, 1H), 8.59 (d, J=4.8 Hz, 1H), 9.64 (br. s., 1H)

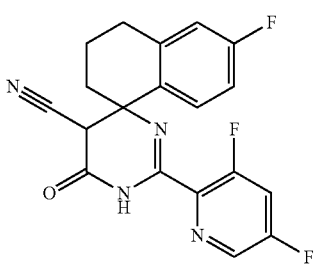

Compound 77

Compound 43c (1000 mg, 3.86 mmol), 3,5-difluoro-2-pyridine carboximidamide (727 mg, 4.63 mmol) and 1,4-dioxane (30 mL) were heated in a pressure tube at 40° C. for 17 hours. The reaction mixture was cooled to room temperature and concentrated in vacuo. The obtained residue was chromatographed by silica gel column chromatography (gradient ethylacetate-heptane 1:9 to 10:0) yielding compound 77 (670 mg) as a white solid which was used as such in the next reaction. Method A; Rt: 0.98 min. m/z: 371.1 $(M+H)^+$ Exact mass: 370.1.

Compound 78

A pressure tube was charged with methanol (25 mL). The mixture was cooled in an ice-water bath. Then, HCl-gas was bubbled through for 30 minutes, while cooling was continued. Compound 77 (670 mg) and water (distilled, 78 µL, 4.3 mmol) were added and the pressure tube was closed and stirred while cooling was continued for 30 minutes. The reaction mixture was stirred in an oil bath at 40° C. over weekend. The reaction mixture was concentrated in vacuo, taken up in CH$_2$Cl$_2$—water (50 mL/50 mL). The water layer was extracted twice more (2×50 mL). The combined extracts were dried on MgSO$_4$, filtered and concentrated in vacuo yielding impure compound 78 as a brown oil which was used as such in the next step.

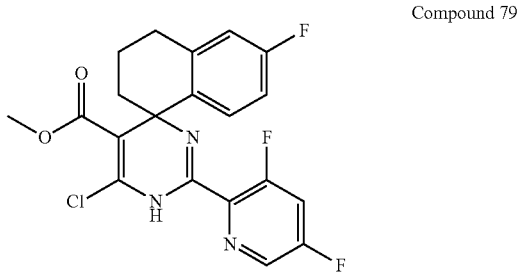 [SMILES: COC(=O)C1=C(Cl)NC(c2ncc(F)cc2F)=NC12CCCc1cc(F)ccc12]

Compound 79

Compound 78 (693 mg) was dissolved in phosphorus oxychloride (5 mL, 53.8 mmol) and this mixture was refluxed for 1 hour in an oil bath at 110° C. The dark brown reaction mixture was concentrated in vacuo, treated with ice-water (50 mL) and the obtained mixture was stirred for 15 minutes. The obtained water layer was extracted using CH$_2$Cl$_2$ (3×50 mL). The combined extracts were dried on MgSO$_4$, filtered and concentrated in vacuo. The dark brown residue was chromatographed by silica gel column chromatography (isocratic CH$_2$Cl$_2$) yielding compound 79 (180 mg) as a yellow solid. Method A; Rt: 1.17 min. m/z: 422.1 (M+H)$^+$ Exact mass: 421.1;

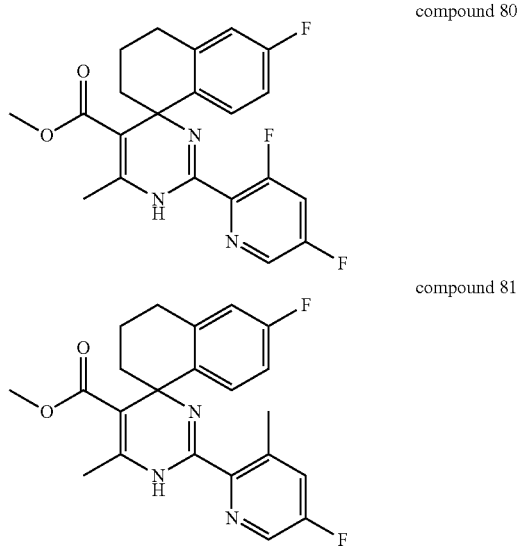

compound 80 compound 81

Compound 79 (0.18 g) was dissolved in DMF (2.6 mL) in a microwave vial and this was purged with nitrogen for 10 minutes. Then tetramethyltin (0.084 mL, 0.61 mmol) was added followed by bis(tri-t-butylphosphine)palladium (0.021 g, 0.041 mmol) and the vial was flushed with nitrogen and capped. The reaction mixture was heated under microwave-irradiation at 140° C. for 10 minutes. The reaction mixture was concentrated in vacuo and co-evaporated with toluene (2×5 mL). The obtained residue was taken up in water-CH$_2$Cl$_2$ (30 mL-30 mL) and the water layer was extracted with CH$_2$Cl$_2$ (2×30 mL). The combined extracts were dried on Na$_2$SO$_4$, filtered and concentrated in vacuo. The obtained crude was purified by preperative HPLC on (RP SunFire Prep C18 OBD-10 µm, 30×150 mm). Mobile phase (0.25% NH$_4$HCO$_3$ solution in water, CH$_3$CN) yielding compound 80 (69 mg) and compound 81 (4.6 mg). Compound 80: Method A; Rt: 1.16 min. m/z: 402.1 (M+H)$^+$ Exact mass: 401.1; $^1$H NMR (600 MHz, CHLOROFORM-d): 70/30 tautomeric mixture (both are described): ppm 1.70-1.78 (m, 1H), 1.80-1.86 (m, 2H), 2.06-2.14 (m, 1H), 2.34 (s, 7H), 2.39 (s, 3H), 2.76-2.81 (m, 2H), 2.81-2.88 (m, 2H), 3.38 (s, 3H), 3.41 (s, 3H), 6.75-6.81 (m, 3H), 6.87 (td, J=8.5, 2.7 Hz, 1H), 7.19-7.23 (m, 1H), 7.24 (ddd, J=10.0, 8.0, 2.3 Hz, 1H), 7.32 (ddd, J=10.3, 8.0, 2.3 Hz, 1H), 7.39 (s, 1H), 7.55 (dd, J=8.7, 5.9 Hz, 1H), 7.89 (s, 1H), 8.24 (d, J=2.2 Hz, 1H), 8.27 (d, J=2.2 Hz, 1H); Compound 81: Method A; Rt: 1.27 min. m/z: 398.2 (M+H)$^+$ Exact mass: 397.2;

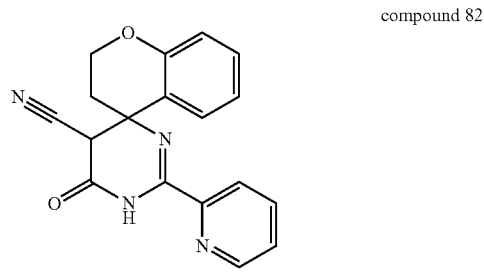 [SMILES: N#CC1C(=O)NC(c2ccccn2)=NC12CCOc1ccccc12]

compound 82

Prepared according to procedure D, heating at 70° C. for 3 hours using sodium bicarbonate (6 equiv) instead of KOAc, starting from compound 43g, purification by silicagel column chromatography (gradient elution: CH$_2$Cl$_2$-MeOH 100:0→98:2). Method A; Rt: 0.86 min. m/z: 319.1 (M+H)$^+$ Exact mass: 318.1;

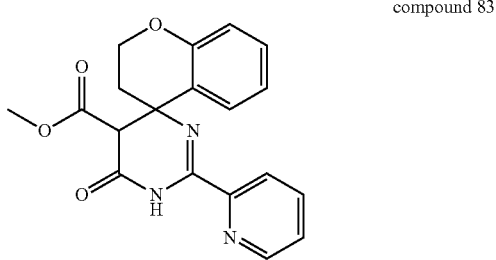 [SMILES: COC(=O)C1C(=O)NC(c2ccccn2)=NC12CCOc1ccccc12]

compound 83

A pressure tube was charged with methanol (30 mL) and cooled in an ice-water bath. Then HCl-gas was bubbled through for 40 minutes while cooling was continued. Compound 82 (1 g) was added to the mixture, the tube was closed and the reaction mixture was stirred for 40 minutes in the ice-water bath. Next, the reaction mixture was stirred in an oil bath at 40° C. overnight. The reaction mixture was cooled to room temperature and concentrated in vacuo. The residue was taken up in H$_2$O—CH$_2$Cl$_2$ (50 mL-50 mL) and the layers were separated. The water layer was extracted using CH$_2$Cl$_2$ (2×100 mL). The combined extracts were dried (MgSO$_4$), filtrated and concentrated in vacuo yielding impure compound 83 (890 mg) as a slightly brown oil which was used as such in the next reaction.

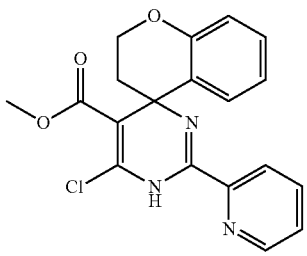

compound 84

Prepared according to procedure F, starting from compound 83. Method A; Rt: 1.12 min. m/z: 370.1 (M+H)+ Exact mass: 369.1;

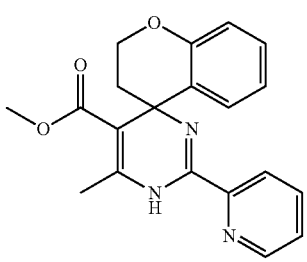

compound 85

Compound 84 (220 mg) was dissolved in N,N-dimethylformamide (3.4 mL) in a microwave vial and this was purged with nitrogen for 10 minutes. Then tetramethyltin (111 μL, 0.8 mmol) was added followed by bis(tri-t-butylphosphine) palladium (82 mg, 0.16 mmol) and the vial was flushed with nitrogen and capped. The reaction mixture was heated under microwave-irradiation at 140° C. for 10 minutes. The reaction mixture was concentrated in vacuo and co-evaporated with toluene (2×5 mL). Then it was taken up in $H_2O$—$CH_2Cl_2$ (30 mL-30 mL) and the water layer was extracted twice more with $CH_2Cl_2$ (2×30 mL). The combined extracts were dried on $Na_2SO_4$, filtrated and concentrated in vacuo. The residue was chromatographed by silica gel column chromatography (gradient $CH_2Cl_2$-methanol 100:0 to 98:2), the fractions containing compound were concentrated and repurified by silica gel column chromatography (gradient Ethylacetate-heptane 0:100-15:85) the fractions containing compound were concentrated and the obtained residue was purified by Prep HPLC on (RP SunFire Prep C18 OBD-10 μm, 30×150 mm). Mobile phase (0.25% $NH_4HCO_3$ solution in water, $CH_3CN$). The obtained residue was co-evaporated with methanol (2×15 mL) and dried vacuo, resulting in compound 85 (5 mg) as a yellow powder. Method E; Rt: 1.05 min. m/z: 350.2 (M+H)+ Exact mass: 349.1;

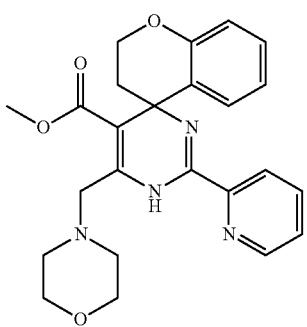

compound 86

Prepared according to procedure G, starting from compound 84, purified by silica gel column chromatography (gradient $CH_2Cl_2$-methanol 100:0 to 98:2) The desired fractions were concentrated in vacuo and the obtained powder was dried in vacuo. Method A; Rt: 1.18 min. m/z: 435.2 (M+H)+ Exact mass: 434.2; $^1$H NMR (400 MHz, CHLOROFORM-d) δ ppm 1.97 (dt, J=13.5, 2.5 Hz, 1H), 2.50-2.68 (m, 4H), 2.73 (ddd, J=13.5, 12.5, 4.0 Hz, 1H), 3.37 (s, 3H), 3.73 (d, J=16.8 Hz, 1H), 3.78-3.93 (m, 5H), 4.24 (ddd, J=10.5, 4.0, 2.5 Hz, 1H), 4.76 (ddd, J=12.5, 10.5, 2.5 Hz, 1H), 6.76-6.91 (m, 2H), 7.08 (ddd, J=8.3, 7.3, 1.5 Hz, 1H), 7.15 (dd, J=7.7, 1.6 Hz, 1H), 7.35 (ddd, J=7.5, 4.8, 1.0 Hz, 1H), 7.71 (td, J=7.8, 1.8 Hz, 1H), 8.19 (m, J=8.0 Hz, 1H), 8.58 (m, J=4.5 Hz, 1H), 10.10 (s, 1H).

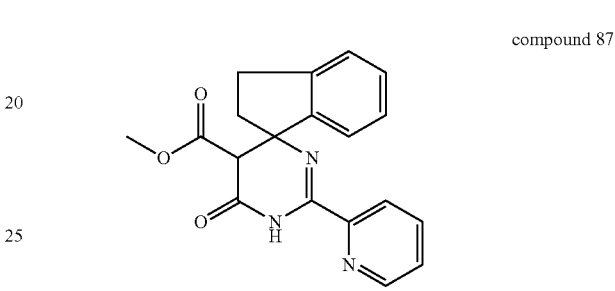

compound 87

A pressure tube was charged with methanol and this was cooled in an ice-water bath. Then HCl gas was bubbled through for 30 minutes while cooling was continued. Then compound 75 (1 g, 3.31 mmol) was added and the pressure tube was closed and stirred while cooling was continued for 30 minutes. Then the reaction mixture was stirred in an oil bath at 40° C. for 7 hours. Water (0.15 mL) was added and the reaction mixture was stirred for 17 hours in an oil bath at 40° C. The reaction mixture was cooled to room temperature and concentrated in vacuo. The residue was taken up in $CH_2Cl_2$-$H_2O$ (50 mL-50 mL). The layers were separated and the water layer was extracted ($CH_2Cl_2$— 2×100 mL). The combined extracts were dried on $MgSO_4$, filtered and concentrated in vacuo yielding compound 87 (750 mg) as a brown oil which was used as such in the next reaction. Method A; Rt: 0.99 and 1.01 min. m/z: 336.2 (M+H)+ Exact mass: 335.1;

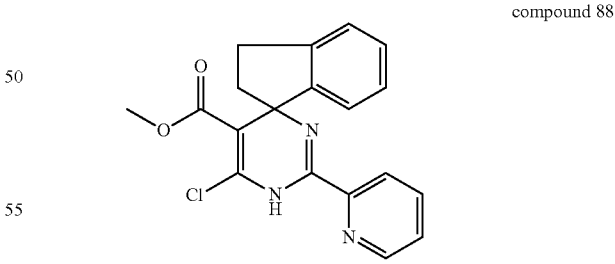

compound 88

Compound 87 (0.75 g) was dissolved in phosphorus oxychloride (5 mL, 53.81 mmol) and this mixture was refluxed for 1 hour in an oil bath at 110° C. The dark brown reaction mixture was concentrated in vacuo and treated with ice-water (100 mL). The obtained water layer was extracted using $CH_2Cl_2$ (3×50 mL). The combined extracts were dried on $MgSO_4$, filtrated and concentrated in vacuo. The dark brown residue was chromatographed by silica gel column chromatography (isocratic $CH_2Cl_2$) yielding compound 88 (460 mg)

as a dark yellow oil which was used as such in the next reaction. Method A; Rt: 1.15 min. m/z: 354.1 (M+H)⁺ Exact mass: 353.1;

compound 89

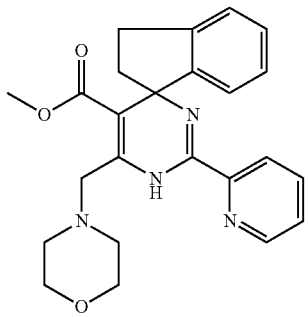

A microwave vial was charged with compound 88 (0.3 g, 0.81 mmol), cesium carbonate (1.57 g, 4.83 mmol), potassium (morpholin-4-yl)methyltrifluoroborate (0.33 g, 1.61 mmol), water (distilled, 0.44 mL) and 1,2-dimethoxyethane (4.2 mL). This mixture was purged with nitrogen for 5 minutes. Then palladium(II) acetate (0.018 g, 0.081 mmol) and butyldi-1-adamantylphosphine (0.046 g, 0.13 mmol) were added and the reaction mixture was purged for another 2 minutes. The vial was capped and heated under microwave irradiation at 140° C. for 30 minutes. The reaction mixture was cooled to room temperature and taken up in CH$_2$Cl$_2$-H$_2$O (50 mL-50 mL). The layers were separated and the water layer was extracted twice (CH$_2$Cl$_2$ 2×100 mL). The combined extracts were dried (MgSO$_4$), filtered and concentrated in vacuo. The residue was chromatographed by silica gel column chromatography (gradient CH$_2$Cl$_2$-methanol 100:0 to 98:2). The desired fractions were concentrated in vacuo and further dried in vacuo resulting in compound 89 (230 mg) as a yellow powder. Method A; Rt: 1.20 min. m/z: 419.2 (M+H)⁺ Exact mass: 418.2; ¹H NMR (400 MHz, CHLOROFORM-d) δ ppm 2.33 (ddd, J=13.2, 9.0, 4.0 Hz, 1H), 2.56-2.85 (m, 5H), 3.01 (ddd, J=15.8, 9.5, 4.0 Hz, 1H), 3.24 (ddd, J=15.8, 9.0, 7.0 Hz, 1H), 3.40 (s, 3H), 3.71 (d, J=16.6 Hz, 1H), 3.78 (d, J=16.6 Hz, 1H), 3.80-3.86 (m, 4H), 7.05-7.20 (m, 3H), 7.21-7.25 (m, 1H), 7.34 (ddd, J=7.5, 5.0, 1.1 Hz, 1H), 7.70 (td, J=7.7, 1.8 Hz, 1H), 8.17 (dt, J=8.0, 1.0 Hz, 1H), 8.59 (m, 1H), 9.97 (bs, 1H)

compound 90

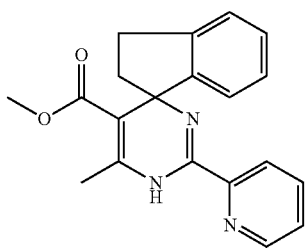

Compound 88 (160 mg, 0.43 mmol) was dissolved in N,N-dimethylformamide (2.8 mL) in a microwave vial and this was purged with nitrogen for 10 minutes. Then tetramethyltin (89.3 μl, 0.64 mmol) was added followed by bis(tri-t-butylphosphine)palladium (0.066 g, 0.13 mmol) and the vial was flushed with nitrogen and capped. The reaction mixture was heated under microwave irradiation at 140° C. for 10 minutes. The reaction mixture was concentrated in vacuo and co-evaporated with toluene (2×5 mL). The mixture was taken up in water-CH$_2$Cl$_2$ (30 mL-30 mL) and the water layer was extracted another two times with CH$_2$Cl$_2$ (2×30 mL). The combined extracts were dried on Na$_2$SO$_4$, filtered and concentrated in vacuo. The residue was chromatographed by silica gel column chromatography (gradient CH$_2$Cl$_2$—methanol 100:0 to 98:2). The fractions containing compound were concentrated and purified by silica gel column chromatography (gradient: Ethylacetate-heptane 0:100 to 15:85). The relevant fractions were concentrated and repurified by Preperative HPLC (RP SunFire Prep C18 OBD-10 μm, 30×150 mm). Mobile phase (0.25% NH$_4$HCO$_3$ solution in water, methanol) and further by Preperative HPLC on (RP SunFire Prep C18 OBD-10 μm, 30×150 mm). Mobile phase (0.1% TFA solution in water+5% CH$_3$CN, CH$_3$CN). The obtained fractions were dissolved in CH$_2$Cl$_2$ (15 mL) and then treated with sodium hydroxide (1M aq/10 mL). The layers were separated and the water layer was extracted twice using CH$_2$Cl$_2$ (2×15 mL). The combined extracts were dried, filtered and concentrated in vacuo. The obtained residue was chromatographed by silica gel column chromatography (gradient CH$_2$Cl$_2$-methanol 100:0 to 98:2) yielding compound 90 (3.2 mg) as a pure yellow oil. Method A; Rt: 1.14 min. m/z: 334.1 (M+H)⁺ Exact mass: 333.2

Compound 91

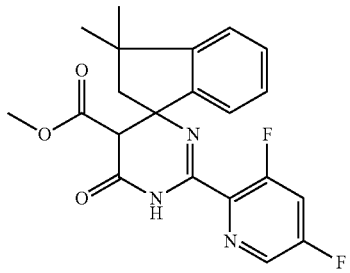

A tube was charged with a stirring bar, dimethyl 2-(3,3-dimethyl-2,3-dihydro-1H-inden-1-ylidene)malonate (2.50 g, 9.11 mmol; Prepared from 3,3-dimethylindan-1-one and dimethylmalonate similar as exemplified for compound 62. Formed crystals after work-up and evaporation of solvent were filtered and washed with petroleum ether), 3,5-difluoropyridine-2-carboxamidine (1.72 g, 10.9 mmol), and 1,4-dioxane (100 mL) under nitrogen atmosphere and the reaction mixture was heated at 50° C. for 24 hours and at 60° C. for 5 hours. The reaction mixture was evaporated to dryness. The residue was purified using silica gel column chromatography (dichloromethane in heptane in a gradient from 20 to 100%) to afford compound 91 (380 mg). Method A; Rt: 1.11 and 1.14 min. m/z: 400.2 (M+H)⁺ Exact mass: 399.1

Compound 92

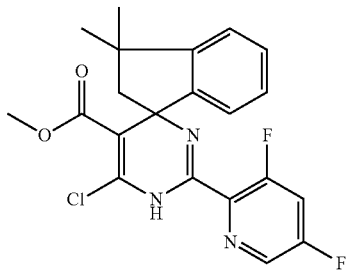

A tube was loaded with a stirring bar, compound 91 (380 mg) and phosphorous oxychloride (1.3 mL, 14.3 mmol) were added and the tube was closed with a Teflon cap. The reaction mixture was heated at 120° C. for 30 minutes and concentrated to dryness using a nitrogen flow at 40° C. The residue was dissolved in dichloromethane and washed with aqueous saturated sodium bicarbonate and brine, dried (Na$_2$SO$_4$) and evaporated to dryness resulting in compound 92 (270 mg) as yellow brown sticky oil which was used as such in the next step. Method A; Rt: 1.24. m/z: 418.1 (M+H)$^+$ Exact mass: 417.1

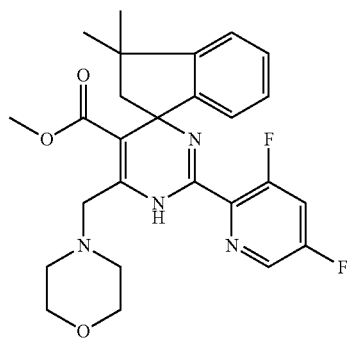

compound 93

A 10 mL microwave tube was loaded with a stirring bar, (morpholin-4-yl)methyltrifluoroborate internal salt (230 mg, 1.29 mmol), compound 92 (270 mg), cesium carbonate (1.26 g, 3.88 mmol), water (350 μL, 19.4 mmol) and 1,2-dimethoxyethane (3.4 mL, 32.3 mmol) and nitrogen gas was bubbled through for 10 minutes. Under a nitrogen atmosphere, palladium (II) acetate (14.6 mg, 0.065 mmol) and butyldi-1-adamantylphosphine (37.1 mg, 0.103 mmol) were added together and the reaction mixture was stirred at 140° C. in microwave oven for 10 minutes. The reaction mixture was cooled to room temperature. The water layer was extracted with dichloromethane (2×20 mL) and the organic layers were combined and washed with saturated aqueous sodium carbonate (2×5 mL) and water (5 mL). The organic layer was dried (Na$_2$SO$_4$) and concentrated to dryness. The residue was purified using silica gel column chromatography with ethyl acetate in heptane in a gradient from 5 to 50% resulting in, after concentration to dryness and drying in vacuo, compound 93 (169 mg) as off-white powder. Method A; Rt: 1.36 m/z: 483.2 (M+H)$^+$ Exact mass: 482.2

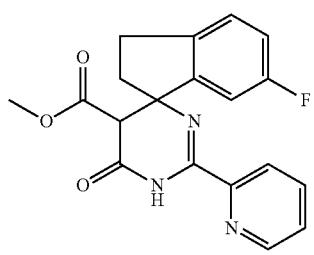

compound 94

A mixture of dimethyl 2-(6-fluoro-2,3-dihydro-1H-inden-1-ylidene)malonate (2 g, 7.57 mmol; Prepared from 6-fluoro-1-indanone and dimethylmalonate similar as exemplified for compound 62), pyridine-2-carboxamidine hydrochloride (1.63 g, 10.3 mmol) and Na$_2$CO$_3$ (2.17 g, 20.5 mmol) in DMF (20 mL) was stirred overnight at 60° C. under nitrogen atmosphere. The solvent was removed in vacuo. The residue was suspended in dichloromethane (100 mL) and the formed precipitate was filtered off. The filtrate, after concentration in vacuo, was purified using silica gel column chromatography twice. (Gradient: ethyl acetate in heptane from 0 to 40%) and next methanol in CH$_2$Cl$_2$ from 0 to 2%) to afford compound 94 (254 mg) which was used as such in the next step. Method A; Rt: 1.00 m/z: 354.1 (M+H)$^+$ Exact mass: 353.1

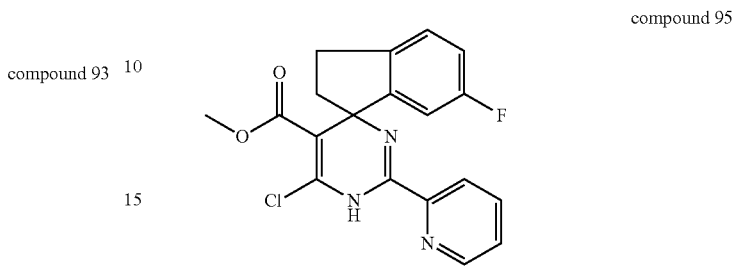

compound 95

Under a nitrogen atmosphere, a tube was charged with a stirring bar, compound 94 (254 mg) and phosphorous oxychloride (0.952 mL, 10.2 mmol) and closed with a Teflon cap. The mixture was stirred and heated at 120° C. for 30 minutes. After reaching room temperature the reaction mixture was concentrated to dryness under a nitrogen flow. The obtained residue was dissolved in dichloromethane and washed with saturated aqueous sodium bicarbonate, dried (Na$_2$SO$_4$) and evaporated to dryness in vacuo, resulting in compound 95 (230 mg) as dark brown sticky oil which was used as such in the next step. Method A; Rt: 1.14 m/z: 372.1 (M+H)$^+$ Exact mass: 371.1

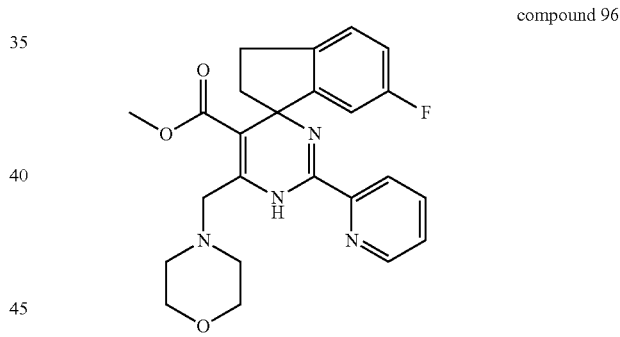

compound 96

A 10 mL microwave tube was loaded with a stirring bar, (morpholin-4-yl)methyltrifluoroborate internal salt (220 mg, 1.24 mmol), compound 95 (230 mg, 0.619 mmol), cesium carbonate (1209 mg, 3.71 mmol), water (335 μL, 18.6 mmol) and 1,2-dimethoxyethane (3.2 mL) and nitrogen gas was bubbled through for 10 minutes. Under a nitrogen atmosphere, palladium (II) acetate (14.0 mg, 0.062 mmol) and butyldi-1-adamantylphosphine (35.5 mg, 0.099 mmol) were added together and the reaction mixture was stirred at 140° C. in microwave oven for 10 minutes. The reaction mixture was allowed to reach room temperature. The water layer was extracted with dichloromethane (2×20 mL) and the organic layers were combined and washed with saturated aqueous sodium carbonate (2×5 mL) and water (5 mL). The organic layer was dried (Na$_2$SO$_4$) and concentrated to dryness. The residue was purified using silica gel column chromatography with ethyl acetate in heptane in a gradient from 5 to 50% resulting in compound 96 (216 mg) as a powder which was dried in vacuo. Method A; Rt: 1.21 m/z: 437.2 (M+H)$^+$ Exact mass: 436.2. $^1$H NMR (400 MHz, CHLOROFORM-d) δ ppm 2.34 (ddd, J=13.1, 9.1, 4.1 Hz, 1H), 2.58-2.68 (m, 5H), 2.90-3.01 (m, 1H), 3.12-3.22 (m, 1H), 3.45 (s, 3H), 3.71 (d, J=16.8 Hz, 1H), 3.80 (d, J=16.8 Hz, 1H), 3.82-3.87 (m, 4H), 6.79 (dd, J=8.9, 2.4 Hz, 1H), 6.87 (td, J=8.7, 2.5 Hz, 1H), 7.16 (dd, J=8.3, 5.0 Hz, 1H), 7.36 (ddd, J=7.5, 4.8, 1.3 Hz, 1H), 7.71 (td, J=7.7, 1.6 Hz, 1H), 8.16 (dt, J=8.0, 1.0 Hz, 1H), 8.59 (br. d, J=4.3 Hz, 1H), 10.04 (br. s., 1H). Compound 96 was purified by preparative SFC on (Chiralcel Diacel OD 20×250 mm). Mobile phase (CO$_2$, methanol with 0.2% iPrNH$_2$), the desired fractions were collected, evaporated, solved in methanol and evaporated again yielding compound 96a and 96b as light yellow powder. SFC: OD-H 250 mm×4.6 mm; Flow: 3 mL/min; Mobile phase: 5% MeOH (containing 0.2% iPrNH$_2$) hold 17.00 min, from 5-50# MeOH (containing 0.2% iPrNH$_2$) at 10% rate and hold 3.10 min at 50%; Temperature: 30° C. Rt (96a): 10.8 min; Rt (96b): 11.9 min

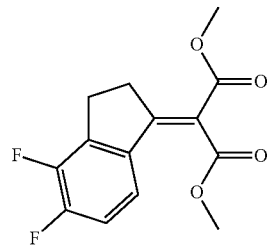

compound 97

A solution of 4,5-difluoro-1-indanone (15 g, 89.2 mmol) and dimethylmalonate (11.2 mL, 98.1 mmol) in tetrahydrofuran (500 mL) was cooled to 0° C. under nitrogen atmosphere and titanium tetrachloride (20.6 mL, 187 mmol) in dichloromethane (50 mL) was added drop wise. Pyridine (37.4 mL, 462 mmol) was added finally. The resulting mixture was stirred for 16 hours at room temperature. The reaction mixture was filtered over decalite and ethyl acetate (500 mL) was added into the filtrate. The organic layer was washed with Brine (3×200 mL). The combined aqueous layers were acidified with 1N hydrochloric acid (100 mL) and extracted with ethyl acetate (200 mL). The combined organic layers were washed with Brine (50 mL), dried (Na$_2$SO$_4$) and evaporated. The residue was purified using silica gel column chromatography (gradient dichloromethane in heptane from 0 to 50%). The desired fractions were combined and concentrated to a volume of 200 mL. The formed solids were filtered and washed with heptane. The filtrate was evaporated to dryness resulting in compound 97 (3.74 g) as brown powder. Method A; Rt: 1.10 m/z: 300.1 (M+NH$_4$)$^+$ Exact mass: 282.1

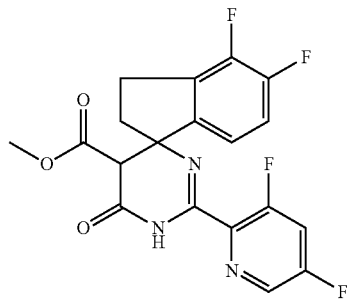

compound 98

A tube was charged with a stirring bar, compound 97 (3.00 g, 10.6 mmol), 3,5-difluoro-2-pyridine carboximidamide (3.34 g, 21.3 mmol) and 1,4-dioxane (30 mL) under nitrogen atmosphere. The reaction mixture was heated at 50° C. for 4 hours and allowed to reach room temperature overnight. The reaction mixture was concentrated to dryness and the residue was purified using silica gel column chromatography (gradient ethyl acetate in heptane from 10 to 50%) to afford compound 98 (500 mg) as brown powder. Method A; Rt: 1.06 (two isomers) m/z: 408.1 (M+H)$^+$ Exact mass: 407.1

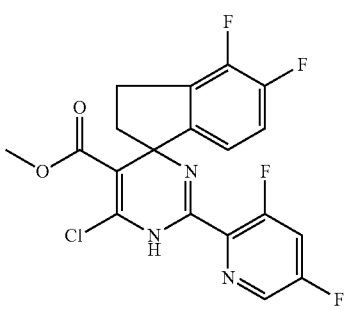

compound 99

Under a nitrogen atmosphere, a tube was charged with a stirring bar, compound 98 (500 mg) and phosphorous oxychloride (1.0 mL, 11 mmol). The mixture was stirred and heated at 120° C. for 30 minutes. After cooling to room temperature the reaction mixture was concentrated to dryness under a nitrogen flow. The obtained residue was dissolved in dichloromethane and washed with saturated aqueous sodium bicarbonate solution, dried (Na$_2$SO$_4$) and evaporated to dryness in vacuo. The obtained residue was purified using silica gel column chromatography (isocratic dichloromethane) to afford compound 99 (130 mg) as a brown powder. Method A; Rt: 1.12 m/z: 426.1 (M+H)$^+$ Exact mass: 425.1

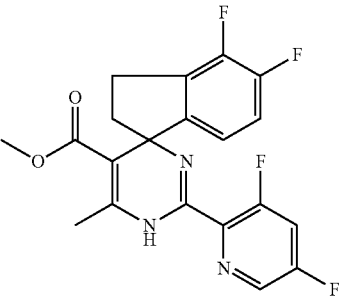

compound 100

Compound 99 (100 mg), was dissolved in 1,2-dimethoxyethane (1.60 mL, 15.4 mmol) in a microwave vial and the solution was deoxygenized by bubbling through nitrogen gas for 10 minutes. Then, tetramethyltin (0.039 mL, 0.28 mmol), was added followed by bis(tri-t-butylphosphine)palladium (0) (36.0 mg, 0.071 mmol) and the vial was flushed with nitrogen and capped. The reaction mixture was heated under microwave irradiation at 140° C. for 10 minutes and allowed to reach room temperature. Nitrogen gas was bubbled through for 10 minutes. Then, more tetramethyltin (0.039 mL, 0.282 mmol) was added followed by bis(tri-t-butylphosphine) palladium (0) (36.0 mg, 0.071 mmol) and the vial was flushed with nitrogen and capped. The reaction mixture was heated under microwave irradiation at 140° C. for 20 minutes. The reaction mixture was concentrated to dryness. The residue was purified by preperative HPLC (RP SunFire Preperative C18 OBD-10 μm, 30×150 mm). Mobile phase (0.1% TFA solution in water+5% acetonitrile, acetonitrile). The desired fractions were combined and concentrated to dryness. The residue was neutralized with saturated aqueous sodium bicarbonate and extracted with dichloromethane (2×20 mL). The combined organic layers were dried (Na$_2$SO$_4$) and concentrated to dryness in vacuo. The obtained residue was co evaporated with methanol (2×5 mL) and dried in vacuo resulting in compound 100 (21 mg) as yellow powder. Method A; Rt: 1.12 m/z: 406.1 (M+H)$^+$ Exact mass: 405.1. $^1$H NMR (400 MHz, CHLOROFORM-d): ppm 2.25-2.46 (m, 4H), 2.61-2.82 (m, 1H), 2.96-3.10 (m, 1H), 3.12-3.30 (m, 1H), 3.47 (s, 3H), 6.71-7.12 (m, 2H), 7.17-7.39 (m, 1H), 7.98 (br. s, 1H), 8.27 (d, J=2.0 Hz, 1H).

compound 101

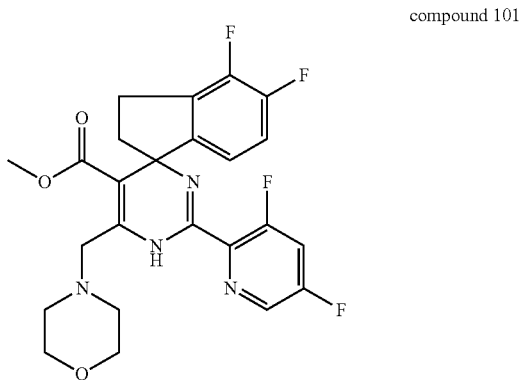 [SMILES: COC(=O)C1=C(CN2CCOCC2)NC(c2ncc(F)cc2F)=NC12CCc1c2ccc(F)c1F]

A 10 mL microwave tube was loaded with a stirring bar, (morpholin-4-yl)methyltrifluoroborate internal salt (22.6 mg, 0.127 mmol), compound 99 (30 mg, 0.0705 mmol), water (34.3 μL, 1.90 mmol) and 1,2-dimethoxyethane (1.5 mL). Nitrogen gas was bubbled through for 10 minutes. Under a nitrogen atmosphere, cesium carbonate (124 mg, 0.38 mmol), palladium (II) acetate (1.60 mg, 0.00705 mmol) and butyldi-1-adamantylphosphine (4.04 mg, 0.0113 mmol) were added together and the reaction mixture was stirred at 140° C. in microwave oven for 10 minutes. The reaction mixture was cooled to room temperature. The water layer was extracted with dichloromethane (10 mL) and the organic layers were combined and washed with saturated aqueous sodium carbonate (2×5 mL) and brine (5 mL). The organic layer was dried (Na$_2$SO$_4$) and concentrated to dryness. The residue was purified using silica gel column chromatography (ethyl acetate in heptane in a gradient from 5 to 50%) resulting in compound 101 (3.2 mg) as a yellow powder after concentration and drying in vacuo. Method A; Rt: 1.21 m/z: 491.1 (M+H)$^+$ Exact mass: 490.2 $^1$H NMR (400 MHz, CHLOROFORM-d) ppm 2.40 (ddd, J=13.0, 9.0, 3.8 Hz, 1H), 2.55-2.71 (m, 5H), 2.98-3.10 (m, 1H), 3.14-3.28 (m, 1H), 3.45 (s, 3H), 3.67 (d, J=16.8 Hz, 1H), 3.73-3.84 (m, 5H), 6.79 (dd, J=8.3, 4.0 Hz, 1H), 6.93 (dt, J=10.4, 7.7 Hz, 1H), 7.20-7.33 (m, 1H), 8.34 (d, J=2.0 Hz, 1H), 9.61 (br. s, 1H).

compound 102

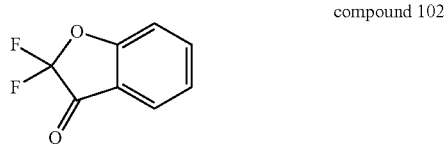 [SMILES: O=C1c2ccccc2OC1(F)F]

To 2-bromophenol (8.6 g, 49.7 mmol) in DMF (100 mL) at room temperature, K$_2$CO$_3$ (34.4 g, 248 mmol) was added. After 5 minutes, ethyl 2-bromo-2,2-difluoroacetate (12.1 g; 59.65 mmol) was added. The mixture was stirred at room temperature overnight. Next, saturated NH$_4$Cl (200 mL) was added and the mixture was extracted with CH$_2$Cl$_2$ (3×). The combined organic layers was dried on MgSO$_4$, filtrated and the solvent was removed in vacuo. The obtained residue was purified by gradient elution on silica gel column chromatography with heptane/EtOAc, resulting in ethyl 2-(2-bromophenoxy)-2,2-difluoroacetate (7.78 g). $^1$H NMR (400 MHz, DMSO-d$_6$) ppm 1.27 (t, J=7.2 Hz, 3H), 4.40 (q, J=7.1 Hz, 2H), 7.30 (td, J=7.7, 1.8 Hz, 1H), 7.36-7.45 (m, 1H), 7.45-7.54 (m, 1H), 7.78 (dd, J=8.0, 1.5 Hz, 1H). Method A; Rt: 1.19. To 2-(2-bromophenoxy)-2,2-difluoroacetate (3 g, 10.2 mmol) in THF/H$_2$O (50 mL/50 mL), LiOH (320 mg, 13.4 mmol) was added, the mixture was stirred at 40° C. After 2.5 hours the mixture was cooled to room temperature, acidified with 1 N HCl and THF was removed in vacuo. The water layer was extracted with CH$_2$Cl$_2$, the combined organic layer were dried with Na$_2$SO$_4$, filtrated and the solvent was removed in vacuo resulting in 2-(2-bromophenoxy)-2,2-difluoroacetic acid as a colourles oil (3011 mg, containing 14 w % THF according to $^1$H-NMR). Method A; Rt: 1.21 m/z: 266.9 (M−H)$^-$ Exact mass: 267.9. To 2-(2-bromophenoxy)-2,2-difluoroacetic acid (6.04 g), prepared as described above)) in dry THF (150 mL) at −10° C. under argon, BuLi (2.5M in hexane; 24.2 mL; 60.4 mmol) was added dropwise. The mixture was stirred for 10 minutes and then poured into 1N HCl (200 mL), extracted with CH$_2$Cl$_2$ (3×), dried on Na$_2$SO$_4$ and filtrated. The solvent was removed (40° C., up till 100 mbar) resulting in 5.5 g oily residue containing compound 102, which was used a such in the next reaction. Method D; Rt: 0.99; 19 F NMR (377 MHz, DMSO-d$_6$) ppm −92.77. $^1$H NMR (400 MHz, DMSO-d$_6$) ppm 7.43 (td, J=7.7, 0.7 Hz, 1H), 7.50 (dt, J=8.5, 0.7 Hz, 1H), 7.91 (ddd, J=7.7, 1.5, 0.7 Hz, 1H), 7.98 (ddd, J=8.5, 7.5, 1.5 Hz, 1H).

compound 103

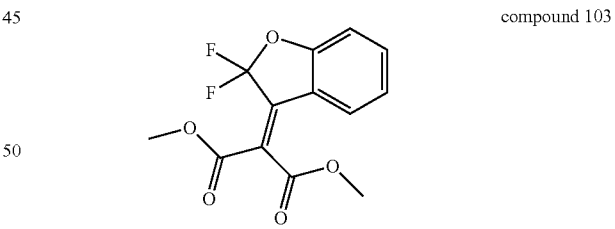

Titanium(IV) chloride was added drop wise to a solution of 2,2-difluoroindan-1-one (compound 102; 3.18 g) and dimethyl malonate (2.5 mL, 21.8 mmol) in THF (60 mL) cooled in an ice bath (0° C.). Then pyridine (5.8 mL, 73 mmol) was added drop wise and the reaction mixture was stirred at 0° C. for 2.5 hours and then at room temperature for 64 hours. Water (100 mL) was added to the reaction mixture followed by an extraction with CH$_2$Cl$_2$ (2×300 mL). The organic layers are combined and dried (Na$_2$SO$_4$). After filtration and concentration, the residue was purified by silica gel column chromatography (ethyl acetate in heptane from 0 to 10%) yielding compound 103 (2.6 g) as a colorless liquid. Method A; Rt: 1.10 m/z: 302.1 (M+NH$_4$)$^+$ Exact mass: 284.1 compound 104

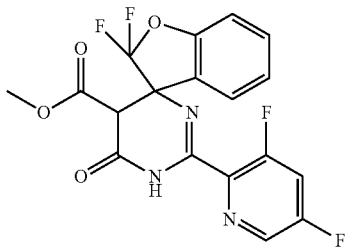

A tube was loaded with a stirring bar, compound 103 (1.00 g, 3.52 mmol), 3,5-difluoro-2-pyridine carboximidamide (693 mg, 3.56 mmol) and 1,4-dioxane (5 mL) and closed with a Teflon cap. The reaction mixture was stirred at room temperature for 12 hours and heated at 40° C. for 1.5 hours. More 3,5-difluoro-2-pyridine carboximidamide (315 mg, 1.62 mmol) was added and the reaction mixture was heated at 40° C. for 4 hours and allowed to reach room temperature. The reaction mixture was evaporated resulting in a slightly orange oily residue containing compound 104 which was used as such in the next reaction. Method A; Rt: 1.02 m/z: 410.1 (M+H)$^+$ Exact mass: 409.1 compound 105

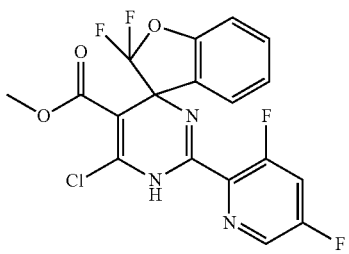

A tube was loaded with a stirring bar, compound 104 (1.32 g, 3.24 mmol), phosphorus oxychloride (4.56 mL, 49.1 mmol) and closed with a Teflon cap. The reaction mixture was stirred at 90° C. for 4 hours. The reaction mixture was evaporated to dryness and co evaporated with toluene. The brown-black residue was dissolved in $CH_2Cl_2$ and stirred with saturated aqueous sodium bicarbonate at room temperature for 30 minutes. The water phase was extracted with dichloromethane and the combined organic layers were dried ($Na_2SO_4$) and after filtration, evaporated to dryness. The black tarry residue was purified using silica gel column chromatography (dichloromethane). All the desired fractions were combined and evaporated to dryness to afford compound 105 (580 mg) as yellow powder. Method A; Rt: 1.11 m/z: 428.0 (M+H)$^+$ Exact mass: 427.0 compound 106

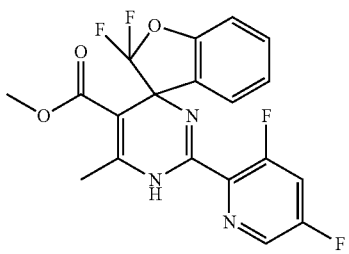

A solution of compound 105 (580 mg, 1.36 mmol) in DMF (5 mL) in a microwave vial was stirred and nitrogen was bubbled through for 10 minutes. Then tetramethyltin (0.28 mL, 2.0 mmol) was added followed by bis(tri-t-butylphosphine)palladium(0) (69.3 mg, 0.136 mmol) and the vial was flushed with nitrogen and capped.

The reaction mixture was heated under microwave irradiation at 140° C. for 30 minutes and allowed to reach room temperature. The reaction mixture was filtered and the filtrate was evaporated to dryness. The residue was mixed with methanol (40 mL), filtered and the filtrate was evaporated to dryness to afford an orange sticky residue (635 mg). 540 mg of the residue was purified using silica gel column chromatography (gradient ethyl acetate in heptane from 5 to 30%). The desired fractions were combined and evaporated to keep 100 mL of the solvent. The solids were filtered and washed with heptane and dried in vacuum oven at 50° C. for 2 hours to afford compound 106 (32 mg) as light yellow powder. Method E; Rt: 1.00 m/z: 408.1 (M+H)$^+$ Exact mass: 407.1. The filtrate was evaporated to dryness to afford a yellow powder which was purified by Preperative SFC on Chiralcel Diacel OJ 20×250 mm. Mobile phase ($CO_2$, isopropanol), the desired fractions were collected, evaporated, dissolved in methanol and evaporated again, yielding compound 106a (111 mg) and compound 106b. SFC: Columns: OJ-H 250 mm×4.6 mm; Flow: 3 mL/min; Mobile phase: 5% iPrOH (containing 0.2% $iPrNH_2$) hold 15.0 min Temperature: 23° C.; Rt (106a): 8.37 min; Rt (106b): 9.95 min.

compound 107

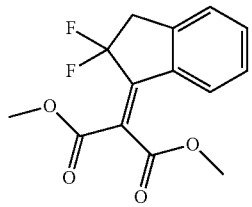

$TiCl_4$ (9.8 mL) dissolved in dichloromethane (30 mL) was added dropwise during 10 minutes to a solution of 2,2-difluoroindan-1-one (8.0 g; 47.6 mmol) and dimethylmalonate (6.3 g; 47.6 mmol) dissolved in THF (125 mL), while cooling in an icebath. The reaction mixture was stirred 10 minutes. Then pyridine (14.9 mL; 185 mmol) was added and the reaction mixture was allowed to reach room temperature while stirring overnight. The mixture was quenched with water (100 mL) and diluted with dichloromethane (300 mL). The organic layer was separated, dried over sodium sulphate, filtered and concentrated. The residue was purified by column chromatography on silica by gradient elution from 2 to 100% EtOAc in heptane. The product fractions were combined and concentrated yielding compound 107 (7.51 g) which was used as such in the next reaction Method A; Rt: 1.01 m/z: 300.1 (M+NH$_4$)$^+$ Exact mass: 282.1; $^1$H NMR (400 MHz, CHLOROFORM-d) ppm 3.50 (t, J=13.4 Hz, 2H), 3.88 (s, 3H), 3.91 (s, 3H), 7.27-7.35 (m, 2H), 7.39-7.47 (m, 1H), 7.66 (d, J=8.5 Hz, 1H).

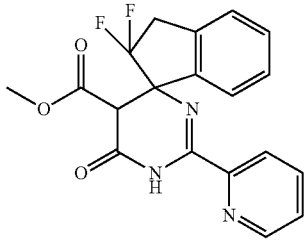

compound 108

A mixture of compound 107 (6.8 g), 2-amidinopyridiniumchloride (3.35 g; 21.3 mmol), and sodium bicarbonate (7.15 g)) in dioxane (100 mL) were stirred and heated 5 hours at 120° C. The reaction mixture was filtrated while still warm and the filtrate was concentrated in vacuo. The obtained residue was purified by column chromatography on silica using a gradient elution from 5 to 100% EtOAc in heptane. The product fractions were combined, concentrated and dried overnight in vacuo yielding compound 108 (diastereomeric mixture; 3.83 g) as a white powder. Method A; Rt: 1.00 and 1.03 m/z: 372.1 (M+H)$^+$ Exact mass: 371.1.

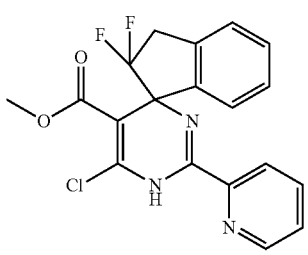

compound 109

Compound 108 (1.05 g) was dissolved in phosphorous oxychloride (25 mL) and heated 210 minutes at 100° C. The reaction mixture was concentrated in vacuo. The residue was dissolved in dichloromethane (100 mL) and quenched by pouring the mixture in saturated NaHCO$_3$ (200 mL) solution while stirring. The organic layer was separated, dried over sodium sulphate, filtered and concentrated yielding a yellow crude resin (1.05 g) which was used as such in the next step. Method A; Rt: 1.15 m/z: 390.1 (M+H)$^+$ Exact mass: 389.1.

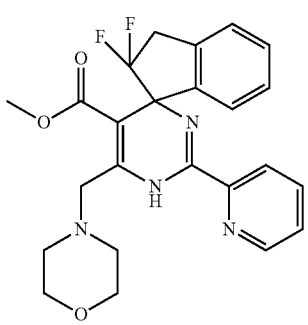

compound 110

Nitrogen was bubbled through a mixture of compound 109 (681 mg) potassium(morpholin-4-yl)methyltrifluoroborate (345.5 mg; 1.67 mmol), K$_2$CO$_3$ (319.3 mg; 2.31 mmol), ethylene glycol dimethylether (5 mL) and water (1 mL). Then, (164 mg; 0.32 mmol) bis(tri-tert-butylphosphine)palladium (0) was added and the reaction mixture stirred under microwave irradiation at 140° C. during 10 minutes. The mixture was concentrated and the residue taken up in water (50 mL) and dichloromethane (50 mL). The organic layer was separated, dried over an HM-N cartridge and concentrated. The residue was purified by column chromatography on silica using a gradient from 5 till 100% EtOAc in heptanes. The product fractions were combined and concentrated. and dried in vacuo, yielding a yellow resin (214 mg). Method A; Rt: 1.14 m/z: 455.1 (M+H)$^+$ Exact mass: 454.2. $^1$H NMR (400 MHz, CHLOROFORM-d) δ ppm 2.57-2.69 (m, 4H), 3.36 (s, 3H), 3.41-3.58 (m, 1H), 3.59-3.71 (m, 1H), 3.75-3.88 (m, 6H), 7.08-7.16 (m, 1H), 7.20-7.26 (m, 3H), 7.37 (ddd, J=7.5, 4.8, 1.3 Hz, 1H), 7.71 (td, J=7.7, 1.6 Hz, 1H), 8.19 (dt, J=8.0, 1.0 Hz, 1H), 8.56-8.64 (m, 1H), 10.35 (s, 1H)

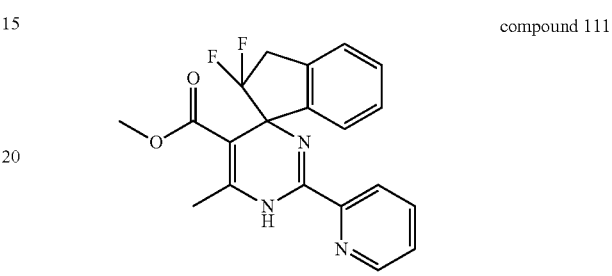

compound 111

Nitrogen was bubbled through a mixture of compound 109 (365 mg) tetramethyltin (185 mg; 1.03 mmol) ethylene glycol dimethylether (5 mL) and DMF (1 mL) during 5 minutes. Then (105.5 mg, 0.21 mmol) bis(tri-tert-butylphosphine)palladium (0) was added and the reaction mixture stirred under microwave irradiation at 140° C. during 15 minutes. Another tetramethyltin (100 mg) was added and nitrogen bubbled through during 5 minutes. Then, more bis(tri-tert-butylphosphine)palladium (0) (100 mg) was added and stirred under microwave irradiation at 140° C. during 30 minutes. The reaction mixture was concentrated in vacuo and the obtained residue taken up in CH$_2$Cl$_2$ (50 mL) and water (50 mL). The organic layer was dried over an HM-N cartridge and concentrated. The residue was purified by column chromatography on silica using a gradient from 5 till 100% EtOAc in heptane. The procedure was repeated on the concentrated product fractions with a gradient from 0 till 10% methanol in dichloromethane. The product fractions were combined, concentrated and dried in vacuo yielding compound III (54 mg). Method E; Rt: 1.05 m/z: 370.2 (M+H)$^+$ Exact mass: 369.1; $^1$H NMR (400 MHz, DMSO-d6) δ ppm 2.35 (s, 3H), 3.27 (s, 3H), 3.38-3.64 (m, 2H), 7.03-7.11 (m, 1H), 7.18-7.30 (m, 3H), 7.57 (ddd, J=7.5, 4.8, 1.3 Hz, 1H), 7.88 (td, J=7.7, 1.8 Hz, 1H), 7.94-8.00 (m, 1H), 8.64-8.70 (m, 1H), 9.83 (s, 1H)

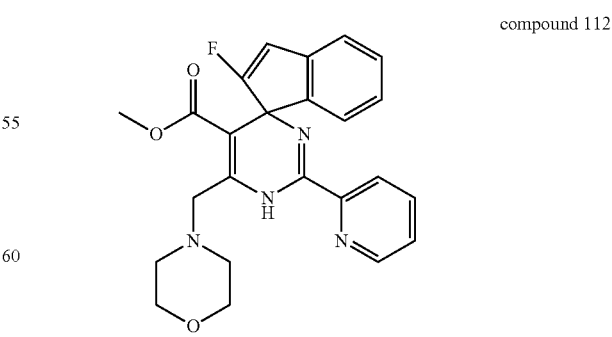

compound 112

Compound 110 (106 mg), 1 M NaOH (2 mL, 2 mmol) and methanol (4 mL) were heated at 140° C. under microwave irradiation for 3 minutes, followed by 3 minutes more at 140°

C. Methanol was distilled off in vacuo and the oil was extracted from the water layer with dichloromethane (50 mL). The organic layer was dried over an HM-N cartridge and concentrated. The residue was purified by column chromatography on using a gradient from 5 till 15% EtOAc in heptane. The product fractions were concentrated and dried in vacuo resulting in compound 112 (18.5 mg). Method E; Rt: 1.09 m/z: 435.2 (M+H)$^+$ Exact mass: 434.2; $^1$H NMR (400 MHz, CHLOROFORM-d) δ ppm 2.61-2.68 (m, 4H), 3.39 (s, 3H), 3.81-3.88 (m, 6H), 5.96 (s, 1H), 7.04-7.10 (m, 1H), 7.12-7.23 (m, 3H), 7.36 (ddd, J=7.5, 4.8, 1.3 Hz, 1H), 7.71 (td, J=7.7, 1.8 Hz, 1H), 8.18 (dt, J=7.9, 1.0 Hz, 1H), 8.56-8.63 (m, 1H), 10.36 (br. s., 1H)

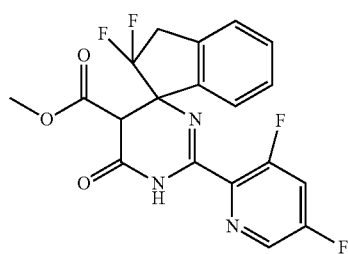

compound 113 compound 107 (850 mg), 3,5-difluoropyridine-2-carboxamidine (627 mg; 3.99 mmol), NaHCO$_3$ (894 mg) in dioxane (30 mL) was stirred and heated at 60° C. during 3 hours. The reaction mixture was concentrated and the residue taken up in CH$_2$Cl$_2$ (50 mL). This solution was washed with water, dried over an HM-N cartridge and concentrated. The residue was subjected to column chromatography on silica using a gradient from 5 till 100% EtOAc. The product fractions were combined concentrated and dried in vacuo, resulting in compound 113 as a white powder (494 mg) as a diastereomeric mixture in ~8 to 2 ratio. Method E; Rt: 0.93 and 0.95 m/z: 408.2 (M+H)$^+$ Exact mass: 407.1

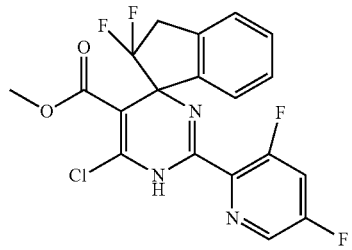

compound 114 compound 113 (459 mg) was dissolved in phosphorous oxychloride and heated for 1 hour at 120° C. The reaction mixture was concentrated in vacuo and the obtained residue was taken up in CH$_2$Cl$_2$ (50 mL) and quenched with saturated NaHCO$_3$ solution (150 mL). This mixture was vigorously stirred for 15 minutes. The organic layer was separated, dried over an isolute HM-N cartridge and concentrated, yielding compound 114 (375 mg) as a crude brown powder which was used as such in the next reaction. Method E; Rt: 1.05 m/z: 426.1 (M+H)$^+$ Exact mass: 425.1

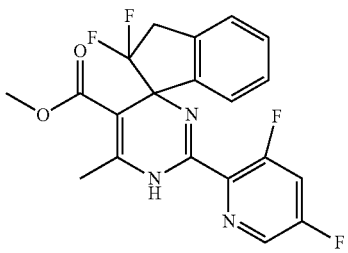

compound 115

Nitrogen was bubbled through a solution of compound 114 (375 mg)) and tetramethyltin (187 mg) dissolved in DMF (7 mL) during 10 minutes. Bis(tri-tert-butylphosphine)palladium (0) (107 mg) was added and the reaction stirred under microwave irradiation at 140° C. during 15 minutes. Nitrogen was bubbled through again during 5 minutes, more bis(tri-tert-butylphosphine)palladium (0) (100 mg) and tetramethyltin (185 mg) were added and the reaction mixture was stirred under microwave irradiation for 30 minutes at 140° C. The reaction mixture was filtered and concentrated. The residue was dissolved in CH$_2$Cl$_2$ (50 mL), washed with water, dried over an HM-N cartridge and concentrated. The residue was purified by column chromatography on silica using a gradient from 2.5% till 100% EtOAc in heptane. The product fractions were combined, concentrated and dried in vacuo, yielding compound 115 (71.7 mg) as a yellow resin. Method A; Rt: 1.07 m/z: 406.1 (M+H)$^+$ Exact mass: 405.1. $^1$H NMR (400 MHz, DMSO-d$_6$; main tautomer described) ppm 2.27 (s, 3H), 3.27 (s, 3H), 3.37-3.55 (m, 2H), 7.02-7.13 (m, 1H), 7.16-7.31 (m, 3H), 8.04 (ddd, J=10.3, 9.1, 2.4 Hz, 1H), 8.60 (d, J=2.4 Hz, 1H), 9.91 (s, 1H)

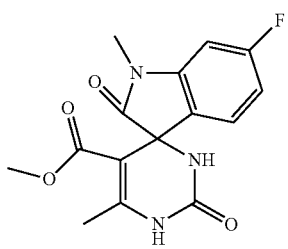

compound 116

6-fluoro-1-methyl-2,3-dihydro-1H-indole-2,3-dione (1751 mg, 9.78 mmol), urea (587 mg, 9.78 mmol), methyl acetoacetate (1.14 g, 9.78 mmol), p-TSA (84.2 mg; 0.49 mmol) in acetonitrile (150 mL) was refluxed for 4 days. The reaction mixture was allowed to cool to room temperature and stirred overnight. The product crystallised out and the light yellow crystals were filtered off and dried in vacuo, resulting in compound 116 (602 mg) Method D; Rt: 0.71 m/z: 337.1 (M+NH$_4$)$^+$ Exact mass: 319.1. $^1$H NMR (400 MHz, DMSO-d$_6$) δ ppm 2.24 (s, 3H), 3.09 (s, 3H), 3.30 (s, 3H), 6.75 (ddd, J=10.0, 8.0, 2.3 Hz, 1H), 6.93 (dd, J=9.5, 2.3 Hz, 1H), 7.18 (dd, J=8.3, 5.5 Hz, 1H), 7.77 (d, J=1.3 Hz, 1H), 9.49 (m, 1H)

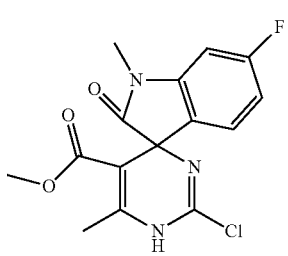

compound 117

Compound 116 (580 mg 1.82 mmol) in POCl$_3$ (25 mL) was heated at 95° C. during 6 hours. The reaction mixture was concentrated. The residue was dissolved in CH$_2$Cl$_2$ (100 mL) and poured in saturated NaHCO$_3$ (100 mL) solution. This mixture was stirred 20 minutes vigorously, the organic layer was separated, dried over an HM-N cartridge and concentrated yielding compound 117 as a dark brown powder which was used as such in the next reaction. Method E; Rt: 0.73 m/z: 338.2 (M+H)$^+$ Exact mass: 337.1

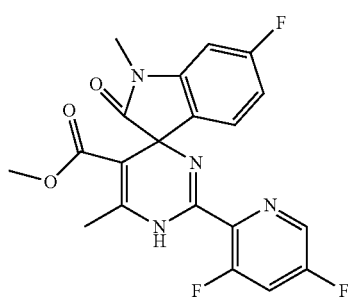

compound 118

Nitrogen was bubbled through a mixture of compound 117 (525 mg), 3,5-difluoro-2-tributylstannylpyridine (722 mg, 1.79 mmol) dissolved in DMF (7 mL). Then bis(tri-tert-butylphosphine)palladium (0) (159 mg, 0.31 mmol) was added and the mixture heated under microwave irradiation at 140° C. during 10 minutes. The reaction mixture was concentrated and purified by Prep HPLC on (RP Vydac Denali C18-10 µm, 200 g, 5 cm). Mobile phase (0.25% NH$_4$HCO$_3$ solution in water, CH$_3$CN), the desired fractions were collected, evaporated, dissolved in MeOH and evaporated again, and finally dried in vacuo resulting in compound 118 (21 mg). Method E; Rt: 0.85 m/z: 417.1 (M+H)$^+$ Exact mass: 416.1; $^1$H NMR (400 MHz, DMSO-d$_6$) δ ppm 2.37 (s, 3H), 3.13 (s, 3H), 3.35 (s, 3H), 6.67-6.80 (m, 1H), 6.92 (dd, J=9.7, 2.4 Hz, 1H), 7.15 (dd, J=8.2, 5.6 Hz, 1H), 7.93-8.15 (m, 1H), 8.60 (d, J=2.3 Hz, 1H), 9.13-10.47 (bs, 1H).

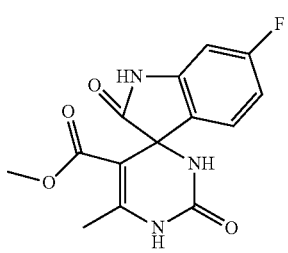

compound 119

6-fluoroindoline-2,3-dione (15.05 g, 91.1 mmol), urea (5.47 g, 91.1 mmol), p-TSA (7.85 g, 45.57 mmol) and methyl acetoacetate (10.6 g, 91.1 mmol) in acetonitrile (500 mL) was refluxed overweekend. The reaction mixture was allowed to cool to room temperature. The precipitate was filtered off. The precipitate was taken up in CH$_2$Cl$_2$ (1 L) and saturated NaHCO$_3$ solution (500 mL). The mixture was stirred vigorously during 15 minutes. The precipitate was filtered off and dried in vacuo, resulting in compound 119 as a beige powder (9.25 g). Method A; Rt: 0.61 m/z: 323.1 (M+NH$_4$)$^+$ Exact mass: 305.1; $^1$H NMR (400 MHz, DMSO-d$_6$) δ ppm 2.24 (s, 3H), 3.32 (s, 3H), 6.57 (dd, J=9.4, 2.3 Hz, 1H), 6.63-6.75 (m, 1H), 7.13 (dd, J=8.0, 5.6 Hz, 1H), 7.81 (s, 1H), 8.31-11.56 (m, 2H).

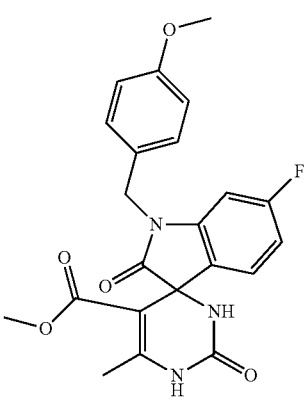

compound 120

Compound 119 (1225 mg; 4.0 mmol), 4-methoxybenzylchloride (660 mg; 4.2 mmol) and potassium carbonate (693 mg) in acetonitrile (30 mL) was stirred and refluxed overnight. The reaction mixture was concentrated and the residue dissolved in CH$_2$Cl$_2$ (100 mL) and water (100 mL). The organic layer was dried over an HM-N cartridge and concentrated. The residue was purified by column chromatography on silica using a gradient from 2 till 10% CH$_3$OH in CH$_2$Cl$_2$. The product fractions were combined, concentrated and dried overnight in vacuo resulting in compound 120 as a white powder (818 mg). Method A; Rt: 0.91 m/z: 443.1 (M+NH$_4$)$^+$ Exact mass: 425.1; $^1$H NMR (400 MHz, DMSO-d$_6$) δ ppm 2.24 (s, 3H), 3.07 (s, 3H), 3.73 (s, 3H), 4.69 (d, J=15.4 Hz, 1H), 4.81 (d, J=15.4 Hz, 1H), 6.68-6.81 (m, 2H), 6.86-6.95 (m, J=8.8 Hz 2H), 7.20 (dd, J=7.9, 5.5 Hz, 1H), 7.39-745 (m, J=8.8 Hz, 2H), 7.92 (d, J=1.3 Hz, 1H), 9.51 (bs, 1H)

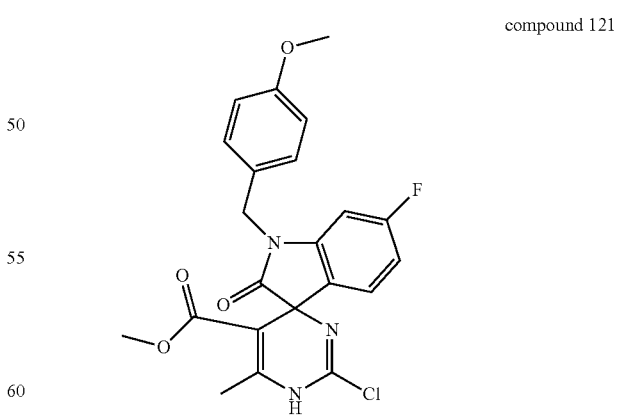

compound 121

Compound 120 (758 mg; 1.78 mmol) in POCl$_3$ (30 mL) was stirred at 100° C. during 1 hour. Then the reaction mixture was heated further at 110° C. during 110 min. The reaction mixture was concentrated. The residue was dissolved in CH$_2$Cl$_2$ (50 mL) poured in saturated NaHCO$_3$ (100 mL) solu-

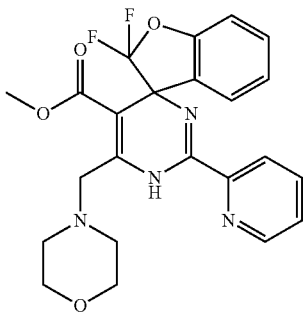
compound 124

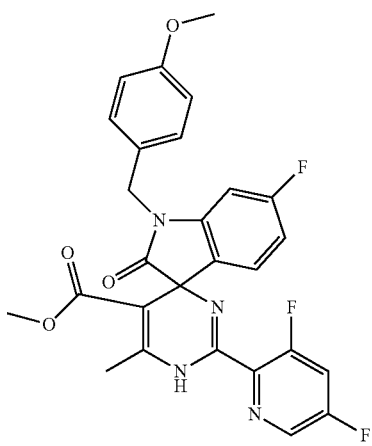
compound 122

Nitrogen was bubbled through a mixture of compound 121 (513 mg, 1.16 mmol), 3,5-difluoro-2-tributylstannylpyridine (700 mg; 1.73 mmol) and DMF (7 mL) during 5 minutes. bis(tri-tert-butylphosphine)palladium (0) (59 mg, 0.116 mmol) was added and the reaction mixture was stirred under microwave irradiation during 10 minutes at 140° C. The reaction mixture was concentrated. The residue was purified by column chromatography on silica using a gradient from 0 till 10% $CH_3OH$ in $CH_2Cl_2$. The product fractions were concentrated and dried in vacuo, resulting in compound 122 yielding a beige powder (50 mg). Method E; Rt: 1.07 m/z: 523.2 $(M+H)^+$ Exact mass: 522.2

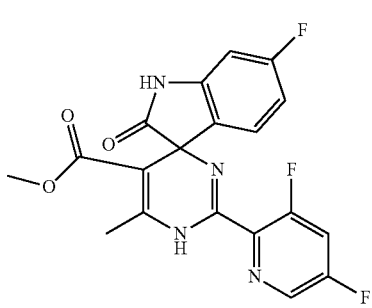
compound 123

Trifluoromethanesulfonic acid (0.1 mL) was added to a solution of compound 122 (23 mg) in dichloromethane (10 mL) and stirred at room temperature during 150 minutes. saturated $NaHCO_3$ (30 mL) solution was added and the mixture stirred vigorously during 10 minutes. The organic layer was dried over an HM-N cartridge and concentrated. The residue was purified by column chromatography on silica using a gradient from 0.5 till 10% $CH_3OH$ in dichloromethane. The product fractions were concentrated and dried in vacuo, resulting in compound 123 as a powder (10.4 mg) Method E; Rt: 0.80 m/z: 403.2 $(M+H)^+$ Exact mass: 402.1; $^1H$ NMR (400 MHz, CHLOROFORM-d) δ ppm 2.49 (s, 3H), 3.51 (s, 3H), 6.59 (dd, J=8.8, 2.2 Hz, 1H), 6.61-6.68 (m, 1H), 7.09-7.14 (m, 1H), 7.23-7.30 (m, 1H), 7.34 (bs, 1H), 8.29 (m, 2H)

Compound 103 (245 mg; 0.761 mmol), 2-amidinopyridiniumchloride (240 mg; 1.52 mmol), sodium bicarbonate (340 mg, 4.05 mmol) in DMF was stirred and heated for 2 hours at 80° C. The mixture was cooled to room temperature, diluted with $Et_2O$ and $H_2O$ and extracted with $Et_2O$. The combined organic phases where dried on $Na_2SO_4$. After filtration and evaporation of the solvent, the obtained residue (239 mg) was stirred at 90° C. for 2.5 hours in $POCl_3$ (5 mL). The volatiles were removed in vacuo, the obtained residue was dissolved in $CH_2Cl_2$ and stirred with saturated $NaHCO_3$ for 30 minutes. The mixture was extracted with $CH_2Cl_2$, dried on $Na_2SO_4$, and after filtration the solvent was removed. The black residue was dissolved in $CH_2Cl_2$ and filtered on a path of silica. After rinsing with $CH_2Cl_2$ the solvent was removed, resulting in a slightly yellow residue. This residue was stirred in a mixture of ethylene glycol dimethylether (5 mL), water (0.26 mL), morpholin-4-yl)methyltrifluoroborate internal salt (70 mg, 0.41 mmol) and $K_2CO_3$ (79 mg; 0.57 mmol). Nitrogen was bubbled through the mixture for 10 minutes and then bis(tri-t-Butylphosphine)palladium(0) (40.7 mg, 0.08 mmol) was added. The mixture was heated under microwave irradiation for 15 minutes at 140° C. $CH_2Cl_2$ was added, the mixture was washed with $H_2O$, and the water layer was extracted with $CH_2Cl_2$. The organic layer was dried on $Na_2SO_4$, filtered and concentrated in vacuo. The obtained residue was purified by column chromatography with heptane to heptane/EtOAc 50/50, resulting in compound 124 (35 mg).

Method E; Rt: 1.13 m/z: 457.2 $(M+H)^+$ Exact mass: 456.2

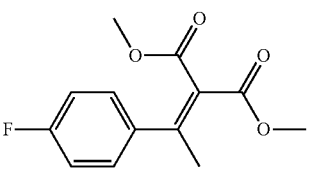
compound 125

A tube was charged with a stirring bar, dimethyl malonate (9.56 mL, 83.2 mmol), 4-fluorophenylacetylene (10 g, 83.2 mmol) and indium (III) chloride (550 mg, 2.49 mmol) and closed. The reaction mixture was then stirred in an oil bath at 130° C. for 18 hours and allowed to reach room temperature. The obtained reaction mixture was used as such in the next step.

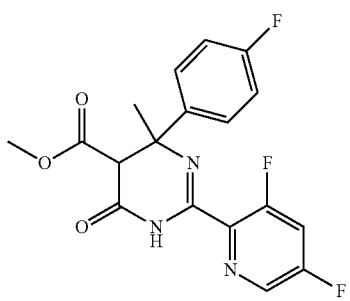

compound 126

A mixture of compound 125 (5 g of above obtained reaction mixture), 3,5-difluoro-2-pyridine carboximidamide acetate salt (6.46 g, 29.7 mmol) and sodium bicarbonate (3.33 g, 39.6) in 1,4-dioxane (100 mL) was stirred and heated at 60° C. for 1 hour. DMF (30 mL) was added and the reaction mixture was stirred further at 60° C. for 18 hours. The reaction mixture was concentrated in vacuo and the residue was poured into water. The organics were extracted with diethyl ether (3×200 mL) and the combined organic layers were dried (Na$_2$SO$_4$) and after filtration, concentrated to dryness. The obtained residue was purified using silica gel column chromatography (ethyl acetate in heptane from 10 to 50%) resulting in compound 126 (200 mg) Method A; Rt: 0.97 and 1.02 m/z: 378.1 (M+H)$^+$ Exact mass: 377.1.

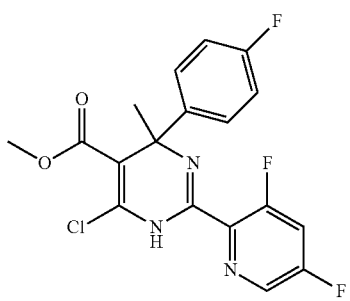

compound 127

Compound 126 (200 mg) was suspended in phosphorous oxychloride (1 mL, 10.8 mmol) and heated at 120° C. for 30 minutes. The reaction mixture was concentrated to dryness. The residue was stirred in cold saturated aqueous sodium bicarbonate solution for 10 minutes and extracted with CH$_2$Cl$_2$ (3×5 mL). The combined organic layers were dried (Na$_2$SO$_4$) and concentrated to dryness. The residue was purified using silica gel column chromatography (dichloromethane isocratic) to afford compound 127 (90 mg) as yellow powder. Method A; Rt: 1.07 m/z: 396.0 (M+H)$^+$ Exact mass: 395.1

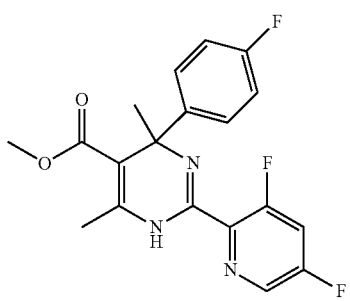

compound 128

Compound 127 (90 mg) was dissolved in dry DME (3 mL) in a microwave vial and nitrogen was bubbled through for 10 minutes. Then, tetramethyltin (270 μL, 0.195 mmol) was added followed by bis(tri-t-butylphosphine) palladium (0) (19.9 mg, 0.0389 mmol) and the vial was flushed with nitrogen and capped. The reaction mixture was heated under microwave irradiation at 140° C. for 20 minutes and allowed to reach room temperature. Then tetramethyltin (270 μL, 0.195 mmol) was added followed by bis(tri-t-butylphosphine) palladium (0) (19.9 mg, 0.0389 mmol) and the vial was flushed with nitrogen and capped. The reaction mixture was heated under microwave irradiation at 140° C. for 20 minutes and allowed to reach room temperature. The reaction mixture was evaporated and the residue was purified by Preperative HPLC on (RP SunFire Prep C18 OBD-10 μm, 30×150 mm). Mobile phase (0.1% TFA solution in water+5% acetonitrile, methanol). The desired fractions were combined, concentrated to dryness. The residue was neutralized with saturated aqueous sodium bicarbonate and extracted with dichloromethane (2×20 mL). The combined organic layers were dried (Na$_2$SO$_4$) and concentrated to dryness. The residue was co evaporated with methanol (2×5 mL). After drying in vacuo, compound 128 (14 mg) was obtained as a yellow solid. Method A; Rt: 1.04 m/z: 376.1 (M+H)$^+$ Exact mass: 375.1; $^1$H NMR (400 MHz, CHLOROFORM-d) d ppm 1.92 (s, 3H), 2.29 (s, 3H), 3.49 (s, 3H), 6.91-7.04 (m, 2H), 7.20-7.37 (m, 1H), 7.38-7.62 (m, 2H), 7.93 (br. s, 1H), 8.27 (d, J=2.0 Hz, 1H).

compound 129

A tube was charged with a stirring bar, dimethyl malonate (8.32 mL, 72.4 mmol), 3,4-fluorophenylacetylene (10.0 g, 72.4 mmol) and indium (III) chloride (479 mg, 2.16 mmol) and closed. The reaction mixture was then stirred at 130° C. for 18 hours and allowed to reach room temperature. The crude reaction mixture was used as such in the next reaction.

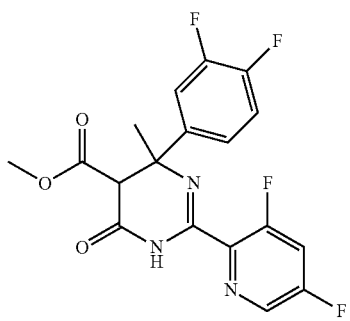

compound 130

Compound 129 (15 g of the above obtained reaction mixture), 3,5-difluoro-2-pyridine carboximidamide (11.3 g, 72 mmol) in DMF (100 mL) in a round bottom flask (250 mL) was and stirred at 40° C. for 20 hours. The solution was cooled to room temperature. The reaction mixture was poured into water (800 mL). The solids were filtered off and washed with water to afford sticky light orange gum. The gum was dissolved in dichloromethane, dried (Na$_2$SO$_4$) and evaporated to complete dryness resulting in a crude mixture containing compound 130 (15.6 g). Method A; Rt: 1.04 and 1.08 m/z: 396.0 (M+H)$^+$ Exact mass: 395.1;

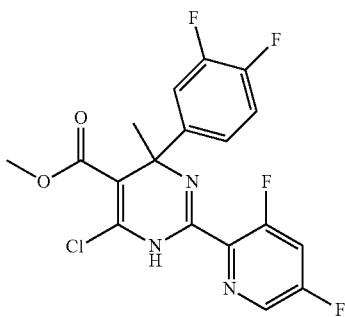

compound 131

Enantiomers of 131: 131a and 131b

A tube was loaded with a stirring bar, compound 130 (8.64 g) and phosphorous oxychloride (30 mL, 323 mmol) and the reaction mixture was heated at 110° C. for 2.5 hours and at room temperature for 18 hours. The reaction mixture was evaporated to dryness, toluene was added and the mixture was evaporated to afford a dark brown residue. The residue was dissolved in dichloromethane (200 mL) and washed with saturated aqueous sodium bicarbonate (150 mL). The water layer was extracted with dichloromethane (2×200 mL). The combined organic layers were washed with brine, dried (Na$_2$SO$_4$) and evaporated to dryness to afford dark brown oil. The oil was purified using silica gel column chromatography (isocratic dichloromethane) resulting in compound 131 (4.30 g). Method A; Rt: 1.11 m/z: 414.0 (M+H)$^+$ Exact mass: 413.1; Racemic mixture 131 was separated in its enantiomers 131a and 131b by preperative SFC (Stationary phase: Chiralcel Diacel OD 20×250 mm), Mobile phase: CO$_2$, Ethanol), yielding compound 131a (634 mg) and compound 131b (661 mg). OD-H 250 mm×4.6 mm; Flow: 3 mL/min; Mobile phase: 3% EtOH (containing 0.2% iPrNH$_2$) hold 15.00 min; Temperature: 30° C.; Compound 131a: Rt: 11.2 min; compound 131b: Rt: 12.1 min.

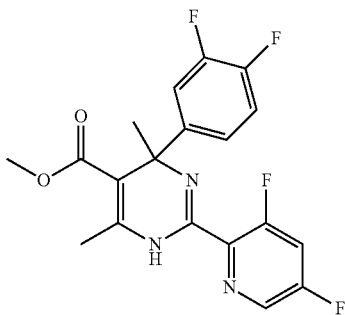

compound 132

Enantiomers of Racemic Mixture 132: 132a, 132b

A solution of compound 131 (1500 mg) in DMF (10 mL) in a microwave vial was stirred and nitrogen was bubbled through for 10 minutes. Then tetramethyltin (0.753 mL, 5.44 mmol) was added followed by bis(tri-t-butylphosphine) palladium (0) (185 mg, 0.363 mmol) and the vial was flushed with nitrogen and capped. The reaction mixture was heated under microwave irradiation at 140° C. for 30 minutes and allowed to reach room temperature. The reaction mixture was filtered and the filtrate was concentrated in vacuo. The residue was mixed with methanol (40 mL) and filtered. The filtrate was evaporated to dryness to afford an orange sticky residue which was purified using silica gel column chromatography (gradient ethyl acetate in heptane from 5 to 30% and isocratic dichloromethane) resulting in compound 132 (546 mg) as yellow solid. Method A; Rt: 1.09 m/z: 394.1 (M+H)$^+$ Exact mass: 393.1; $^1$H NMR (400 MHz, CHLOROFORM-d); ~9 to 1 tautomeric ratio; main tautomer described) δ ppm 1.89 (s, 3H), 2.30 (s, 3H), 3.52 (s, 3H), 7.05 (dt, J=10.2, 8.4 Hz, 1H), 7.20-7.24 (m, 1H), 7.27-7.35 (m, 2H), 7.98 (br. s., 1H), 8.29 (d, J=1.8 Hz, 1H). Racemix mixture 132 (230 mg) was separated in its enantiomers 132a and 132b, by preparative SFC (Chiralcel Diacel OJ 20×250 mm). Mobile phase (CO$_2$, Ethanol with 0.2% iPrNH$_2$), yielding compound 132a (79 mg) and compound 132b (83 mg) as sticky resins. Columns: OJ-H 250 mm×4.6 mm; Flow: 3 mL/min; Mobile phase: 3% EtOH (containing 0.2% iPrNH$_2$) hold 15.00 min; Temperature: 30° C.; Compound 132a Rt: 7.2 min; Compound 132b Rt: 8.7 min. Compound 132a: [α]$_D^{20}$: −19.7° (c 0.47 w/v %, DMF). Compound 132b: [α]$_D^{20}$: +20.3° (c 0.37 w/v %, DMF)

Mesylate Salt of Compound 132b

Compound 132b (3.01 g, 7.66 mmol), prepared similarly as described above, was dissolved in isopropanol (20 mL) and methanesulfonic acid (0.488 mL, 7.51 mmol) in isopropanol (5 mL) was added drop wise. The solution was heated at reflux while diisopropyl ether (250 mL) was added to the point of saturation. The compound crystallized from the refluxing solution and isopropanol (150 mL) was added. The solution was refluxed for 30 minutes and then cooled to room temperature. The formed precipitate was filtered off and washed with diisopropyl ether (10 mL) resulting in compound 132b. MsOH as a white solid which was dried in a vacuum oven at 50° C. $^1$H NMR (400 MHz, DMSO-d$_6$) δ ppm 2.03 (br. s, 3H), 2.27 (s, 3H), 2.29 (s, 3H), 3.50 (s, 3H), 7.40-7.46 (m, 1H), 7.46-7.57 (m, 1H), 7.61-7.81 (m, 1H), 8.37 (br. t, J=9.0 Hz, 1H), 8.79-8.86 (m, 1H), 11.92 (br. s., NH). Melting point (DSC; From 30 to 300° C. at 10° C./min): 196° C.

Compound 132b. (−)-camphanic acid

A solution of compound 131b (600 mg, 1.45 mmol) in DMF (5 mL) in a microwave-vial was stirred and purged with nitrogen for 10 minutes. Then, tetramethyltin (0.301 mL, 2.18 mmol) was added followed by bis(tri-t-butylphosphine) palladium (0) (148 mg, 0.29 mmol) and the vial was flushed with nitrogen and capped. The reaction mixture was heated at 140° C. by microwave-irradiation for 30 minutes and then allowed to reach room temperature. The reaction mixture was evaporated to dryness. The residue was dissolved in diethyl ether, washed with water and brine, dried (Na$_2$SO$_4$) and concentrated in vacuo. The obtained residue was purified twice using silica gel column chromatography (ethyl acetate in heptane from 10 to 30%) (Ethyl acetate in heptane from 10 to 25%). The desired fractions were concentrated to ~50 mL, the solids were filtered off and the filtrate was evaporated to dryness to afford compound 132b (287 mg) as a sticky oil. Compound 132b (287 mg, 0.73 mmol) and (−)-camphanic acid (145 mg, 0.73 mmol) were dissolved in boiling ethanol (10 mL). After cooling to room temperature, ethanol was evaporated, the solid was recrystallized from warm diisopropyl ether (12 mL) and the mixture was cooled overnight to room temperature. The solids were filtered and washed with cold diisopropyl ether. The crystals were dried at 50° C. in vacuo resulting in compound 132b. (−)-camphanic acid (221 mg) as a light yellow solid. $^1$H NMR (400 MHz, DMSO-d$_6$) δ ppm 0.84 (s, 3H), 1.00 (s, 6H), 1.44-1.60 (m, 1H), 1.76 (s, 3H), 1.84-2.03 (m, 2H), 2.18 (s, 3H), 2.27-2.41 (m, 1H), 3.43 (s, 3H), 7.17-7.43 (m, 3H), 8.05 (ddd, J=10.5, 9.0, 2.5 Hz, 1H), 8.58 (d, J=2.5 Hz, 1H), 9.55 (br. s., 1H), 13.52 (br. s, 1H)

compound 133

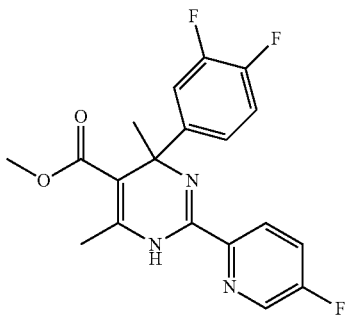

Compound 132 (88.5 mg, 0.22 mmol), potassium acetate (84.8 mg; 0.87 mmol) and Pd on carbon (10%; 100 mg) dissolved in methanol (50 mL) were stirred under hydrogen atmosphere during 105 minutes. The reaction mixture was filtered and concentrated. The residue was dissolved in CH$_2$Cl$_2$ (20 mL), washed with water, dried over an HM-N cartridge and concentrated. The residue was purified by column chromatography on silica using a gradient from 10 till 100% EtOAc in heptane. The product fractions were concentrated and the obtained residue, was dried in vacuo, resulting in compound 133 as a yellow resin (24.5 mg). Method D; Rt: 1.21 m/z: 376.1 (M+H)$^+$ Exact mass: 375.1 $^1$H NMR (400 MHz, DMSO-d$_6$, ~9 to 1 tautomeric mixture observed, main tautomer described) ppm 1.77 (s, 3H), 2.25 (s, 3H), 3.42 (s, 3H), 7.16-7.24 (m, 1H), 7.27-7.10 (m, 2H), 7.81 (td, J=8.8, 2.9 Hz, 1H), 8.09 (dd, J=8.9, 4.7 Hz, 1H), 8.58-8.66 (m, 1H), 9.47 (s, 1H).

compound 134

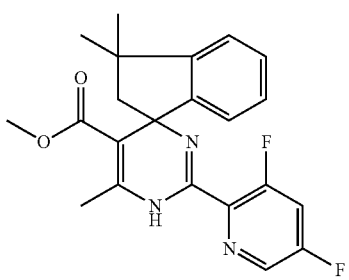

A microwave vial was loaded with a stirring bar, compound 92 (80 mg, 0.191 mmol) and DMF (dry) (1.22 mL, 15.7 mmol). Nitrogen was bubbled through for 10 minutes. Then tetramethyltin (39.8 μL, 0.287 mmol) was added followed by bis(tri-t-butylphosphine) palladium (0) (29.4 mg, 0.0574 mmol) and the vial was flushed with nitrogen and capped. The reaction mixture was heated under microwave irradiation at 140° C. for 10 minutes and allowed to reach room temperature. Nitrogen was bubbled through for 10 minutes. Then tetramethyltin (39.8 μL, 0.287 mmol) was added followed by bis(tri-t-butylphosphine) palladium (0) (29.4 mg, 0.0574 mmol) and the vial was flushed with nitrogen and capped. The reaction mixture was heated under microwave irradiation at 140° C. for 20 minutes. The reaction mixture was diluted with diethyl ether (50 mL) and washed with water (3×5 mL). The organic layer was dried (Na$_2$SO$_4$) and concentrated to dryness. The residue was purified twice using silica gel column chromatography (first purification: ethyl acetate in heptane from 5 to 50%; second CH$_2$Cl$_2$) and further purified by preperative SFC on (Chiralpak Diacel AD 30×250 mm). Mobile phase (CO$_2$, isopropanol with 0.2% isopropyl amine), the desired fractions were collected, evaporated, dissolved in methanol and evaporated again, yielding 134a (5.6 mg) and 134b (5 mg). SFC: Column: AD-H 250 mm×4.6 mm; Flow: 3 mL/min; Mobile phase: 10% iPrOH (containing 0.2% iPrNH$_2$) in CO$_2$, hold 15.00 min, Temperature: 30° C., Rt: Compound 134a: 6.4 min, 134b: 8.4 min compound 135

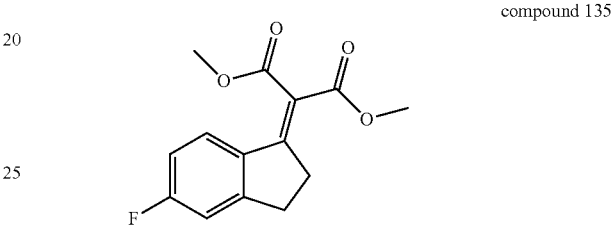

5-fluoro-2,3-dihydro-1H-inden-1-one (40 g, 266.4 mmol) and dimethyl malonate (42.2 g, 319.4 mmol) were dissolved in dry THF (1400 mL). TiCl$_4$ (101 g, 532.5 mmol) in dry CH$_2$Cl$_2$ (400 mL) was added dropwise at −20° C.~−10° C. under N$_2$. After addition, Pyridine (200 mL) was added dropwise at −20° C.~−10° C. under N$_2$. The mixture was stirred overnight at 20° C. The solid was filtered off. The cake was dissolved in ethyl acetate (800 mL), the suspension was stirred for 5 mins and filtered. The filtrate was concentrated in vacuo and ethyl acetate (800 mL) was added. The precipitate was filtered off. The filtrate was washed with brine (200 mL) and dried over Na$_2$SO$_4$. The solvent was removed under high vacuum. The residue was dissolved in DMSO (400 mL) filtered on filter paper, and next on a filter membrane (0.45 um). The obtained filtrate was purified by high-performance liquid chromatography (C18, eluent: CH$_3$CN/H$_2$O from 15/85 to 45/55 with 0.1% HCl as buffer). The pure fractions were concentrated in vacuo. The aqueous layer was extracted with dichloromethane (3×400 mL). The organic layer was washed with brine (200 mL) and dried over Na$_2$SO$_4$. The solvent was removed in vacuo, resulting in compound 135 (24 g).

compound 136

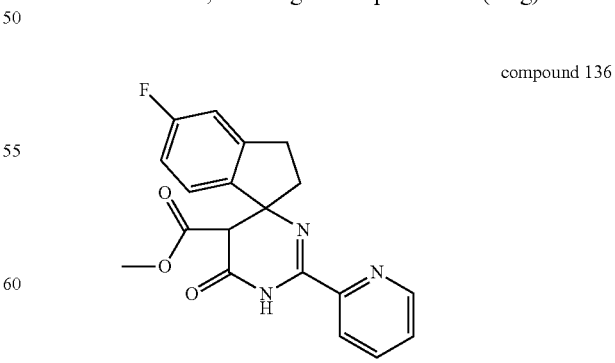

A mixture of compound 135 (6 g, 22.7 mmol), 2-amidinopyridiniumchloride (5.3 g, 33.6 mmol) and Na$_2$CO$_3$ (7.2 g, 67.9 mmol) in DMF (60 mL) was stirred overnight at 60° C.

under N₂. The solvent was removed in vacuo. The residue was suspended in dichloromethane (100 mL). The precipitate was filtered off. The solvent was removed in vacuo. The residue was purified by silica gel column chromatography. (Gradient eluent:petroleum ether:ethyl acetate: from 100:0 to 60:40), resulting in compound 136 (2.5 g) Method B; Rt: 1.04 m/z: 353.9 (M+H)⁺ Exact mass: 353.1.

compound 137

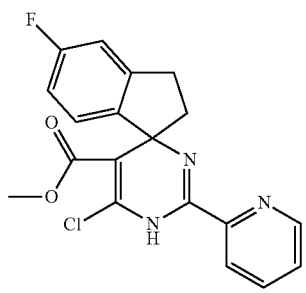

Compound 136 (2.5 g, 7.1 mmol) was stirred for 2 hours in POCl₃ (20 mL, 217 mmol) at 120° C. The reaction mixture was concentrated to dryness in vacuo. The residue was dissolved in dichloromethane (60 mL). The organic layer was washed with saturated aqueous NaHCO₃ (3×30 mL) and brine and dried over Na₂SO₄. The solvent was removed in vacuo. The residue was purified by silica gel column chromatography (gradient eluent:petroleum ether:ethyl acetate: from 100:0 to 70:30), resulting in compound 137 (1.4 g). Method B; Rt: 1.20 m/z: 372.0 (M+H)⁺ Exact mass: 371.1 compound 138

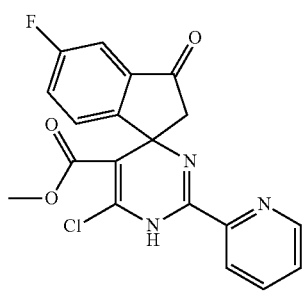

CrO₃ (34 mg, 0.34 mmol) and 70% aqueous t-BuOOH (3.02 mL) were dissolved in dry CH₂Cl₂ (4 mL). Compound 137 (385 mg, 1.03 mmol) in dry CH₂Cl₂ (4 mL) was added dropwise at room temperature under N₂. After addition, the mixture was stirred overnight at 20° C. The solid was filtered off. The filtrate was concentrated in vacuo and ethyl acetate (15 mL) was added. The resulting precipitate was filtered off. The filtrate was washed with brine (2×10 mL) and dried over Na₂SO₄. The solvent was removed in vacuo. The residue was purified by silica gel column chromatography (gradient eluent:petroleum ether:ethyl acetate: from 100:0 to 10:1) resulting in compound 138 (110 mg). Method B; Rt: 1.05 m/z: 385.9 (M+H)⁺ Exact mass: 385.1

Compound 139

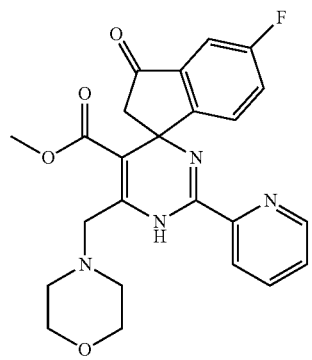

A mixture of compound 138 (0.1 g, 0.26 mmol), potassium (morpholin-4-yl)methyltrifluoroborate (0.11 g, 0.53 mmol), Pd(OAc)₂ (0.006 g, 0.027 mmol), butyldi-1-adamantylphosphine (CAS:321921-71-5; 0.015 g, 0.042 mmol) and Cs₂CO₃ (0.51 g, 1.56 mmol) in DME (1.4 mL) and H₂O (0.14 mL) was stirred under microwave irradiation for 20 min at 140° C. under N₂. Water (5 mL) and dichloromethane (5 mL) were added. The organic layer was separated and washed with water (2×5 mL). The organic layer was washed with 1 N HCl (5 mL). The aqueous layer was washed with dichloromethane (2×5 mL) and basified with NaHCO₃ to pH=7-8. The mixture was extracted with dichloromethane (15 mL). The organic layer was washed with brine and dried over Na₂SO₄. The residue was purified by preparative high performance liquid chromatography over RP-18 (eluent: CH₃CN in H₂O (0.1% TFA) from 20% to 60%, v/v). The pure fractions were collected and the solvent was removed in vacuo, resulting in compound 139 as a TFA salt (55 mg). Method G; Rt: 3.75 m/z: 451.2 (M+H)⁺ Exact mass: 450.2.

Compound 140

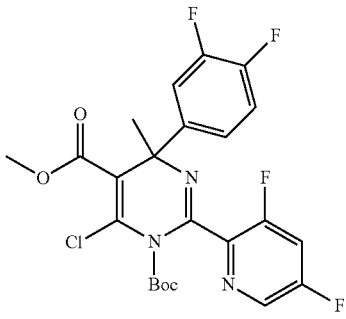

A vial was charged successively with compound 131 (2.80 g, 5.96 mmol), acetonitrile (25 mL, 481 mmol), 4-Dimethylaminopyridine (72.8 mg, 0.596 mmol) and di-tert-butyl dicarbonate (3.90 g, 17.9 mmol) and closed with a Teflon cap. The reaction mixture was stirred for 18 hours at room temperature. The reaction mixture was evaporated to dryness. The residue was purified using silica gel column chromatography (ethyl acetate in heptane from 10% to 20%) to afford compound 140 (2.73 g). Method A; Rt: 1.32 m/z: 514.1 (M+H)⁺ Exact mass: 513.1.

Compound 141

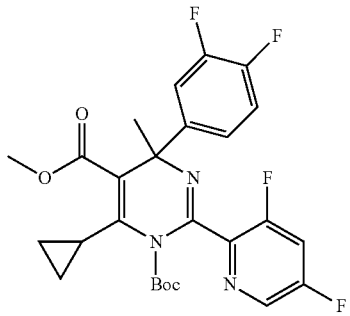

A tube was loaded with compound 140 (335 mg, 0.652 mmol), 1,4-dioxane (10 mL) and saturated aqueous potassium carbonate solution (5 mL). The reaction mixture was purged with nitrogen gas for 10 minutes and cyclopropyl trifluoroborate potassium salt (144 mg, 0.978 mmol) and dichloro[1,1'-bis(diphenylphosphino)ferrocene]palladium II dichloromethane adduct (26.6 mg, 0.0326 mmol) were added. The reaction mixture was flushed with nitrogen gas and the tube was closed, heated at 80° C. for 20 hours and allowed to reach room temperature. Dichloromethane (50 mL) was added to the reaction mixture. The separated organic layer was washed with saturated aqueous sodium carbonate solution (2×10 mL), water (5 mL) and Brine (5 mL). The organic solution was dried ($Na_2SO_4$) and evaporated. The residue was purified using silica gel column chromatography (ethyl acetate in heptane from 0% to 15%) to afford compound 141 (270 mg). Method A; Rt: 1.35 m/z: 520.1 (M+H)$^+$ Exact mass: 519.2.

Compound 142

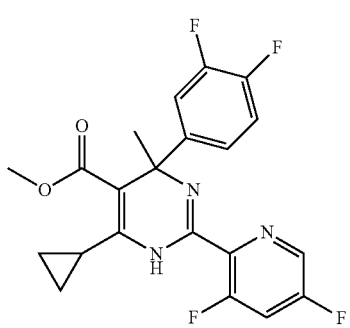

Compound 141 (270 mg) was dissolved in HCl (3 M in methanol) (20 mL, 60 mmol) and a stirring bar was added resulting in a bubbling solution. Part of the reaction mixture (~¼) was stirred at 45° C. for 1.5 hours in a closed tube. The solution was evaporated to dryness resulting in a sticky residue. Diethyl ether was added and evaporated to dryness. The residue was dissolved in dichloromethane (30 mL) and washed with saturated aqueous sodium bicarbonate (10 mL) and water (5 mL). The organic layer was dried ($Na_2SO_4$) and evaporated to dryness to afford compound 142 (50.5 mg). Method A; Rt: 1.24 m/z: 420.1 (M+H)$^+$ Exact mass: 419.1. $^1$H NMR (400 MHz, CHLOROFORM-d containing one drop of TFA) d ppm 0.76-0.94 (m, 2H), 1.07-1.23 (m, 2H), 2.17 (s, 3H), 2.31 (tt, J=8.6, 5.6 Hz, 1H), 3.63 (s, 3H), 7.15-7.29 (m, 2H), 7.33 (ddd, J=10.9, 7.2, 2.3 Hz, 1H), 7.58 (ddd, J=10.9, 7.1, 2.2 Hz, 1H), 8.51 (d, J=2.0 Hz, 1H).

Compound 143

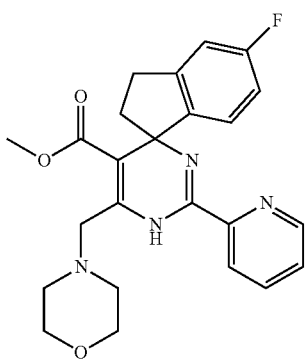

A mixture of compound 137 (150 mg, 0.403 mmol), potassium (morpholin-4-yl)methyltrifluoroborate (167 mg, 0.806 mmol), butyldi-1-adamantylphosphine (23 mg, 0.064 mmol), Pd(OAc)$_2$ (9 mg, 0.040 mmol) and Cs$_2$CO$_3$ (0.787 g, 2.418 mmol) in water (0.21 mL) and DME (2.1 mL) was heated by microwave irradiation for 20 minutes at 140° C. under N$_2$ atmosphere. Water (10 mL) and dichloromethane (10 mL) were added. The organic layer was separated and washed with water (10 mL). The organic layer was extracted with 1N HCl (5 mL). The aqueous layer was washed with dichloromethane (2×10 mL) and basified to pH=7-8 with NaHCO$_3$. The mixture was extracted with dichloromethane (2×10 mL). The combined organic layers were washed with brine and dried over Na$_2$SO$_4$. The solvent was removed in vacuo and the obtained residue was washed with petroleum ether (2 mL), resulting in compound 143 (120 mg). Method H; Rt: 3.28 m/z: 437.2 (M+H)$^+$ Exact mass: 436.2.

Compound 144

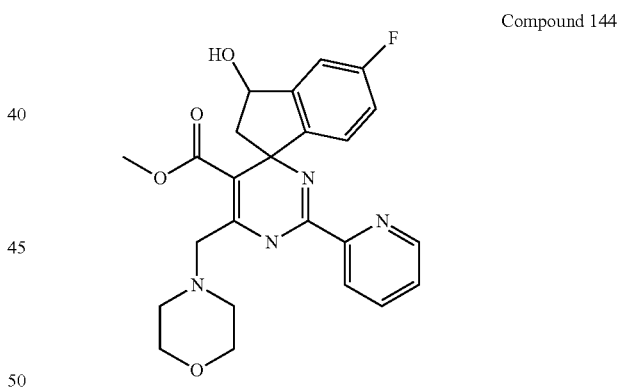

NaBH$_4$ (12.6 mg, 0.333 mmol) was added to compound 139 (50 mg) in MeOH (2 mL) and the resulting mixture was stirred for 10 minutes at 20° C. The solvent was removed in vacuo. Dichloromethane (10 mL) was added and the mixture was washed with water (2×10 mL). The organic layer was extracted with 1N HCl (2×10 mL). The combined aqueous layers were washed with dichloromethane (2×10 mL) and adjusted to pH=7-8 with solid NaHCO$_3$. The aqueous layer was extracted with dichloromethane (2×10 mL). The combined organic layers were washed with brine and dried over Na$_2$SO$_4$. The solvent was removed in vacuo. The residue was purified by preparative high performance liquid chromatography over RP-18 (eluent: CH$_3$CN in H$_2$O (0.1% TFA) from 15% to 25%, v/v). The pure fractions were collected and the volatiles were removed in vacuo. The aqueous layer was adjusted to pH=7 with Amberlite IRA-900 (OH) anionic exchange resin and the resin was filtered off. The aqueous layer was lyophilized to dryness resulting in compound 144 (20 mg). Method I Rt: 3.80 m/z; 453.3 (M+H)+ Exact mass: 452.2.

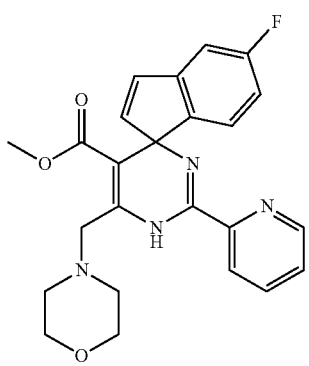

Compound 145

A mixture of compound 135 (12.5 g, 47.3 mmol), NBS (9.3 g, 52.3 mmol) and Benzoyl Peroxide (12 mg, 0.05 mmol) in $CCl_4$ (120 mL) was stirred overnight at 80° C. under $N_2$. The solvent was removed in vacuo. The residue was purified by silica gel chromatography. (gradient eluent:petroleum ether: ethyl acetate: from 200:1 to 100:1) resulting in a monobrominated derivative of compound 135 (7.2 g). A mixture of above obtained monobrominated derivative of compound 135 (3.6 g, 10.5 mmol), pyridine-2-carboximidamide hydrochloride (2.5 g, 16.0 mmol) and $Na_2CO_3$ (3.38 g, 31.9 mmol) in DMF (60 mL) was stirred for 4 hours at 90° C. under $N_2$. The solvent was removed in vacuo. The residue was suspended in dichloromethane (100 mL). The precipitate was filtered and the obtained filtrate concentrated in vacuo. The resulting residue was purified by silica gel column chromatography. (Gradient eluent:petroleum ether:ethyl acetate: from 50:1 to 1:5) resulting in methyl 5-fluoro-6'-oxo-2'-(pyridin-2-yl)-5',6'-dihydro-1'H-spiro[indene-1,4'-pyrimidine]-5'-carboxylate (0.4 g). methyl 5-fluoro-6'-oxo-2'-(pyridin-2-yl)-5',6'-dihydro-1'H-spiro[indene-1,4'-pyrimidine]-5'-carboxylate (0.6 g, 1.71 mmol) in $POCl_3$ (10 mL, 105.7 mmol) was stirred for 2 hours at 120° C. The reaction mixture was concentrated to dryness. The residue was dissolved in dichloromethane (10 mL). The organic layer was washed with saturated aqueous $NaHCO_3$ (3×30 mL) and brine and dried over $Na_2SO_4$. The solvent was removed in vacuo. The obtained residue was purified by silica gel column chromatography (gradient eluent:petroleum ether:ethyl acetate: from 100:0 to 70:30) resulting in methyl 6'-chloro-5-fluoro-2'-(pyridin-2-yl)-1'H-spiro[indene-1,4'-pyrimidine]-5'-carboxylate (0.07 g). A mixture of methyl 6'-chloro-5-fluoro-2'-(pyridin-2-yl)-1'H-spiro[indene-1,4'-pyrimidine]-5'-carboxylate (75 mg, 0.2 mmol), potassium (morpholin-4-yl)methyltrifluoroborate (84 mg, 0.41 mmol), $Pd(OAc)_2$ (45 mg, 0.2 mmol), butyldi-1-adamantyl-phosphine (11 mg, 0.033 mmol) and $Cs_2CO_3$ (390 mg, 1.20 mmol) in DME (1.4 mL) and $H_2O$ (0.14 mL) was heated by microwave irradiation for 20 minutes at 140° C. under $N_2$ atmosphere. Water (5 mL) and dichloromethane (5 mL) were added. The organic layer was separated and washed with water (2×5 mL). The organic layer was extracted with 1N HCl (5 mL). The aqueous layer was washed with dichloromethane (2×5 mL) and basified with $NaHCO_3$ to pH=7-8. The mixture was extracted with dichloromethane (15 mL). The organic layer was washed with brine and dried over $Na_2SO_4$. The solvent was removed in vacuo, resulting in compound 145 (12 mg). Method H; Rt: 3.29 m/z; 435.2 (M+H)+ Exact mass: 434.2. $^1$H NMR (400 MHz, CHLOROFORM-d) δ ppm 10.22 (1H, br. s), 8.61 (1H, d, J=4.5 Hz), 8.14 (1H, d, J=8.0 Hz), 7.71 (1H, td, J=7.5, 1.5 Hz), 7.36 (1H, ddd, J=7.5, 5.0, 1.5 Hz), 7.19 (1H, dd, J=8.0, 5.5 Hz), 6.97 (1H, dd, J=8.8, 2.5 Hz), 6.81 (1H, ddd, J=10.0, 8.0, 2.0 Hz), 6.65 (1H, d, J=5.5 Hz), 6.54 (1H, d, J=5.5 Hz), 3.82-3.89 (4H, m), 3.81 (1H, d, J=16.5 Hz), 3.73 (1H, d, J=16.5 Hz), 3.33 (3H, s), 2.57-2.71 (4H, m).

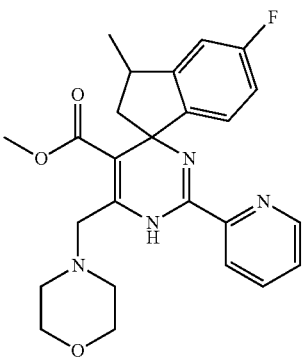

Compound 146

To the solution of 5-fluoro-3-methyl-2,3-dihydro-1H-inden-1-one (24 g, 146 mmol), and dimethyl malonate (57.9 g, 439 mmol) in $CH_2Cl_2$ (500 mL) and THF (500 mL) $TiCl_4$ (54.7 g, 292 mmol) was added dropwise at −40° C. The reaction mixture was stirred for 30 minutes at −40° C. Pyridine (57 g, 731 mmol) was added dropwise at −40° C. The reaction mixture was stirred for 12 hours at room temperature. The solid was filtered off and the filtrate was concentrated in vacuo. The obtained residue was purified by silica gel column chromatography (hexane:ethyl acetate=5:1), resulting in dimethyl 2-(5-fluoro-3-methyl-2,3-dihydro-1H-inden-1-ylidene)malonate (9.5 g). The mixture of dimethyl 2-(5-fluoro-3-methyl-2,3-dihydro-1H-inden-1-ylidene)malonate (9.2 g, 33.09 mmol), pyridine-2-carboximidamide (12 g, 99.2 mmol), $Na_2CO_3$ (10.5 g, 99.2 mmol) and 4 A molecular sieves (10 g) in $ClCH_2CH_2Cl$ (50 mL) was stirred for 12 hours at 80° C. under nitrogen atmosphere. The solvent was removed in vacuo and the obtained residue was purified by silica gel column chromatography (hexane:ethyl acetate=1:1) resulting in methyl 5-fluoro-3-methyl-6'-oxo-2'-(pyridin-2-yl)-2,3,5',6'-tetrahydro-1'H-spiro[indene-1,4'-pyrimidine]-5'-carboxylate (1.5 g). The mixture of methyl 5-fluoro-3-methyl-6'-oxo-2'-(pyridin-2-yl)-2,3,5',6'-tetrahydro-1'H-spiro[indene-1,4'-pyrimidine]-5'-carboxylate (1 g, 2.74 mmol) and $POCl_3$ (10 mL) was stirred for 5 hour under reflux. When the reaction was completed, the mixture was poured onto ice-water (20 mL) and extracted with ethyl acetate (3×10 mL). The combined layers were dried and concentrated to dryness. The obtained residue was purified by silica gel chromatography (hexane:ethyl acetate=1:1), resulting in methyl 6'-chloro-5-fluoro-3-methyl-2'-(pyridin-2-yl)-2,3-dihydro-1'H-spiro[indene-1,4'-pyrimidine]-5'-carboxylate (0.42 g). The mixture of methyl 6'-chloro-5-fluoro-3-methyl-2'-(pyridin-2-yl)-2,3-dihydro-1'H-spiro[indene-1,4'-pyrimidine]-5'-carboxylate (400 mg, 1.03 mmol), $Pd(OAc)_2$ (22 mg, 0.10 mmol), butyldi-1-adamantylphosphine (35.8 mg, 0.103 mmol), potassium (morpholin-4-yl)methyltrifluoroborate (256 mg, 1.23 mmol), $Cs_2CO_3$ (669 mg, 2.06 mmol), DME (10 mL) and $H_2O$ (1 mL) was stirred for 50 minutes under microwave irradiation at 140° C. The reaction mixture was concentrated in vacuo and the obtained residue was dissolved in ethyl acetate and washed with brine (2×10 mL). The organic layer was concentrated to dryness. The crude product was purified by preparative high-performance chromatography (eluent: CH$_3$CN/H$_2$O=30/70 to 80/20, 0.1% CF$_3$COOH). The desired fraction was collected and the pH value of the solution was adjusted to about 8 with K$_2$CO$_3$. Then, the organic solvent was removed under reduced pressure. The aqueous layer was extracted with ethyl acetate (3×20 mL). The organic layers were combined and dried over Na$_2$SO$_4$. The solution was evaporated and the pure product was dried in vacuo resulting in compound 146 (60 mg, 7/3 diastereomeric mixture). Method J; Rt: 6.44 m/z; 451.2 (M+H)$^+$ Exact mass: 450.2.

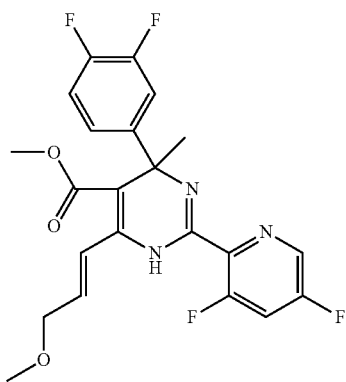

compound 147

Nitrogen was bubbled through a solution of compound 140 (130 mg, 0.24 mmol) and saturated potassium carbonate solution (2.5 mL) in dioxane (4 mL) during 10 minutes. Potassium trans-3-methoxy-1-propenyltrifluoroborate (64 mg, 0.36 mmol) and dichloro[1,1'-bis(diphenylphosphino) ferrocene] palladium (II) dichloromethane adduct (9.8 mg, 0.012 mmol) were added and the reaction mixture was heated at 80° C. in a closed tube during 2 hours. The reaction mixture was concentrated. The residue was dissolved in CH$_2$Cl$_2$ (30 mL) and water (20 mL). The organic layer was dried over an HM-N cartridge and concentrated. The residue was purified by column chromatography on silica (eluent 5 to 100% EtOAc in heptane). The product fractions were combined and concentrated yielding (E)-1-tert-butyl 5-methyl 4-(3,4-difluorophenyl)-2-(3,5-difluoropyridin-2-yl)-6-(3-methoxyprop-1-enyl)-4-methylpyrimidine-1,5(4H)-dicarboxylate as a clear oil (94 mg). HCl in dioxane (1 mL, 4 M) was added to a solution of the above compound (94 mg) in methanol (5 mL) and stirred overnight at room temperature. The reaction mixture was concentrated and dried in vacuo overnight. The obtained residue was dissolved in CH$_2$Cl$_2$ (5 mL), washed with saturated NaHCO$_3$ (5 mL), the organic layer dried over an HM-N cartridge and concentrated in vacuo. The obtained residue was dried overnight in vacuo at 50° C. yielding compound 147 (61 mg) as a yellow resin. Method K; Rt: 2.20 m/z; 450.2 (M+H)$^+$ Exact mass: 449.1.

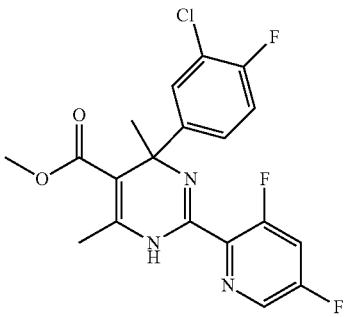

compound 148

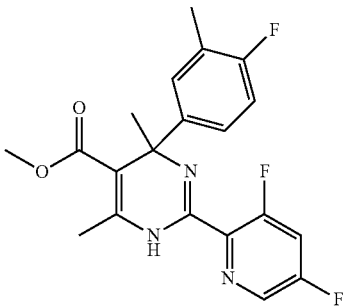

compound 149

A vial was charged with 3-chloro-4-fluorophenylacetylene (6 g, 38.8 mmol), dimethyl malonate (4.4 mL, 38.8 mmol) and indium(III) chloride (257 mg, 1.16 mmol). The mixture was stirred at 130° C. for 18 hours, allowed to reach room temperature and used as such. Part of this reaction mixture (4.21 g crude mixture) and 3,5-difluoropicolinimidamide (3.46 g, 22 mmol) in 1,4-dioxane (63 mL) was stirred and heated at 40° C. for 90 minutes. The resulting reaction mixture was concentrated under reduced pressure, phosphorus oxychloride (27.3 mL, 293.81 mmol) was added and this mixture was heated and stirred in an oil bath at 110° C. for 7 hours. The resulting mixture was concentrated under reduced pressure. The obtained residue was treated with sodium bicarbonate (aq sat 150 mL) and stirred for 30 minutes. This was extracted with dichloromethane (3×100 mL). The combined organics were dried on Na$_2$SO$_4$, filtered and concentrated under reduced pressure. The crude was purified using silica gel column chromatography (gradient: Heptane-dichloromethane 60:40 to 40:60). The desired fractions were concentrated under reduced pressure. The obtained crude was purified again using silica column chromatography (gradient: heptane-ethyl acetate 100:0 to 90:10) yielding methyl 6-chloro-4-(3-chloro-4-fluorophenyl)-2-(3,5-difluoropyridin-2-yl)-4-methyl-1,4-dihydropyrimidine-5-carboxylate (774 mg) as a yellow solid. This compound (500 mg, 1.16 mmol) was dissolved in N,N-dimethylformamide (5 mL) and the solution was purged with nitrogen for 10 minutes. Then, tetramethyltin (322 µl, 2.32 mmol) was added followed by bis(tri-t-butylphosphine)palladium(0) (59.4 mg, 0.12 mmol), the vial was flushed with nitrogen and capped. The mixture was heated by microwave-irradiation at 140° C. for 60 minutes. The mixture was evaporated to dryness in vacuo. The obtained residue was dissolved in diethyl ether and the organic layer was washed with distilled water (3×10 mL). The organic layer was dried over Na$_2$SO$_4$ and concentrated under reduced pressure. The crude was purified by Prep HPLC (Hypersyl C$_{18}$ BDS-3 µm, 100×4.6 mm) Mobile phase (NH$_4$OAc 0.5% in water, ACN). The desired fractions were collected, the organic solvent removed in vacuo and the waterlayer extracted with dichloromethane.

The organic layers were combined and concentrated under reduced pressure, yielding compound 148 (211 mg) and compound 149 (29 mg) as a yellow solid.

Compound 148 Method A; Rt: 1.13 m/z; 410.1 (M+H)$^+$ Exact mass: 409.1.

Compound 149 Method A; Rt: 1.09 m/z; 390.1 (M+H)$^+$ Exact mass: 389.1.

Compound 150

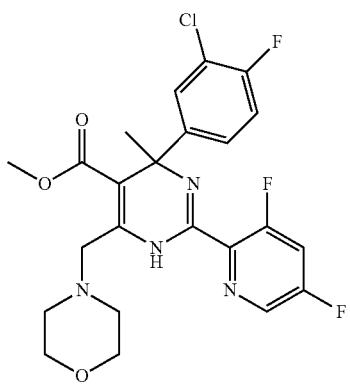

A microwave vial was charged with methyl 6-chloro-4-(3-chloro-4-fluorophenyl)-2-(3,5-difluoropyridin-2-yl)-4-methyl-1,4-dihydropyrimidine-5-carboxylate (478 mg, 1.11 mmol), cesium carbonate (2.18 g, 6.68 mmol), potassium (morpholin-4-yl)methyltrifluoroborate (276.5 mg, 1.34 mmol), distilled water (1 mL) and 1,2-dimethoxyethane (3 mL). The mixture was purged with nitrogen for 5 minutes. Then palladium(II) acetate (50.4 mg, 0.22 mmol) and butyldi-1-adamantylphosphine (63.8 mg, 0.18 mmol) were added and the mixture was purged with nitrogen for another 2 minutes. The vial was capped and heated by microwave irradiation at 100° C. for 25 minutes. The mixture was cooled to room temperature and taken up in dichloromethane (5 mL) and water (5 mL). The layers were separated and the water layer was extracted with dichloromethane (2×5 mL). The combined extracts were dried over Na$_2$SO$_4$, filtered and concentrated under reduced pressure. The obtained crude was purified by Prep HPLC (Hypersyl C18 BDS-3 μm, 100×4.6 mm) Mobile phase (NH$_4$OAc 0.5% in water/acetonitrile). The desired fractions were collected, the organic solvent removed in vacuo and the obtained water was extracted with dichloromethane (2×10 mL). The combined organic layers were dried on Na$_2$SO$_4$ and concentrated under reduced pressure yielding compound 150. Method A; Rt: 1.22 m/z; 495.1 (M+H)$^+$ Exact mass: 494.1.

Compound 151

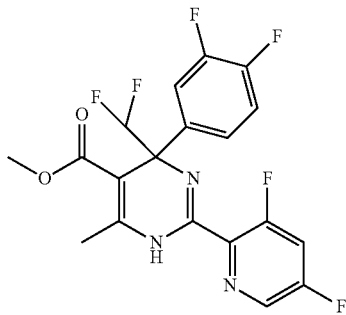

Enantiomers of Racemic Mixture 151: 151a and 151b

Titanium tetrachloride (11.4 mL, 104.1 mmol) in dichloromethane (28 mL) was added dropwise to a flask containing tetrahydrofuran (205 mL) under a nitrogen atmosphere, cooled in icebath. Then 1-(3,4-difluorophenyl)-2,2-difluoroethanone (10 g, 52 mmol) and dimethyl malonate (5.93 mL, 52 mmol) were added both at once. The resulting mixture was stirred under nitrogen atmosphere for 60 minutes while cooling was continued. Then, pyridine (16.8 mL, 208 mmol) in tetrahydrofuran (37 mL) was added to the mixture and this was allowed to warm to room temperature and stirred overnight. Next, distilled water (40 mL) and diethylether (40 mL) were added to the mixture. The layers were separated and the aqueous layer was extracted with diethylether (2×40 mL). The combined organics were washed with brine (60 mL), NaHCO$_3$ (60 mL) (aq/sat) and again with brine (60 mL). The organic layer was dried on MgSO$_4$, filtered and concentrated under reduced pressure yielding dimethyl 2-(1-(3,4-difluorophenyl)-2,2-difluoroethylidene)malonate (15.6 g) as a clear oil. Dimethyl 2-(1-(3,4-difluorophenyl)-2,2-difluoroethylidene)malonate (5 g) was dissolved in 1,4-dioxane (25 mL) and treated with 3,5-difluoropyridine-2-carboximidamide (3.1 g, 19.6 mmol). The resulting mixture was stirred at 40° C. overnight. The mixture was concentrated under reduced pressure and the obtained residue was purified by silica gel column chromatography (ethyl acetate-heptane 0:100 to 50:50) yielding methyl 4-(difluoromethyl)-4-(3,4-difluorophenyl)-2-(3,5-difluoropyridin-2-yl)-6-oxo-1,4,5,6-tetrahydropyrimidine-5-carboxylate (5.45 g) as a yellow solid which was used as such. Methyl 4-(difluoromethyl)-4-(3,4-difluorophenyl)-2-(3,5-difluoropyridin-2-yl)-6-oxo-1,4,5,6-tetrahydropyrimidine-5-carboxylate was treated with phosphorus oxychloride (10 mL, 107.6 mmol) and the mixture was stirred at reflux for 2 hours.

The mixture was concentrated under reduced pressure yielding a black tar which was treated with ice-water (50 mL). This was extracted with dichloromethane (3×30 mL). The combined extracts were washed with brine (30 mL), dried on MgSO$_4$, filtered and concentrated under reduced pressure. The obtained crude was purified by silica gel chromatography using gradient elution (heptanes-dichloromethane 100:0 to 25:75) yielding methyl 6-chloro-4-(difluoromethyl)-4-(3,4-difluorophenyl)-2-(3,5-difluoropyridin-2-yl)-1,4-dihydropyrimidine-5-carboxylate (1.95 g) as a slightly yellow solid which was used as such. Methyl 6-chloro-4-(difluoromethyl)-4-(3,4-difluorophenyl)-2-(3,5-difluoropyridin-2-yl)-1,4-dihydropyrimidine-5-carboxylate (450 mg, 1 mmol) was dissolved in N,N-dimethylformamide (6.4 mL) in a microwave-vial and this was purged with nitrogen for 10 minutes. Then tetramethyltin (0.21 mL, 1.5 mmol) was added followed by bis(tri-t-butylphosphine)palladium(0) (51 mg, 0.1 mmol) and the vial was flushed with nitrogen and capped. The mixture was heated by microwave irradiation at 140° C. for 10 minutes. The mixture was concentrated in vacuo and co-evaporated with toluene (2×20 mL). The obtained residue was taken up in water-dichloromethane (30 mL-30 mL) and the water layer was extracted another two times (2×30 mL dichloromethane). The combined extract were dried on Na$_2$SO$_4$, filtered and concentrated under reduced pressure. The residue was purified by Prep HPLC (Hypersyl C$_{18}$ BDS-3 μm, 100×4.6 mm) Mobile phase (NaHCO$_3$ 0.5% in water, CH$_3$CN). The desired fractions were concentrated and co-evaporated with methanol (2×10 mL). The obtained residue was dried in in vacuo, yielding compound 151 as a yellow oil. Racemic mixture 151 was separated in enantiomers 151a and 151b using preparative SFC (Stationary phase: Chiralcel Diacel OJ 20×250 mm/mobile phase: CO$_2$, EtOH with 0.2% iPrNH$_2$) yielding Compound 151a (93 mg) as a yellow sticky solid and compound 151b (100 mg) as a yellow sticky solid. Compound 151: Method A; Rt: 1.11 m/z; 430.0 (M+H)$^+$ Exact mass: 429.1. $^1$H NMR (400 MHz, CHLOROFORM-d, tautomeric mixture, main isomer described) δ ppm 2.36 (s, 3H), 3.69 (s, 3H), 6.71 (t, J=56 Hz, 1H), 7.07 (dt, J=10.0, 8.5 Hz, 1H), 7.26-7.31 (m, 1H), 7.32-7.43 (m, 2H), 8.29 (d, J=2.0 Hz, 1H), 8.34 (br. s., 1H). SFC: column: OJ-H 250 mm×4.6 mm; Flow: 3 mL/min; Mobile phase: 5% EtOH (containing 0.2% iPrNH$_2$) hold 15.00 min, Temperature: 30° C.: Compound 151a Rt: 3.9 min; Compound 151b Rt: 4.4 min)

Compound 152

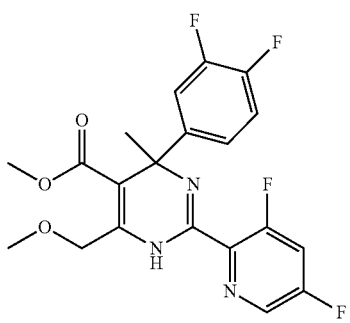

A solution of compound 131 (180 mg, 0.435 mmol) in DMF (2 mL) in a microwave-vial was stirred and purged with nitrogen for 10 minutes. Then, tributyl(methoxymethyl)stannane (219 mg, 0.653 mmol) was added followed by bis(tri-t-butylphosphine)palladium(0) (44.5 mg, 0.087 mmol) and the vial was flushed with nitrogen and capped. The reaction mixture was heated by microwave-irradiation at 140° C. for 30 minutes and allowed to reach room temperature. The reaction mixture was concentrated in vacuo to afford a sticky oil. This oil was purified using prep. HPLC (Hypersyl C$_{18}$ BDS-3 μm, 100×4.6 mm; Mobile phase (NH$_4$HCO$_3$ 0.2% in water, acetonitrile). The desired fractions were combined and evaporated to form a precipitate in the remaining solvent (water). The solids were filtered and washed with water resulting in compound 152 (23 mg) as off-white solid after drying in vacuo at 50° C. Method A; Rt: 1.18 m/z; 424.1 (M+H)$^+$ Exact mass: 423.1. $^1$H NMR (400 MHz, CHLOROFORM-d) δ ppm 1.92 (s, 3H), 3.49 (s, 3H), 3.51 (s, 3H), 4.61 (d, J=16.0 Hz, 1H), 4.67 (d, J=16.0 Hz, 1H), 7.06 (dt, J=10.0, 8.5 Hz, 1H), 7.15-7.22 (m, 1H), 7.24-7.33 (m, 2H), 8.33 (d, J=2.0 Hz, 1H), 9.04 (br. s, 1H).

Compound 153

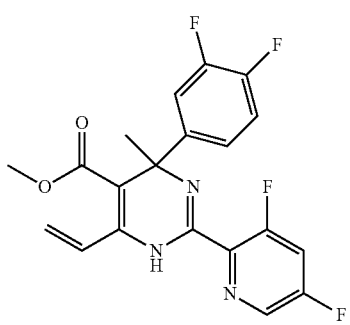

A tube was loaded with compound 140 (150 mg, 0.277 mmol), 1,4-dioxane (4 mL) and saturated aqueous potassium carbonate solution (3 mL). The reaction mixture was purged with nitrogen gas for 10 minutes and potassium vinyltrifluoroborate (55.7 mg, 0.416 mmol) and dichloro[1,1'-bis(diphenylphosphino) ferrocene]palladium II dichloromethane adduct (11.3 mg, 0.0139 mmol) were added. The reaction mixture was flushed with nitrogen gas and the tube was closed and heated at 80° C. for 20 hours and allowed to reach room temperature. Dichloromethane (25 mL) was added to the reaction mixture. The separated organic layer was washed with saturated aqueous sodium carbonate solution (2×5 mL), water (5 mL) and brine (5 mL). The organic solution was dried (Na$_2$SO$_4$) and evaporated. The residue was purified using silica gel column chromatography (ethyl acetate in heptane from 0% to 15%) to afford 1-tert-butyl 5-methyl 4-(3,4-difluorophenyl)-2-(3,5-difluoropyridin-2-yl)-4-methyl-6-vinylpyrimidine-1,5(4H)-dicarboxylate (60 mg) as yellow sticky oil which was dried in vacuum oven at 40° C. overnight and used as such in the next step. Method A; Rt: 1.30 m/z; 506.1 (M+H)$^+$ Exact mass: 505.2. 1-tert-butyl 5-methyl 4-(3,4-difluorophenyl)-2-(3,5-difluoropyridin-2-yl)-4-methyl-6-vinylpyrimidine-1,5(4H)-dicarboxylate (60 mg, 0.119 mmol), HCl (4M in dioxane) (4.00 mL, 16.0 mmol) and methanol (2 mL) was stirred at 50° C. for 1 hour. The reaction mixture was concentrated to dryness to afford a yellow sticky residue which was purified using silica gel column chromatography (dichloromethane in heptane from 40 to 100%) to afford compound 153 (41 mg) after drying in vacuo. Method A; Rt: 1.18 m/z; 406.1 (M+H)$^+$ Exact mass: 405.1.

Compound 154

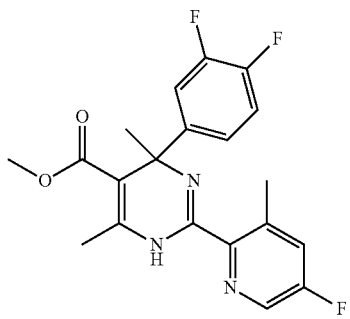

A solution of compound 132 (75 mg, 0.183 mmol) in DMF (1 mL) in a microwave-vial was stirred and purged with nitrogen for 10 minutes. Then tetramethyltin (38.0 μL, 0.275 mmol) was added followed by bis(tri-t-butylphosphine)palladium(0) (18.7 mg, 0.0366 mmol) and the vial was flushed with nitrogen and capped. The reaction mixture was heated by microwave irradiation at 140° C. for 1 hour and allowed to reach room temperature. The reaction mixture was concentrated in vacuo to afford a dark resin. The product was mixed with methanol (10 mL) and filtered. The filtrate was evaporated to dryness to afford a dark oily residue. The oil was dissolved in dichloromethane (30 mL), washed with water (2×10 mL), brine (5 mL), dried (Na$_2$SO$_4$), filtered and evaporated to afford a brown oil. The oil was purified using silica gel column chromatography (ethyl acetate in heptane from 5 to 30%). All fractions containing the desired product were combined and concentrated in vacuo to afford compound 154 as yellow sticky oil. Method A; Rt: 1.17 m/z; 390.1 (M+H)$^+$ Exact mass: 389.1. $^1$H-NMR (600 MHz, benzene-d$_6$); tautomeric mixture (~9/1), main isomer described; ppm 1.90 (s, 3H), 2.00 (s, 3H), 2.34 (t, J=0.6 Hz, 3H), 3.18 (s, 3H), 6.52 (ddd, J=9.1, 2.8, 0.7 Hz, 1H), 6.81 (dt, J=10.2, 8.5 Hz, 1H), 7.14-7.18 (m, 1H), 7.50 (ddd, J=12.2, 7.8, 2.3 Hz, 1H), 7.91 (d, J=2.8 Hz, 1H), 8.21 (br. s., 1H)

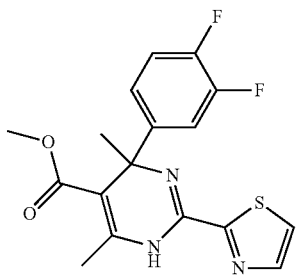

Compound 155

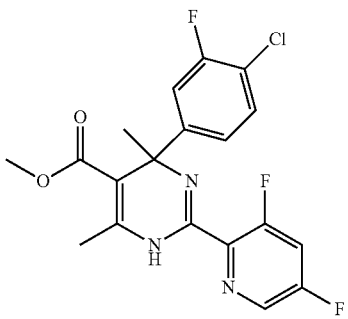

Compound 156

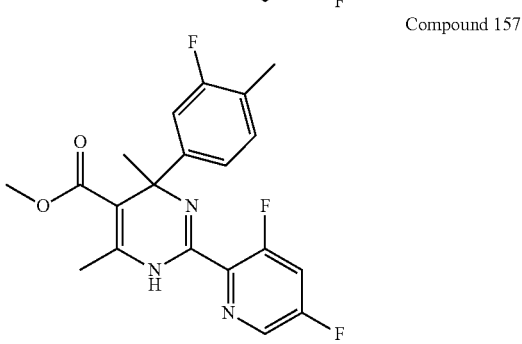

Compound 157

Enantiomers of Racemic Mixture 155: 155a and 155b

A mixture of compound 129 (2 g, 6.29 mmol) and 2-thiazolecarboximidamide (1.04 g, 8.18 mmol) in DMF (10 mL) was stirred and heated at 60° C. for 6 hours. The reaction mixture was poured into water and the precipitate was filtered and dissolved in dichloromethane. The organic solvent was dried ($Na_2SO_4$) and concentrated to dryness in vacuo, resulting in a crude mixture containing methyl 4-(3,4-difluorophenyl)-4-methyl-6-oxo-2-(thiazol-2-yl)-1,4,5,6-tetrahydropyrimidine-5-carboxylate (1.91 g). Method A; Rt: 1.04 m/z; 366.0 (M+H)$^+$ Exact mass: 365.1. A mixture of methyl 4-(3,4-difluorophenyl)-4-methyl-6-oxo-2-(thiazol-2-yl)-1,4,5,6-tetrahydropyrimidine-5-carboxylate (1.91 g crude) and $POCl_3$ (7 mL, 78 mmol) in a closed tube was stirred at 120° C. for 75 minutes. The reaction mixture was concentrated under a nitrogen flow at 50° C. The obtained residue was dissolved in dichloromethane (50 mL) and washed with saturated aqueous sodium bicarbonate (50 mL). The organic phase was dried ($Na_2SO_4$) and concentrated in vacuo to afford a dark brown residue. The obtained residue was purified using silica gel column chromatography (isocratic dichloromethane) resulting in methyl 6-chloro-4-(3,4-difluorophenyl)-4-methyl-2-(thiazol-2-yl)-1,4-dihydropyrimidine-5-carboxylate (721 mg crude). Method A; Rt: 1.10 m/z; 384.0 (M+H)$^+$ Exact mass: 383.0. A solution of methyl 6-chloro-4-(3,4-difluorophenyl)-4-methyl-2-(thiazol-2-yl)-1,4-dihydropyrimidine-5-carboxylate (356 mg, 0.751 mmol) in DMF (2 mL) in a microwave-vial was stirred and purged with nitrogen for 10 minutes. Tetramethyltin (156 µL, 1.13 mmol) was added followed by bis(tri-t-butylphosphine) palladium (0) (76.8 mg, 0.15 mmol), the vial was flushed with nitrogen and capped. The reaction mixture was heated by microwave-irradiation at 140° C. for 30 minutes and allowed to reach room temperature. The reaction mixture was evaporated to dryness. The residue was dissolved in dichloromethane and washed with water and brine, dried ($Na_2SO_4$) and evaporated to dryness to afford a brown oil. The obtained crude was purified using silica gel column chromatography (ethyl acetate in heptane from 10 to 30%) to afford compound 155 (153 mg). Method A; Rt: 1.12 m/z; 364.1 (M+H)$^+$ Exact mass: 363.1. $^1$H NMR (400 MHz, CHLOROFORM-d, tautomeric mixture (~8/2), major isomer described) δ ppm 1.87 (s, 3H), 2.29 (s, 3H), 3.49 (s, 3H), 7.06 (dt, J=10.0, 8.5 Hz, 1H), 7.13-7.20 (m, 1H), 7.23-7.32 (m, 1H), 7.44 (d, J=3.0 Hz, 1H), 7.73 (br. s., 1H), 7.82 (d, J=3.0 Hz, 1H). Racemic mixture 155 was separated in enantiomers 155a and 155b by Prep SFC (Stationary phase: Chiralpak Diacel AD 30×250 mm), Mobile phase: $CO_2$, Ethanol), yielding compound 155a (54 mg) and compound 155b (50 mg). Columns: AD-H 250 mm×4.6 mm; Flow: 3 mL/min; Mobile phase: 5% EtOH (containing 0.2% iPrNH$_2$) hold 15.00 min; Temperature: 30° C. compound 155a Rt (4.0 min) compound 155b Rt (4.9 min).

Prepared via a similar route as described for compound 148 and 149, starting from 1-chloro-4-ethynyl-2-fluoro-benzene instead of 3-chloro-4-fluorophenylacetylene. The reaction of dimethyl 2-(1-(3-chloro-4-fluorophenyl)ethylidene)malonate with 3,5-difluoropicolinimidamide in 1,4-dioxane was performed at 40° C. for 18 hours. Compound 156: Method A; Rt: 1.13 m/z; 410.1 (M+H)$^+$ Exact mass: 409.1; $^1$H NMR (400 MHz, CHLOROFORM-d, containing one drop of TFA) δ ppm 2.22 (s, 3H), 2.50 (s, 3H), 3.60 (s, 3H), 7.28 (ddd, J=8.4, 2.4, 0.7 Hz, 1H), 7.33 (dd, J=9.7, 2.2 Hz, 1H), 7.47 (dd, J=8.4, 7.5 Hz, 1H), 7.57 (ddd, J=10.8, 7.0, 2.2 Hz, 1H), 8.49 (d, J=2.2 Hz, 1H)

Compound 156. MsOH: Prepared similar to compound 132b, starting from compound 156 instead of 132b Compound 157 Method A; Rt: 1.09 m/z; 390.1 (M+H)$^+$ Exact mass: 389.1

$^1$H NMR (400 MHz, CHLOROFORM-d, containing one drop of TFA) δ ppm 2.20 (s, 3H), 2.29 (d, J=1.8 Hz, 3H), 2.48 (s, 3H), 3.58 (s, 3H), 7.13-7.21 (m, 2H), 7.22-7.29 (m, 1H), 7.56 (ddd, J=10.8, 7.2, 2.2 Hz, 1H), 8.49 (d, J=2.0 Hz, 1H)

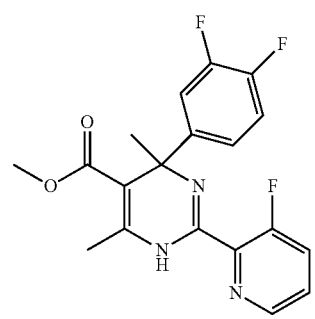 [SMILES: COC(=O)C1=C(C)NC(c2ncccc2F)=NC1(C)c1ccc(F)c(F)c1]

Enantiomers of Racemic Mixture 158: 158a and 158b

Compound 158 was prepared via a similar route as described for compound 132 from compound 129, using 3-fluoro-2-pyridine carboximidamide instead of 3,5-difluoro-2-pyridine carboximidamide. $^1$H NMR (400 MHz, CHLOROFORM-d, tautomeric mixture (~9/1), main isomer described) δ ppm 1.90 (s, 3H), 2.30 (s, 3H), 3.52 (s, 3H), 7.05 (dt, J=10.0, 8.0 Hz, 1H), 7.20-7.26 (m, 1H), 7.33 (ddd, J=12.0, 8.0, 2.0 Hz, 1H), 7.41 (ddd, J=8.0, 4.5, 3.5 Hz, 1H), 7.50 (ddd, J=10.0, 8.5, 1.5 Hz, 1H), 8.16 (br. s., 1H), 8.38 (dt, J=4.6, 1.3 Hz, 1H). Racemic mixture 158 (135 mg) was separated in enantiomers 158a and 158b by Prep SFC on (Chiralpak Diacel AD 30×250 mm). Mobile phase (CO$_2$, Ethanol), the desired fractions were collected, evaporated, dissolved in methanol and evaporated again, yielding compound 158a and compound 158b. Columns: AD-H 250 mm×4.6 mm, Flow: 3 mL/min; Mobile phase: 3% EtOH (containing 0.2% iPrNH$_2$) hold 17.5 min; Temperature: 30° C.; compound 158a Rt (7.2 min; 376.1 (M+H)$^+$), compound 158b Rt (8.6 min; 376.1 (M+H)$^+$).

centrated in vacuo. The obtained residue was purified using silica gel column chromatography (ethyl acetate in heptane from 20 to 100%) to afford compound 159 as yellow sticky oil. Method A; Rt: 0.86 m/z; 359.2 (M+H)$^+$ Exact mass: 358.1. Racemix mixture 159 was purified by Prep SFC (Stationary phase: Chiralpak Diacel AD 30×250 mm), Mobile phase: CO$_2$, Ethanol), yielding compound 159a and 159b as yellow powders. Columns: AD-H 250 mm×4.6 mm; Flow: 3 ml/min; Mobile phase: 10% EtOH (containing 0.2% iPrNH$_2$) hold 15.00 min; Temperature: 30° C.; compound 159a: Rt (3.2 min), compound 159b Rt (4.5 min). $^1$H NMR (360 MHz, CHLOROFORM-d, tautomeric mixture (~9/1), main isomer described) δ ppm 1.96 (s, 3H), 2.34 (s, 3H), 3.49 (s, 3H), 7.04 (dt, J=10.0, 8.0 Hz, 1H), 7.19-7.24 (m, 1H), 7.30 (ddd, J=12.0, 8.0, 3.0 Hz, 1H), 7.40 (t, J=5.0 Hz, 1H), 8.41 (br. s., 1H), 8.86 (d, J=5.0 Hz, 2H).

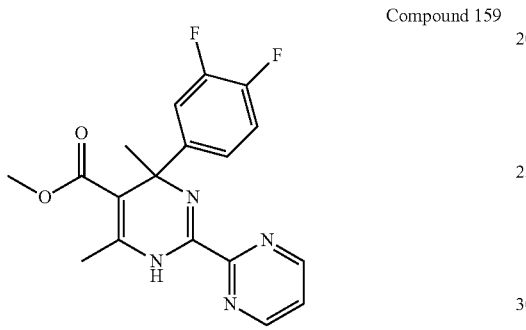

Compound 159

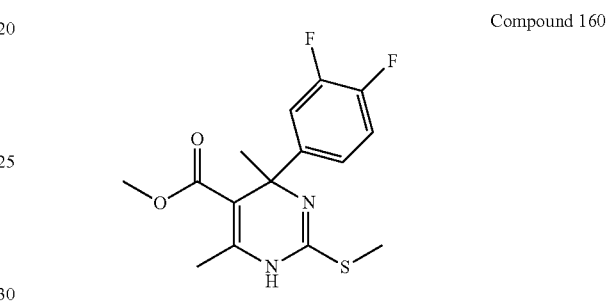

Compound 160

Enantiomers of Racemic Mixture 159: 159a and 159b

A mixture of compound 129 (4 g crude), 2-pyrimidinecarboximidamide (2.35 g, 19.2 mmol) and 1,4-dioxane (25 mL) was stirred at 40° C. for 72 hours and allowed to reach room temperature. The reaction mixture was evaporated to dryness to afford a brown residue. This residue and phosphorus oxychloride (20.9 mL, 225 mmol) were stirred at 120° C. for 45 minutes in a round bottomed flask. The reaction mixture was concentrated in vacuo at 50° C. and co evaporated with toluene (2×100 mL). The residue was dissolved in dichloromethane (250 mL) and washed with saturated aqueous sodium bicarbonate (100 mL), dried (Na$_2$SO$_4$) and evaporated to afford a dark brown residue. This residue was purified using silica gel column chromatography (dichloromethane in heptane from 50 to 100%) to methyl 6-chloro-4-(3,4-difluorophenyl)-4-methyl-2-(pyrimidin-2-yl)-1,4-dihydropyrimidine-5-carboxylate (1800 mg) as light yellow solid. A solution of methyl 6-chloro-4-(3,4-difluorophenyl)-4-methyl-2-(pyrimidin-2-yl)-1,4-dihydropyrimidine-5-carboxylate (900 mg) in 1,4-dioxane (10 mL) in a microwave-vial was stirred and purged with nitrogen for 10 minutes. Then tetramethyltin (494 µL, 3.56 mmol) was added followed by bis(tri-t-butylphosphine) palladium (0) (243 mg, 0.475 mmol) and the vial was flushed with nitrogen and capped. The reaction mixture was heated under microwave irradiation at 140° C. for 30 minutes and allowed to reach room temperature. The reaction mixture was stirred and purged with nitrogen for 10 minutes, bis(tri-t-butylphosphine) palladium (0) (121 mg, 0.238 mmol) was added and the vial was flushed with nitrogen and capped. The reaction mixture was heated by microwave irradiation at 145° C. for 30 minutes and allowed to reach room temperature. The reaction mixture was concentrated in vacuo. The obtained residue was mixed with dichloromethane (100 mL) and the orange precipitate was filtered off. The filtrate was washed with water (2×20 mL), dried (Na$_2$SO$_4$) and con- Enantiomers of 160: 160a and 160b A high pressure tube was charged methyl acetoacetate (54.6 mL, 507 mmol), 3,4-fluorophenylacetylene (70.0 g, 507 mmol) and indium (III) chloride (5.61 g, 25.3 mmol) and closed. The reaction mixture was stirred at 130° C. for 18 hours and next cooled to room temperature. The reaction mixture containing methyl 2-acetyl-3-(3,4-difluorophenyl) but-2-enoate was used as such in the next step. Under an atmosphere of nitrogen, a mixture of S-methylisothiourea hemisulfate (85.2 g, 305.9 mmol), crude methyl 2-acetyl-3-(3,4-difluorophenyl)but-2-enoate (128.9 g), sodium bicarbonate (170.3 g, 2.03 mol) and dry N,N-dimethylformamide (900 mL) was heated at 50° C. for 20 hours. The reaction mixture was cooled to room temperature, purged with nitrogen for 45 minutes and water was added (600 mL). The aqueous mixture was extracted with diethylether (4×300 mL). The combined organic extracts were washed with water (300 mL) and brine (300 mL), dried over Na$_2$SO$_4$ and concentrated under reduced pressure. The residue was co-evaporated using toluene (2×200 mL) resulting in a brown oil. This was dissolved in dichloromethane (150 mL). After 3 hours crystals were collected on a filter and washed with dichloromethane (2×30 mL) to afford compound 160 as white crystals (25.8 g). Method A; Rt: 1.04 m/z; 327.1 (M+H)$^+$ Exact mass: 326.1. $^1$H-NMR (400 MHz, CHLOROFORM-d, containing one drop of TFA) δ ppm 2.04 (s, 3H), 2.31 (s, 3H), 2.65 (s, 3H), 3.54 (s, 3H), 7.10-7.33 (m, 3H). Racemic mixture 160 (20 g) was separated into its enantiomers 160a and 160b by Prep SFC (Stationary phase: Chiralcel Diacel OJ 20×250 mm), Mobile phase: CO$_2$, iPrOH), yielding compound 160a (9.1 g) and 160b (8.6 g after further purification using silica gel column chromatography (ethyl acetate in heptane 15%)). SFC:Column: OJ-H 250 mm×4.6 mm; Flow: 3 mL/min; Mobile phase: 5% iPrOH (containing 0.2% iPrNH$_2$) hold 15.00 min, Temperature: 30° C. Compound 160a: Rt (6.2-7.0 min); Compound 160b: Rt (7.4-8.2 min)

Alternative Synthesis Compound 155b

A microwave vial was charged with compound 160b (200 mg, 0.613 mmol), copper (I) bromide-dimethyl sulfide (504 mg, 2.45 mmol), 2-(tributylstannyl)thiazole (688 mg, 1.8 mmol) and 1,2-dimethoxyethane (6 mL). The reaction mixture was purged with nitrogen and stirred for 10 minutes and palladium(II) acetate (7 mg, 0.0306 mmol) and butyldi-1-adamantylphosphine (22.0 mg, 0.0613 mmol) were added. The vial was flushed with nitrogen and capped. The mixture was stirred and heated by microwave irradiation at 140° C. for 30 minutes. The mixture was diluted with $CH_2Cl_2$ (50 mL) and washed with ammonia (2×50 mL; 25%) and Brine (50 mL). Then it was dried on $Na_2SO_4$, filtered and concentrated under reduced pressure. The residue was purified using silica gel column chromatography (ethyl acetate in heptane 15%) to afford compound 155b as yellow solid. $^1$H NMR ghache__915__1 (400 MHz, DMSO-$d_6$, containing one drop of TFA) δ ppm 1.99 (s, 3H), 2.28 (s, 3H), 3.46 (s, 3H), 7.31-7.51 (m, 2H), 7.58-7.71 (m, 1H), 8.19-8.25 (m, 1H), 8.25-8.34 (m, 1H).

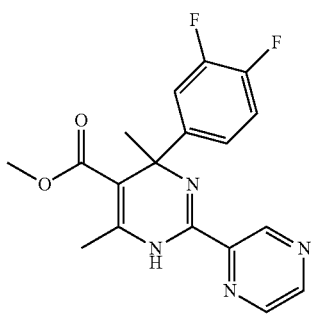

Compound 161

A microwave-vial was charged with 1,2-dimethoxyethane (9 mL), compound 160 (295 mg, 0.9 mmol), 2-(tributylstannyl)pyrazine (854 µL, 2.71 mmol), copper(I) bromide-dimethyl sulfide (743 mg, 3.61 mmol) and this was purged with nitrogen and stirred for 10 minutes. Then palladium(II) acetate (10 mg, 0.045 mmol) and butyldi-1-adamantylphosphine (32 mg, 0.09 mmol) were added and the vial was flushed with nitrogen and capped. This mixture was stirred and heated by microwave-irradiation at 140° C. for 30 minutes. The mixture was diluted with diethylether (100 mL) and washed with ammonia (2×100 m, 25%) and brine (100 mL). Then this was dried on $MgSO_4$, filtered and concentrated under reduced pressure. The obtained residue was purified using reversed phase HPLC (Methanol —$NH_4HCO_3$/column: Hypersil C18 BDS 3 micrometer). The desired fractions were concentrated under reduced pressure and co-evaporated with methanol (2×50 mL). The residue was purified using silica gel column chromatography by gradient elution (heptane-ethylacetate 100:0 to 70:30). The obtained fractions were concentrated under reduced pressure and dried in vacuo at 55° C. yielding compound 161 as a slightly yellow powder (46 mg). Method A; Rt: 1.00 m/z; 359.1 (M+H)$^+$ Exact mass: 358.1.

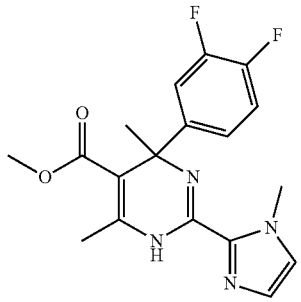

Compound 162

Compound 160 (250 mg, 0.77 mmol), 1-methyl-2-(tributylstannyl)imidazole (0.54 mL, 1.69 mmol) and copper(i) bromide-dimethyl sulfide (346 mg, 1.69 mmol) were added to tetrahydrofuran (12.5 mL) under a nitrogen atmosphere. This solution was stirred at room temperature for 10 minutes and then tetrakis(triphenylphosphine)palladium (44.26 mg, 0.038 mmol) was added. The resulting mixture was refluxed for 24 hours. This mixture was filtered over dicalite and this was rinsed with ethylacetate (50 mL). The residue was concentrated under reduced pressure. The obtained crude was purified using silica gel column chromatography (gradient elution: dichloromethane-methanol: 100:0 to 99:1). The desired fractions were collected and concentrated under reduced pressure yielding a yellow oil. This oil was purified by Prep HPLC on (RP SunFire Prep C18 OBD-10 µm, 30×150 mm). Mobile phase (0.25% $NH_4HCO_3$ solution in water, MeOH). The collected fractions were concentrated under reduced pressure and co-evaporated using methanol (2×20 mL). The obtained residue was dried in vacuo at 55° C. yielding compound 162 as a yellow oil (21 mg). $^1$H NMR (400 MHz, CHLOROFORM-d) δ ppm 1.85 (s, 3H), 2.29 (s, 3H), 3.49 (s, 3H), 3.91 (s, 3H), 6.92 (s, 1H), 7.00 (s, 1H), 7.01-7.10 (m, 1H), 7.12-7.20 (m, 1H), 7.22-7.31 (m, 1H), 7.92 (br. s., 1H).

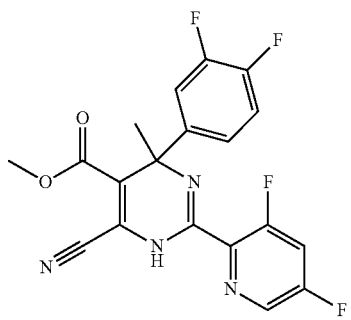 [SMILES: COC(=O)C1=C(C#N)NC(c2ncc(F)cc2F)=NC1(C)c1ccc(F)c(F)c1]

Enantiomers of Racemic Compound 163: 163a, 163b

Compound 131 (500 mg, 1.21 mmol), 1,4-diazabicyclo[2.2.2]octane (0.203 g, 1.81 mmol), tetrabutylammonium cyanide (0.487 g, 1.81 mmol) and dry acetonitrile (10 mL) and molecular sieves were stirred and heated at 100° C. in a closed microwave tube for 90 minutes and allowed to reach room temperature. The reaction mixture was concentrated in vacuo. The residue was dissolved in dichloromethane (50 mL) and washed with water (50 mL). The water layer was extracted with dichloromethane (2×50 mL) and the combined organic layers were washed with brine (50 mL), dried ($Na_2SO_4$), filtered and concentrated in vacuo. The obtained residue was purified using silica gel column chromatography (isocratic dichloromethane). The desired fractions were concentrated in vacuo and further purified by Prep SFC on (Chiralcel Diacel OJ 20×250 mm). Mobile phase (CO$_2$, ethanol with 0.2% isopropyl amine), yielding the separated enantiomers which were further purified using silica gel column chromatography (ethyl acetate in heptane from 0 to 95%) to afford compound 163a (24 mg) and compound 163b (25 mg) as yellow powders which were dried overnight in vacuum oven at 50° C. $^1$H NMR (400 MHz, CHLOROFORM-d containing one drop of TFA) d ppm 2.33 (s, 3H), 3.77 (s, 3H), 7.21-7.33 (m, 2H), 7.39 (ddd, J=10.5, 7.0, 2.0 Hz, 1H), 7.58 (ddd, J=10.5, 7.0, 2.0 Hz, 1H), 8.51 (d, J=2.0 Hz, 1H). Method E; Rt: 1.05 m/z; 405.1 (M+H)$^+$ Exact mass: 404.1. SFC: Columns: OJ-H 250 mm×4.6 mm; Flow: 3 mL/min; Mobile phase: 10% EtOH (containing 0.2% iPrNH$_2$) hold 15.00 min; Temperature: 30° C.; Compound 163a Rt (4.5 min); Compound 163b Rt (5.4 min)

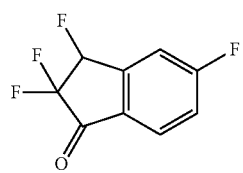

Compound 164

To a mixture of zinc powder (704 mg, 10.8 mmol) in dry THF (50 mL) under nitrogen atmosphere, 1,2 dibromoethane (0.016 mL, 0.181 mmol) followed by trimethylchlorosilane (114 mg, 1.05 mmol) were added. A solution of 2-bromo-5-fluoro-benzaldehyde (2.13 g 10.50 mmol) and ethylbromodifluoroacetate (2.13 g, 10.50 mmol) in THF (25 mL) were added and the reaction mixture was refluxed overnight. The mixture was cooled and poured in ice/water (250 mL). HCl 1M (100 mL) was added while stirring. The mixture was stirred 1 hour and extracted with t-Butylmethylether (200 mL). The organic layer was separated, dried over sodium sulphate, filtered and concentrated. The obtained residue was purified by column chromatography on silica using a gradient from 5 till 100% EtOAc in heptane. The product fractions were combined and concentrated in vacuo yielding ethyl 3-(2-bromo-5-fluorophenyl)-2,2-difluoro-3-hydroxypropanoate (1096 mg). $^1$H NMR (400 MHz, CHLOROFORM-d) δ ppm 1.35 (t, J=7.0 Hz, 3H), 4.37 (q, J=7.0 Hz, 2H), 5.72 (ddd, J=15.7, 6.1, 1.0 Hz, 1H), 6.99 (ddd, J=8.8, 7.7, 3.1 Hz, 1H), 7.39 (ddd, J=9.5, 3.1, 1.0 Hz, 1H), 7.54 (dd, J=8.8, 5.3 Hz, 1H) The procedure was repeated on a larger scale of 2-bromo-5-fluoro-benzaldehyde (71.2 g, 351 mmol) yielding ethyl 3-(2-bromo-5-fluoro-phenyl)-2,2-difluoro-3-hydroxy-propanoate (86 g). DAST (48.3 mL, 394.4 mmol) was added dropwise to a solution of ethyl 3-(2-bromo-5-fluoro-phenyl)-2,2-difluoro-3-hydroxy-propanoate (86 g) in dichloromethane (500 mL) during 15 minutes in an icebath. The reaction mixture was stirred and allowed to reach room temperature overnight. The mixture was slowly added to a vigorously stirred saturated NaHCO$_3$ solution (1.5 L) over 15 minutes. The mixture was stirred for 30 minutes more. The organic layer was dried over magnesium sulphate, filtered and concentrated yielding ethyl 3-(2-bromo-5-fluorophenyl)-2,2,3-trifluoropropanoate (78.0 g) as a light brown oil which was used as such. $^1$H NMR (400 MHz, CHLOROFORM-d) δ ppm 1.38 (t, J=7.2 Hz, 3H), 4.37-4.44 (m, 2H), 6.19-6.41 (m, 1H), 7.01-7.10 (m, 1H), 7.29-7.37 (m, 1H), 7.58 (dd, J=8.9, 5.1, 1.2 Hz, 1H). Ethyl 3-(2-bromo-5-fluoro-phenyl)-2,2,3-trifluoro-propanoate (55.4 g 163.5 mmol), lithium hydroxide (3.92 g, 163.5 mmol), THF (100 mL) and distilled water (200 mL) were stirred 5 minutes at room temperature resulting in a clear solution (1 layer). The reaction mixture was acidified with HCl 1M (164 mL). The resulting emulsion was extracted with CH$_2$Cl$_2$ (500 mL). The organic layer was dried over sodium sulphate, filtered and concentrated yielding a light brown oil (58.7 g). To part of this oil (52.5 g) in dichloromethane (2.6 L) and DMF (7 mmol), oxalylchloride (89.3 g) was added during 15 minutes and the mixture was stirred overnight. The reaction mixture was concentrated, yielding a light brown oil which was used as such. To this oil in dichloromethane (1000 mL), N,O-dimethylhydroxylamine hydrochloride (16.07 g, 149.8 mmol) and sodium carbonate (17.46 g, 164.8 mmol) were added and the mixture was stirred for 90 minutes. Water (500 mL) was added and the mixture was stirred for 5 minutes. The organic layer was separated, dried over MgSO$_4$, filtered and concentrated. The residue was purified by silica gel column chromatography using a gradient from 0 till 10% CH$_3$OH in CH$_2$Cl$_2$. The product fractions were combined and concentrated resulting in 3-(2-bromo-5-fluorophenyl)-2,2,3-trifluoro-N-methoxy-N-methylpropanamide (37.1 g). $^1$H NMR (400 MHz, CHLOROFORM-d) δ ppm 3.32 (s, 3H), 3.82 (s, 3H), 6.41-6.64 (m, 1H), 7.01-7.07 (m, 1H), 7.34-7.41 (m, 1H), 7.56 (ddd, J=8.9, 5.2, 1.1 Hz, 1H). Buthyllithium (49.5 mL, 1.6M in hexanes) was added during 30 minutes at −70° C. to a solution of 3-(2-bromo-5-fluoro-phenyl)-2,2,3-trifluoro-N-methoxy-N-methylpropanamide (25.9 g, 75.4 mmol) in dry THF (225 mL). The mixture was stirred 30 minutes and then allowed to reach room temperature during 90 minutes. The reaction mixture was quenched with HCl (1M, 100 mL) and diluted with diisopropylether (250 mL). The water layer was extracted twice with CH$_2$Cl$_2$ (250 mL). The combined organic layers were dried over sodium sulphate, filtered and concentrated. The residue was purified by column chromatography on silica using a gradient from 5 till 100% EtOAc in heptane. The product fractions were concentrated yielding compound 164 (12.6 g) as an oil. Method L; Rt: 1.69 m/z; 202.8 (M−H)$^−$ Exact mass: 204.0. $^1$H NMR (400 MHz, CHLOROFORM-d) δ ppm 5.80-6.01 (m, 1H), 7.42 (tt, J=8.6, 1.8 Hz, 1H), 7.47-7.54 (m, 1H), 8.00 (ddd, J=8.6, 5.1, 1.3 Hz, 1H).

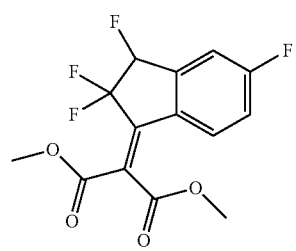

Compound 165

Titaniumtetrachloride (16.29 mL) dissolved in CH$_2$Cl$_2$ (25 mL) was added dropwise, over 10 minutes, to a solution of compound 164 (2,2,3,5-tetrafluoroindan-1-one; 12.6 g, 61.5 mmol) and dimethylmalonate (12.2 g, 92.3 mmol) in dry THF (100 mL) and dichloromethane (100 mL) in an icebath. The reaction mixture was stirred 10 minutes Then pyridine (21.8 mL) was added during 5 minutes and the reaction mixture was allowed to reach room temperature overnight with stirring. The reaction mixture was quenched with water (400 mL) and diluted with CH$_2$Cl$_2$ (500 mL). The organic layer was separated, dried over magnesium sulphate, filtered and concentrated. The residue was purified by column chromatography on silica with a gradient from 10 till 100% EtOAc in heptane.

The pure product fractions were combined and concentrated resulting in compound 165 (21.0 g, containing 28% w/w dimethylmalonate) Method L; Rt: 1.86 m/z; 318.9 (M+H)+ Exact mass: 318.1. ¹H NMR (400 MHz, CHLOROFORM-d) δ ppm 3.90 (s, 3H), 3.91 (s, 3H), 5.75 (ddd, J=53.9, 10.6, 2.9 Hz, 1H), 7.18-7.26 (m, 1H), 7.30 (dt, J=7.5, 2.0 Hz, 1H), 7.87 (ddd, J=8.9, 4.9, 1.4 Hz, 1H.

Compound 166

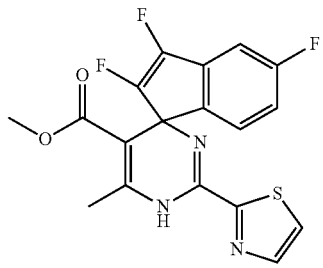

Enantiomers of Racemic Compound 166: 166a and 166b

Compound 165 (5.0 g, 11.3 mmol), 2-thiazolecarboxamidine hydrochloride (2.78 g; 17.0 mmol), sodium bicarbonate (3.33 g) in dioxane (100 mL) were stirred overnight at 50° C. The reaction mixture was next stirred 2 hours at 60° C., 2 hours at 70° C. and 4 hours at 80° C., each time adding more thiazolecarboxamidine (500 mg). The mixture was next cooled, filtered and concentrated. The residue was purified by silica gel column chromatography using a gradient from 10 till 100% EtOAc in heptane. The product fractions were collected and concentrated yielding a light yellow sticky oil containing methyl 2,2,3,5-tetrafluoro-6'-oxo-2'-(thiazol-2-yl)-2,3,5',6'-tetrahydro-1'H-spiro[indene-1,4'-pyrimidine]-5'-carboxylate (2.33 g). This oily residue (2.33 g) was stirred in POCl₃ (10 mL) at 120° C. during 5 hours. The reaction mixture was concentrated. The obtained residue was dissolved in CH₂Cl₂ (100 mL) and poured in saturated NaHCO₃ solution (200 mL). This mixture was stirred vigorously during 15 minutes. The organic layer was separated, dried over magnesium sulphate, filtered and concentrated. The obtained residue was purified by silica gel column chromatography using a gradient from 10 till 100% EtOAc in heptanes. The product fractions were concentrated in vacuo yielding methyl 6'-chloro-2,2,3,5-tetrafluoro-2'-(thiazol-2-yl)-2,3-dihydro-1'H-spiro[indene-1,4'-pyrimidine]-5'-carboxylate as a yellow powder. (799 mg). Method L; Rt: 1.89 and 1.99 (4/6 ratio) m/z; 431.9 (M+H)+ Exact mass: 431.0. Nitrogen was bubbled through a solution of methyl 6'-chloro-2,2,3,5-tetrafluoro-2'-(thiazol-2-yl)-2,3-dihydro-1'H-spiro[indene-1,4'-pyrimidine]-5'-carboxylate (799 mg) in DMF (7 mL). Then tetramethyltin (331 mg, 1.85 mmol) and bis(tri-tert-butylphosphine)palladium (0) (95 mg, 0.185 mmol) were added and the reaction mixture heated in a Biotage microwave at 140° C. during 1 hour. The mixture was filtered and concentrated in vacuo. The residue was purified by silica gel column chromatography using a gradient from 10 till 100% EtOAc in heptane. The product fractions were concentrated and dried in vacuo yielding methyl 2,2,3,5-tetrafluoro-6'-methyl-2'-(thiazol-2-yl)-2,3-dihydro-1'H-spiro[indene-1,4'-pyrimidine]-5'-carboxylate as a light yellow resin (577 mg). Method L; Rt: 1.91 m/z; 412.3 (M+H)+ Exact mass: 411.1. Nitrogen was bubbled through methyl 2,2,3,5-tetrafluoro-6'-methyl-2'-(thiazol-2-yl)-2,3-dihydro-1'H-spiro[indene-1,4'-pyrimidine]-5'-carboxylate (565 mg) dissolved in dry THF (50 mL) during 10 minutes. potassium bis(trimethylsilyl)amide (11 mL; 0.5 M toluene, 5.5 mmol) was added and the reaction mixture stirred under a nitrogen flow during 30 minutes. The mixture was quenched with water (10 mL) and partially concentrated. The remainder was extracted with CH₂Cl₂ (50 mL) and water (30 mL). The organic layer was dried over magnesium sulphate, filtered and concentrated. The residue was purified by column chromatography on silica using a gradient from 10 till 100% EtOAc in heptane. The product fractions were combined, concentrated, and the obtained residue dried in vacuo at 50° C., resulting in compound 166 a as a yellow powder (272 mg). Method L; Rt: 2.10 m/z; 392.3 (M+H)+ Exact mass: 391.1. ¹H NMR (400 MHz, CHLOROFORM-d) δ ppm 2.44 (s, 3H), 3.40 (s, 3H), 6.86 (ddd, J=10.0, 8.0, 2.5 Hz, 1H), 7.00 (dd, J=8.0, 2.5 Hz, 1H), 7.15 (ddd, J=8.0, 5.0, 2.5 Hz, 1H), 7.48 (d, J=3.0 Hz, 1H), 7.85 (d, J=3.0 Hz, 1H), 8.01 (br. s., 1H). The racemic mixture 166 was separated in enantiomers by Prep SFC (Stationary phase:Chiralcel Diacel OD 20×250 mm), Mobile phase: CO₂, Isopropanol), the desired fractions were collected, evaporated, dissolved in MeOH and evaporated again resulting in compound 166a (103 mg) and compound 166b (96 mg) as yellow oils. Column: OD-H 250 mm×4.6 mm; Flow: 3 mL/min; Mobile phase: 5% iPrOH (containing 0.2% iPrNH₂) hold 15.00 min; Temperature: 30° C.; Compound 166a Rt (9.9 min) Compound 166b Rt (11.0 min).

Compound 167

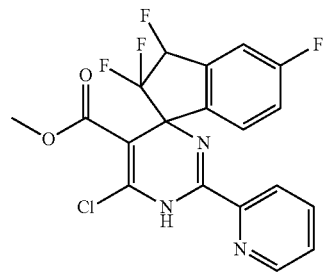

Separated Diastereoisomers of Diastereoisomeric Mixture 167: 167a and 167B

Compound 165 (10.2 g, 23.1 mmol), pyridine-2-carboximidamide hydrochloride (6.37 g, 40.4 mmol), sodium bicarbonate (7.76 g, 92.4 mmol) and dioxane (200 mL) were heated and stirred at 60° C. during 6 hours and stirred further overnight at 40° C. The reaction mixture was filtered and concentrated. The residue was purified by column chromatography on silica using a gradient from 5 till 100% EtOAc in heptane. The product fractions were combined and concentrated yielding methyl 2,2,3,5-tetrafluoro-6'-oxo-2'-(pyridin-2-yl)-2,3,5',6'-tetrahydro-1'H-spiro[indene-1,4'-pyrimidine]-5'-carboxylate (6.1 g) as a light yellow amorphous powder. A solution of methyl 2',2',3',5'-tetrafluoro-6-oxo-2-(2-pyridyl)spiro[1,5-dihydropyrimidine-4,1'-indane]-5-carboxylate in phosphorus oxychloride (50 g) equipped with a CaCl₂ drying tube was heated at 110° C. during 210 minutes. The reaction mixture was concentrated, the residue dissolved in CH₂Cl₂ (200 mL), poured in saturated NaHCO₃ (200 mL) solution and stirred 30 minutes. The organic layer was dried over sodium sulphate, filtered and concentrated. The residue was purified by column chromatography on silica using a gradient from 5 till 100% EtOAc in heptane. methyl 6'-chloro-2,2,3,5-tetrafluoro-2'-(pyridin-2-yl)-2,3-dihydro-1'H-spiro[indene-1,4'-pyrimidine]-5'-carboxylate was isolated as two separate diastereoisomers: and compound 167A (1046 mg after second purification) and compound 167B (1705 mg).

Compound 167A: Method L; Rt: 1.94 m/z; 425.9 (M+H)+ Exact mass: 425.1.

Compound 167B: Method L; Rt: 2.06 m/z; 425.9 (M+H)+ Exact mass: 425.1.

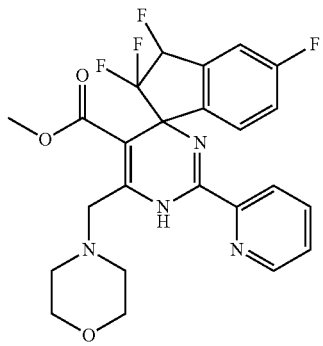

Compound 168

Separated Diastereoisomers of Diastereoisomeric Mixture 168: 168a and 168B

Nitrogen was flushed through a mixture of compound 167B (1705 mg) potassium (morpholin-4-yl)methyltrifluoroborate (1658 mg, 8.0 mmol), potassium carbonate (1384 mg, 10 mmol) in ethylene glycol dimethylether (5 mL) and water (2.3 mL) during 10 minutes. Then bis(tri-tert-butylphosphine)palladium (0) (1614 mg, 20 mmol) was added and the reaction mixture heated at 140° C. during 45 minutes in a Biotage microwave. The mixture was concentrated and the residue taken up in water (50 mL) and CH₂Cl₂ (50 mL). The organic layer was dried over MgSO₄, filtered and concentrated. The residue was purified by column chromatography on silica a using a gradient from 10 till 100% EtOAc in heptane. The product fractions were concentrated and dried in vacuo yielding compound 168B (923 mg) as a yellow powder. Method L; Rt: 2.07 m/z; 491.1 (M+H)+ Exact mass: 490.2. $^1$H NMR (400 MHz, CHLOROFORM-d) δ ppm 2.51-2.73 (m, 4H), 3.43 (s, 3H), 3.71-3.93 (m, 6H), 5.96 (ddd, J=55.0, 10.1, 3.7 Hz, 1H), 7.05-7.24 (m, 3H), 7.41 (ddd, J=8.0, 4.8, 1.3 Hz, 1H), 7.75 (td, J=8.0, 1.8 Hz, 1H), 8.23 (dt, J=8.0, 1.1 Hz, 1H), 8.56-8.68 (m, 1H), 10.55 (s, 1H). Compound 167A was converted to Compound 168A similarly as described for compound 168B, resulting in Compound 168A (470 mg) as a yellow solid. Method L; Rt: 2.08 m/z; 491.1 (M+H)+ Exact mass: 490.2. $^1$H NMR (400 MHz, CHLOROFORM-d) δ ppm 2.61-2.68 (m, 4H), 3.39 (s, 3H), 3.77-3.92 (m, 6H), 6.12 (dt, J=54.6, 8.1 Hz, 1H), 7.06-7.14 (m, 1H), 7.15-7.24 (m, 2H), 7.39 (ddd, J=7.6, 4.8, 1.2 Hz, 1H), 7.73 (td, J=7.8, 1.7 Hz, 1H), 8.07 (dt, J=8.0, 1.1 Hz, 1H), 8.57-8.65 (m, 1H), 10.50 (s, 1H).

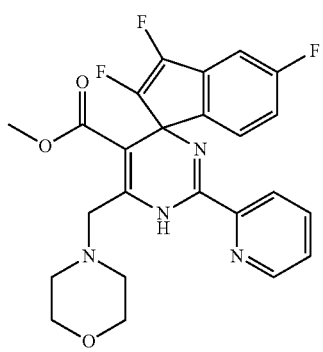

Compound 169

Lithium bis(trimethylsilyl)amide (4.0 mL, 1M THF) was added to a solution of compound 168A (0.811 mmol, 398 mg) in dry THF (50 mL) and stirred 30 minutes at room temperature. The reaction mixture was quenched with water (30 mL) and extracted twice with CH₂Cl₂ (50 mL). The organic layer was dried over magnesium sulphate, filtered and concentrated. The residue was purified by column chromatography on silica using a gradient from 10 till 100% EtOAc. The product fractions were combined and concentrated in vacuo at 50° C. yielding compound 169 as a yellow powder (329 mg). Method L; Rt: 2.16 m/z; 471.1 (M+H)+ Exact mass: 470.2. $^1$H NMR (400 MHz, CHLOROFORM-d) δ ppm 2.55-2.71 (m, 4H), 3.40 (s, 3H), 3.78-3.92 (m, 6H), 6.84 (ddd, J=9.7, 8.1, 2.4 Hz, 1H), 7.00 (dd, J=8.4, 2.4 Hz, 1H), 7.11 (ddd, J=8.1, 4.8, 2.1 Hz, 1H), 7.39 (ddd, J=7.5, 4.8, 1.1 Hz, 1H), 7.74 (td, J=7.8, 1.7 Hz, 1H), 8.15 (dt, J=8.0, 0.9 Hz, 1H), 8.56-8.66 (m, 1H), 10.47 (s, 1H). Compound 169 can be prepared starting from compound 168B in a similar way as described from 168A.

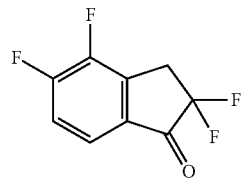

Compound 170

TFA (4.6 mL, 59.8 mmol) was added to a solution of 4,5-difluoro-1-indanone (50.3 g, 299.2 mmol) and butylamine (26.3 g, 359 mmol) in cyclohexane (500 mL) and the mixture was refluxed overnight in a Dean Stark apparatus. The reaction mixture was concentrated and the residue dissolved in diisopropylether (300 mL). The solution was washed with saturated NaHCO₃ solution, dried over magnesium sulphate, filtered and concentrated yielding a dark red liquid that solidified on standing. This obtained crude (61.4 g) was used as such. N-butyl-4,5-difluoro-indan-1-imine (28.2 g, part of the above crude mixture) was dissolved in dry acetonitrile (500 mL) sodium sulfate (8.46 g, 59.6 mmol) was added followed by 1-chloromethyl-4-fluoro-1,4-diazoniabicyclo[2.2.2]octane bis(tetrafluoroborate) (60.1 g, 169.7 mmol). The reaction mixture was refluxed and stirred during 3 hours. The reaction mixture was allowed to cool 5 minutes, then HCl 37% (45 mL) was added portionwise while stirring. The mixture was stirred 10 minutes and then concentrated in vacuo. The obtained residue was extracted with diisopropylether (800 mL) overnight, decanted, filtered and concentrated. The residue was suspended in water and extracted with diisopropylether (500 mL). The combined organic layers were dried over magnesium sulphate, filtered and concentrated. The residue was purified by column chromatography on silica gel using gradient elution from 5 till 100% EtOAc in heptane. The product fractions were combined and concentrated in vacuo yielding compound 170 (6.98 g). $^1$H NMR (400 MHz, CHLOROFORM-d) δ ppm 3.61 (t, J=12.3 Hz, 2H), 7.28-7.40 (m, 1H), 7.65-7.76 (m, 1H).

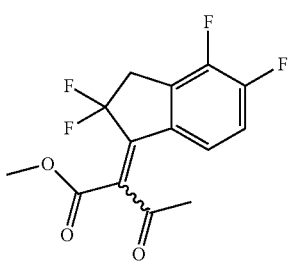

Compound 171

Titanium tetrachloride (7.94 g, 68.4 mmol) dissolved in CH$_2$Cl$_2$ (25 mL) was added dropwise during 10 minutes to a solution of 2,2,4,5-tetrafluoroindan-1-one (11 mL, 99 mmol) and methyl acetoacetate (6.98 g, 34.2 mmol) in THF (150 mL) and dichloromethane (150 mL) in an icebath. The reaction mixture was stirred 10 minutes. Then pyridine (13.5 mL, 167.5 mmol) was added over 5 minutes. The reaction mixture was allowed to reach room temperature while stirring and was further stirred during 5 days. The reaction mixture was quenched with water (100 mL) and extracted with dichloromethane (200 mL). The organic layer was dried over magnesium sulphate, filtered and concentrated. The residue was purified by column chromatography on silica using a gradient from 5 till 100% EtOAc. The product fractions were concentrated resulting in compound 171a brown resin (E/Z mixture, 6.17 g). $^1$H NMR (400 MHz, CHLOROFORM-d) E/Z or Z/E mixture 85/15, main isomer described: 6 ppm 2.50 (s, 3H), 3.55 (t, J=13.2 Hz, 2H), 3.89 (s, 3H), 7.04-7.19 (m, 1H), 7.26-7.31 (m, 1H).

Nitrogen was bubbled through a mixture of compound 172 (2.83 g, 7.56 mmol) 2-(tributylstannyl)thiazole (8.5 g 22.8 mmol), copper(I) bromide-dimethyl sulfide (6.2 g 30.24 mmol) in DME (25 mL) during 10 minutes divided in 3 microwave vials). (bis(tri-tert-butylphosphine)palladium(0) (290 mg, 0.257 mmol) was added and the reaction mixture was irradiated in the microwave at 140° C. during 30 minutes. The mixtures were poured in ammonia in water (500 mL, 25%) and extracted 3 times with ether (250 mL). The organic layer was dried over sodium sulphate, filtered and concentrated. The residue was subjected to column chromatography on silica using a gradient from 10 till 100% EtOAc in heptane. The product fractions were concentrated in vacuo yielding a yellow solid (127 mg). Method L; Rt: 2.03 m/z; 412.3 (M+H)$^+$ Exact mass: 411.1. $^1$H NMR (400 MHz, CHLOROFORM-d); tautomeric mixture (~8/2), main isomer described; 6 ppm 2.41 (s, 3H), 3.44 (s, 3H), 3.52-3.78 (m, 2H), 6.88 (dd, 1H, J=4.2, 8.6 Hz), 7.01-7.17 (m, 1H), 7.47 (d, J=3.1 Hz, 1H), 7.84 (d, J=3.1 Hz, 1H), 8.03 (br. s., 1H).

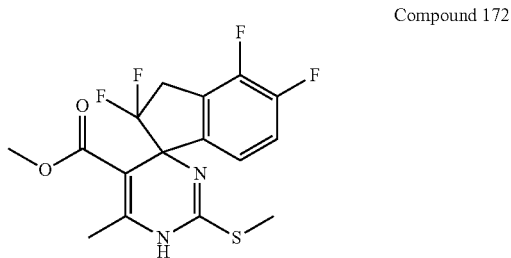 [SMILES: COC(=O)C1=C(C)NC(SC)=NC12c1ccc(F)c(F)c1CC2(F)F]

Compound 172

Compound 171 (5.86 g, 19.39 mmol), 2-methyl-2-thiopseudourea sulfate (4.05 g 14.5 mmol) and sodium bicarbonate (6.0 g, 116.3 mmol) in DMF (100 mL) were stirred at 50° C. overnight. The reaction mixture was poured in water (800 mL) and extracted 3 times with diethylether (400 mL). The water layer was extracted also twice with dichloromethane (500 mL). Both organic layers were washed with water, dried over sodium sulphate, filtered and concentrated together. The residue was purified by silica gel column chromatography using a gradient from 10 till 100% EtOAc in heptane. The product fractions were combined and concentrated in vacuo yielding compound 172 as a brown solid (5.89 g). Method L; Rt: 1.97 m/z; 375.3 (M+H)$^+$ Exact mass: 374.1. $^1$H NMR (400 MHz, CHLOROFORM-d, −4° C.): ~4/1 tautomeric mixture, main isomer described: ppm 2.27 (s, 3H), 2.33 (s, 3H), 3.43 (s, 3H), 3.54 (dd, J=17.3, 9.3 Hz, 2H), 6.71 (br. s, 1H), 6.84 (dd, J=8.3, 4.0 Hz, 1H), 7.02-7.11 (m, 1H).

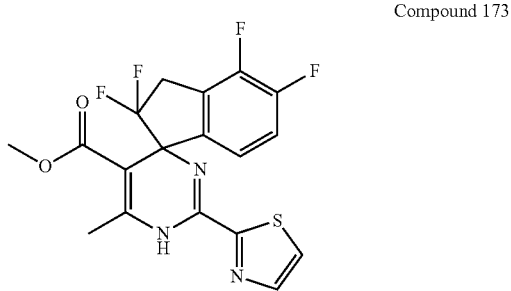 [SMILES: COC(=O)C1=C(C)NC(c2nccs2)=NC12c1ccc(F)c(F)c1CC2(F)F]

Compound 173

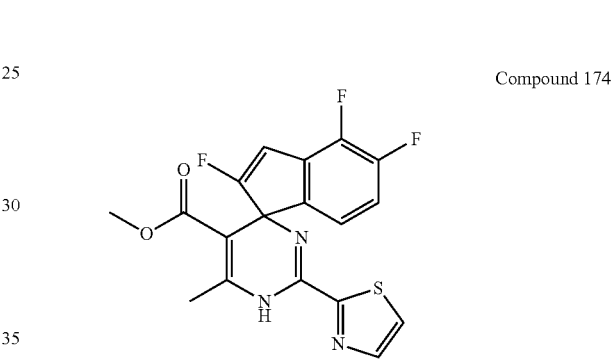

Compound 174

Enantiomers of Racemic Compound 174: 174a and 174b (1.11 g, 2.7 mmol), sodium methylate (874 mg, 16.2 mmol) in methanol (7 mL) was heated in a Biotage microwave at 140° C. during 10 minutes. The reaction mixture was concentrated and the residue dissolved in CH$_2$Cl$_2$ (50 mL) and water (50 mL). The water layer was extracted again with CH$_2$Cl$_2$ (50 mL). The combined organic layers were dried over magnesium sulphate, filtered and concentrated. The residue was purified by column chromatography on a silica using a gradient from 10 till 100% EtOAc in heptane. The product fractions were concentrated and dried yielding a yellow powder. (778 mg) Method L; Rt: 1.93 m/z; 392.2 (M+H)$^+$ Exact mass: 391.1

$^1$H NMR (400 MHz, CHLOROFORM-d) δ ppm 2.44 (s, 3H), 3.43 (s, 3H), 6.09 (s, 1H), 6.78-6.93 (m, 2H), 7.47 (d, J=3.3 Hz, 1H), 7.84 (d, J=3.3 Hz, 1H), 7.98 (br. s., 1H). Compound 174 (205 mg) was separated in enantiomers by Prep SFC (Stationary phase: Chiralcel Diacel ID 20×250 mm), Mobile phase: CO$_2$, EtOH with 0.2% iPrNH$_2$), the desired fractions were collected, concentrated in vacuo, dissolved in MeOH, evaporated again and dried overnight in vacuo at 50° C., resulting in compound 174a (68 mg) and compound 174b (74 mg). SFC: Column: ID-H 250 mm×4.6 mm; Flow: 3 mL/min; Mobile phase: 5% EtOH (containing 0.2% iPrNH$_2$) hold 15.00 min Temperature: 30° C.; compound 174a Rt (~6.2 min); compound 174b Rt (~7.0 min)

Compound 175 (One Main Diastereoisomer as Depicted, Racemic Mixture)

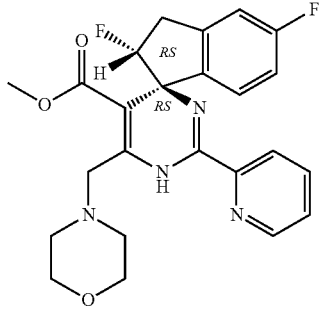 [SMILES: COC(=O)C1=C(CN2CCOCC2)NC(c2ccccn2)=N[C@@]12c1ccc(F)cc1C[C@H]2F]

A mixture of compound 169 (840 mg, 1.79 mmol) and Pd/C 10% (203 mg) in methanol (200 mL) was stirred for 3 hours under hydrogen atmosphere and left over weekend without stirring. The reaction mixture was stirred for 45 minutes more and the mixture was filtered. $K_2CO_3$ (1 g) was added to the filtrate and then concentrated. The obtained residue was dissolved in $CH_2Cl_2$ (100 mL) and water (50 mL). The organic layer was separated, dried over magnesium sulphate, filtered and concentrated. The residue was purified by silica gel column chromatography using gradient elution with 5 to 100% EtOAc in heptane. The product fractions were combined, concentrated and dried yielding compound 175 (75 mg) as a light yellow powder. Method L; Rt: 2.04 m/z; 455.1 $(M+H)^+$ Exact mass: 454.2. $^1H$ NMR (600 MHz, ACETONE-$d_6$) δ ppm 2.53-2.66 (m, 4H), 3.22 (ddd, J=25.7, 17.2, 4.4 Hz, 1H), 3.39 (s, 3H), 3.53 (td, J=16.0, 7.7 Hz, 1H), 3.72 (s, 2H), 3.73-3.80 (m, 4H), 5.15 (ddd, J=53.6, 7.5, 4.7 Hz, 1H), 6.93 (ddd, J=9.2, 8.5, 2.5 Hz, 1H), 6.99 (m, J=9.2 Hz, 1H), 7.16 (dd, J=8.4, 5.3 Hz, 1H), 7.55 (ddd, J=7.5, 4.8, 1.2 Hz, 1H), 7.90 (td, J=7.7, 1.7 Hz, 1H), 8.11 (d, J=7.9 Hz, 1H), 8.71 (ddd, J=4.8, 1.6, 0.9 Hz, 1H), 10.14 (br. s., 1H).

Biological Examples

Anti-HBV Activity of Compounds of Formula I

The anti-HBV activity was measured using a stable transfected cell line, HepG2.2.15. This cell line was described to secrete relatively consistent high levels of HBV virion particles, which have been shown to cause both acute and chronic infection and disease in chimpanzees.

For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

Cytotoxicity of the compounds was tested in HepG2 cells using CellTiter-Blue, with the same incubation period and dose range as in the HepG2.2.15 assay. Results are displayed in Table 1.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1

| anti-HBV activity of compounds of formula I | | | | | |
|---|---|---|---|---|---|
| STRUCTURE | Compound nr. | HBV-HepG2 2.15 6 days EC50 (μM) | HepG2 6 days CC50 (μM) | HepG2 117 EC50 (μM) | HepG2 4 days CC50 (μM) |
| 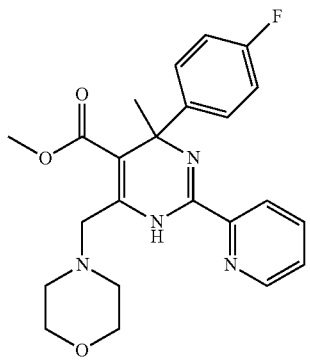 [SMILES: COC(=O)C1=C(CN2CCOCC2)NC(c2ccccn2)=NC1(C)c1ccc(F)cc1] | 2 | 0.669 | >100 | 0.25 | >50 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 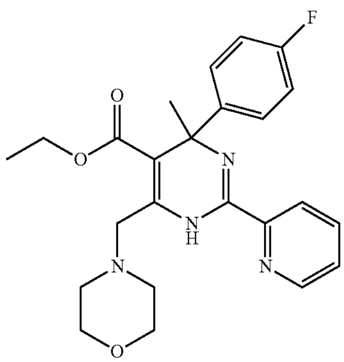 [SMILES: CCOC(=O)C1=C(CN2CCOCC2)NC(c2ccccn2)=NC1(C)c1ccc(F)cc1] | 4 | 1.92 | 51.1 | 0.66 | >25 |
| | 4a | >100 | 92.0 | | |
| | 4b | 0.643 | 92.4 | 0.76 | >50 |
| 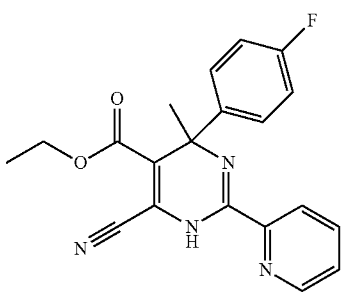 [SMILES: CCOC(=O)C1=C(C#N)NC(c2ccccn2)=NC1(C)c1ccc(F)cc1] | 5 | >100 | >100 | | |
| 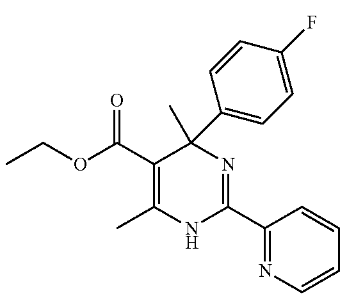 [SMILES: CCOC(=O)C1=C(C)NC(c2ccccn2)=NC1(C)c1ccc(F)cc1] | 6 | >25 | >25 | | |
| 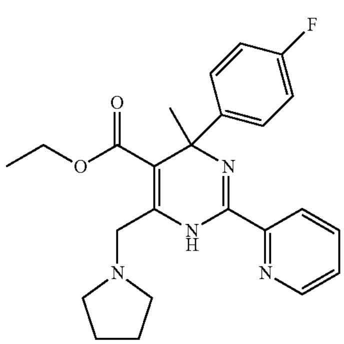 [SMILES: CCOC(=O)C1=C(CN2CCCC2)NC(c2ccccn2)=NC1(C)c1ccc(F)cc1] | 7 | >100 | 13.4 | | |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 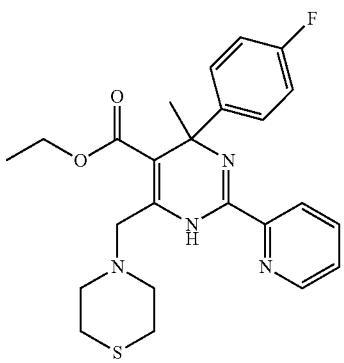 [SMILES: CCOC(=O)C1=C(CN2CCSCC2)NC(c2ccccn2)=NC1(C)c1ccc(F)cc1] | 8 | 14.8 | 54.3 | 3.3 | >50 |
| 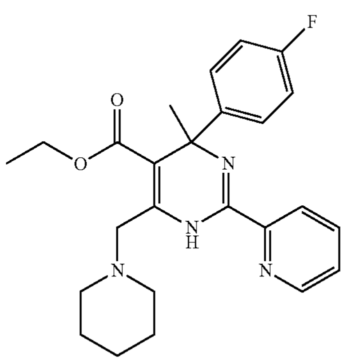 [SMILES: CCOC(=O)C1=C(CN2CCCCC2)NC(c2ccccn2)=NC1(C)c1ccc(F)cc1] | 9 | >100 | 62.4 | | |
| 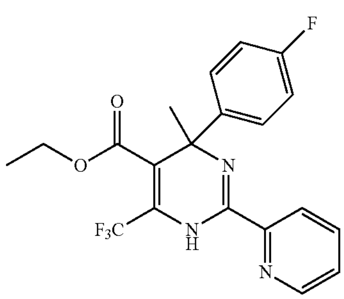 [SMILES: CCOC(=O)C1=C(C(F)(F)F)NC(c2ccccn2)=NC1(C)c1ccc(F)cc1] | 10 | >10 | >10 | >10 | >10 |
| 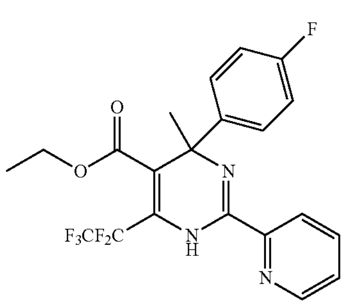 | 11 | >100 | >100 | | |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 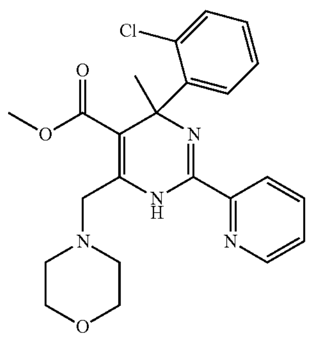 [SMILES: COC(=O)C1=C(CN2CCOCC2)NC(c2ccccn2)=NC1(C)c1ccccc1Cl] | 13 | 9.34 | >100 | 3.9 | >100 |
| 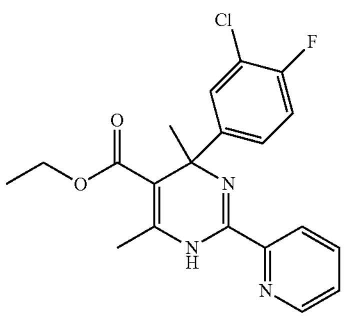 [SMILES: CCOC(=O)C1=C(C)NC(c2ccccn2)=NC1(C)c1ccc(F)c(Cl)c1] | 17 | >50 | 39.9 | 21.0 | >25 |
| 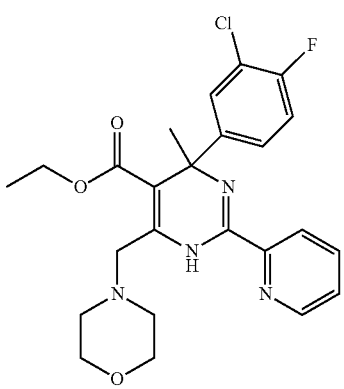 [SMILES: CCOC(=O)C1=C(CN2CCOCC2)NC(c2ccccn2)=NC1(C)c1ccc(F)c(Cl)c1] | 18 | 3.92 | 36.5 | 1.6 | >50 |
| 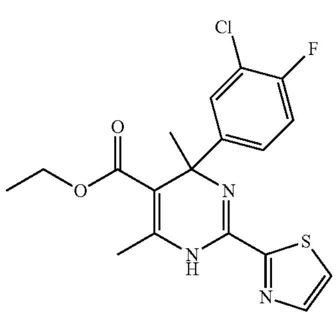 [SMILES: CCOC(=O)C1=C(C)NC(c2nccs2)=NC1(C)c1ccc(F)c(Cl)c1] | 21 | 12.7 | 17.5 | | |

TABLE 1-continued
anti-HBV activity of compounds of formula I
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 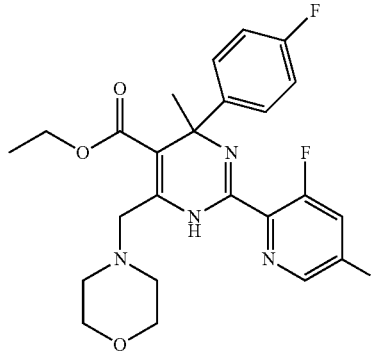 | 24 | 0.319 | 37.9 | 0.16 | >25 |
| 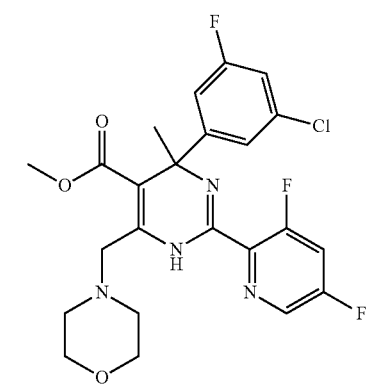 [SMILES: COC(=O)C1=C(CN2CCOCC2)NC(c2ncc(F)cc2F)=NC1(C)c1cc(F)cc(Cl)c1] | 27 | 1.83 | >100 | 0.63 | >25 |
| 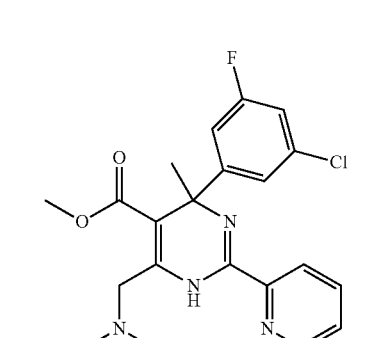 | 29 | 6.32 | 47.4 | 3.0 | >25 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 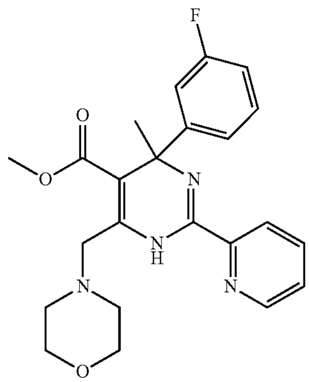 [SMILES: COC(=O)C1=C(CN2CCOCC2)NC(c2ccccn2)=NC1(C)c1cccc(F)c1] | 30 | 0.941 | >100 | 0.29 | >25 |
| 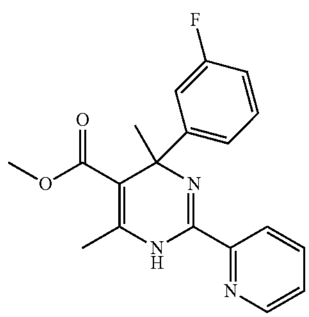 [SMILES: COC(=O)C1=C(C)NC(c2ccccn2)=NC1(C)c1cccc(F)c1] | 31 | 72.4 | >100 | 40.6 | >50 |
| 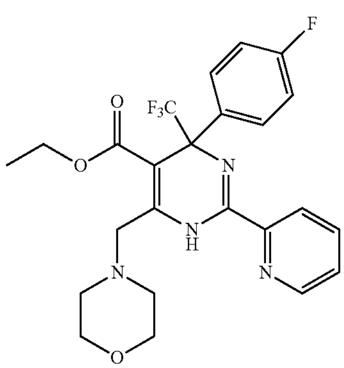 [SMILES: CCOC(=O)C1=C(CN2CCOCC2)NC(c2ccccn2)=NC1(c1ccc(F)cc1)C(F)(F)F] | 34 | 16.2 | 20 | | |
| | 34a | >100 | 30.9 | | |
| | 34b | 8.23 | 41.6 | | |
| 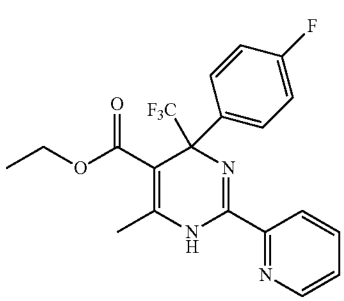 | 35 | >100 | 68.1 | | |

TABLE 1-continued

| anti-HBV activity of compounds of formula I | | | | | |
|---|---|---|---|---|---|
| STRUCTURE | Compound nr. | HBV-HepG2 2.15 6 days EC50 (μM) | HepG2 6 days CC50 (μM) | HepG2 117 4 days EC50 (μM) | HepG2 4 days CC50 (μM) |
| | 39 | 0.405 | 62.9 | 0.41 | >100 |
| | 40 | 14.0 | 77.0 | | |
| | 41 | 7.39 | >50 | 4.5 | >25 |
| | 42 | 3.07 | 57.7 | 1.29 | >50 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 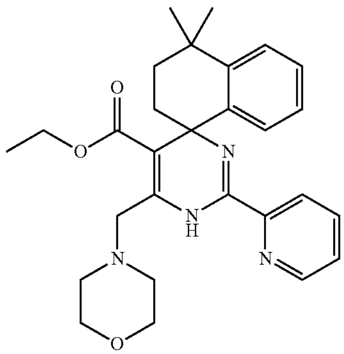 [SMILES: CCOC(=O)C1=C(CN2CCOCC2)NC(c2ccccn2)=NC12CCC(C)(C)c1ccccc12] | 56 | 35.2 | 36.4 | 52.6 | >100 |
| 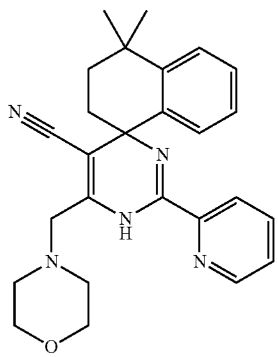 [SMILES: CC1(C)CCC2(N=C(c3ccccn3)NC(CN3CCOCC3)=C2C#N)c2ccccc21] | 57 | >100 | 87.4 | >25 | >25 |
| 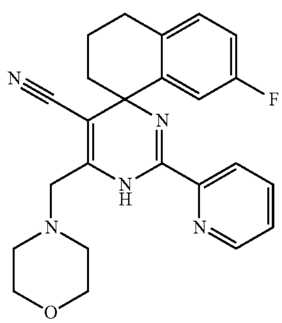 [SMILES: N#CC1=C(CN2CCOCC2)NC(c2ccccn2)=NC12CCCc1ccc(F)cc12] | 58 | >100 | >100 | >25 | >25 |
| 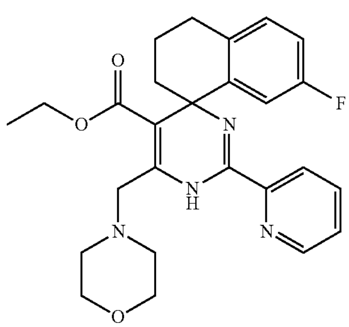 [SMILES: CCOC(=O)C1=C(CN2CCOCC2)NC(c2ccccn2)=NC12CCCc1ccc(F)cc12] | 59 | 59.5 | 68.9 | 46.7 | >100 |

TABLE 1-continued
anti-HBV activity of compounds of formula I
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 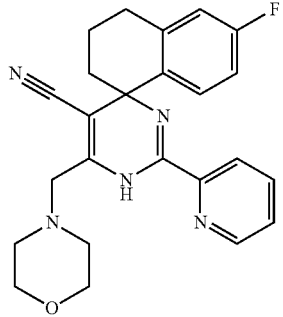 [SMILES: N#CC1=C(CN2CCOCC2)NC(c2ccccn2)=NC12CCCc1cc(F)ccc12] | 60 | 2.83 | >100 | 2.5 | >25 |
|  | 60a | >100 | >100 | >100 | >100 |
|  | 60b | 2.26 | >100 | 1.28 | >100 |
| 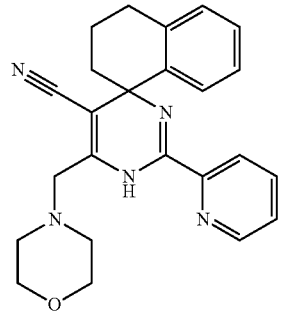 [SMILES: N#CC1=C(CN2CCOCC2)NC(c2ccccn2)=NC12CCCc1ccccc12] | 61 | 18.0 | >100 | | |
| 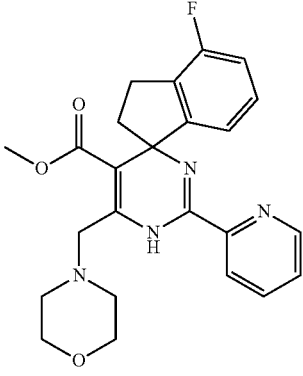 [SMILES: COC(=O)C1=C(CN2CCOCC2)NC(c2ccccn2)=NC12CCc1c(F)cccc12] | 66 | 0.207 | 89.3 | 0.17 | >25 |
|  | 66a | <0.391 | >100 | 0.066 | >100 |
|  | 66b | 35.1 | >100 | 48.9 | >100 |

TABLE 1-continued
anti-HBV activity of compounds of formula I
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 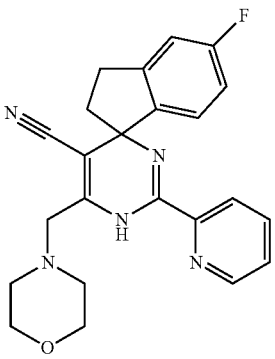 [SMILES: N#CC1=C(CN2CCOCC2)NC(c2ccccn2)=NC12CCc1cc(F)ccc12] | 69 | 2.21 | >100 | 1.65 | >100 |
| 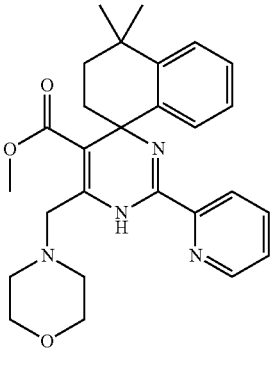 [SMILES: COC(=O)C1=C(CN2CCOCC2)NC(c2ccccn2)=NC12CCC(C)(C)c1ccccc12] | 72 | 54.0 | 71.1 | 72.0 | >100 |
| 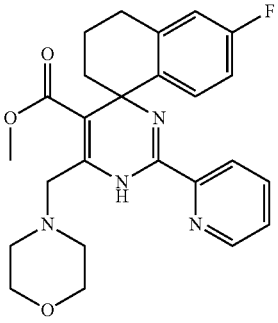 [SMILES: COC(=O)C1=C(CN2CCOCC2)NC(c2ccccn2)=NC12CCCc1cc(F)ccc12] | 74 | 2.06 | 78.3 | 1.33 | >100 |
| 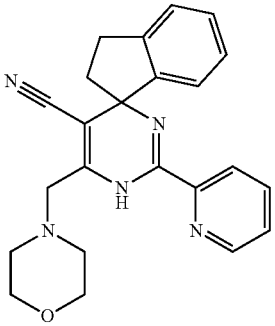 [SMILES: N#CC1=C(CN2CCOCC2)NC(c2ccccn2)=NC12CCc1ccccc12] | 76 | 8.48 | >100 | 3.65 | >100 |

TABLE 1-continued
anti-HBV activity of compounds of formula I
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 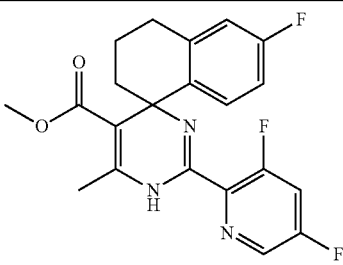 | 80 | | 51.1 | 25.1 | >50 |
| 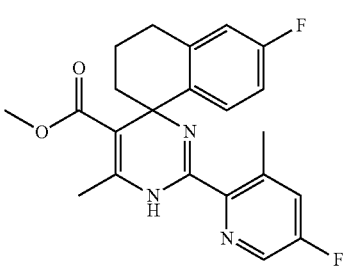 [SMILES: COC(=O)C1=C(C)NC(c2ncc(F)cc2C)=NC12CCCc1cc(F)ccc12] | 81 | 19.9 | >50 | | |
| 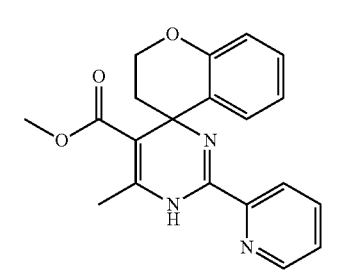 [SMILES: COC(=O)C1=C(C)NC(c2ccccn2)=NC12CCOc1ccccc12] | 85 | >100 | >100 | >50 | >50 |
| 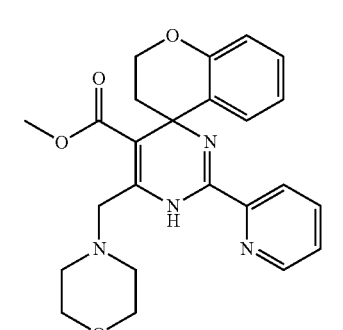 | 86 | 8.64 | >100 | 5.49 | >100 |
| 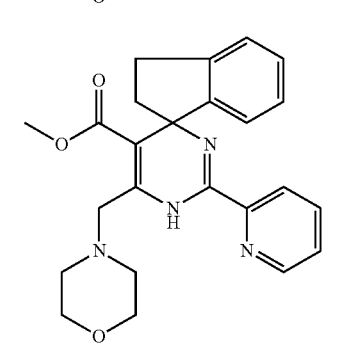 | 89 | 0.604 | >100 | 0.470 | >100 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 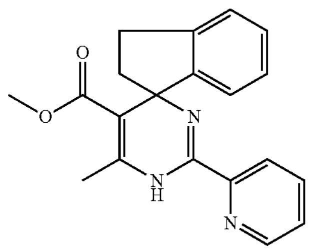 [SMILES: COC(=O)C1=C(C)NC(c2ccccn2)=NC12CCc1ccccc12] | 90 | 5.82 | >50 | 22.7 | >50 |
| 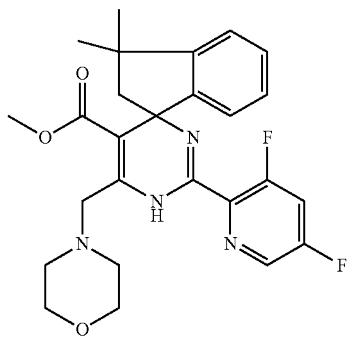 [SMILES: COC(=O)C1=C(CN2CCOCC2)NC(c2ncc(F)cc2F)=NC12CC(C)(C)c1ccccc12] | 93 | 53.4 | 41.5 | 81.2 | >100 |
| 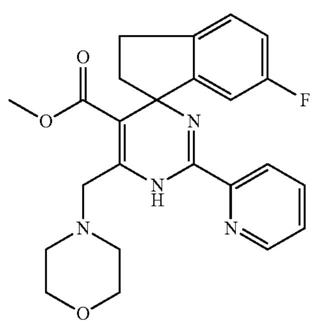 [SMILES: COC(=O)C1=C(CN2CCOCC2)NC(c2ccccn2)=NC12CCc1ccc(F)cc12] | 96 | 0.954 | >100 | 0.94 | 97.0 |
| | 96a | 0.650 | >100 | 0.30 | >100 |
| | 96b | 30.3 | >100 | 18.7 | >100 |
| 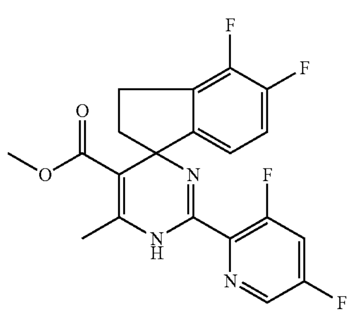 [SMILES: COC(=O)C1=C(C)NC(c2ncc(F)cc2F)=NC12CCc1c2ccc(F)c1F] | 100 | 0.546 | >100 | 0.506 | >100 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 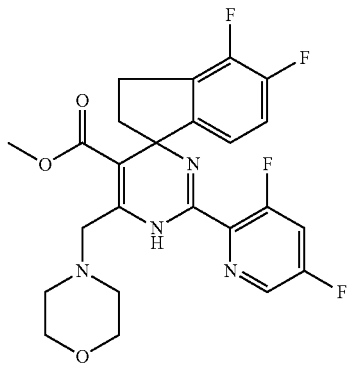 [SMILES: COC(=O)C1=C(CN2CCOCC2)NC(c2ncc(F)cc2F)=NC12CCc1c2ccc(F)c1F] | 101 | <0.098 | >25 | 0.073 | >50 |
| 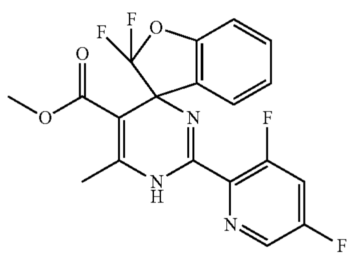 [SMILES: COC(=O)C1=C(C)NC(c2ncc(F)cc2F)=NC12c1ccccc1OC2(F)F] | 106 | 98.4 | >100 | >25 | >25 |
| | 106a | >100 | >100 | >50 | >50 |
| | 106b | 29.4 | >100 | >25 | >25 |
| 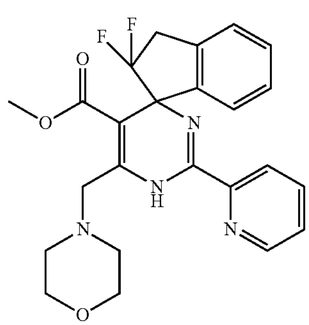 [SMILES: COC(=O)C1=C(CN2CCOCC2)NC(c2ccccn2)=NC12c1ccccc1CC2(F)F] | 110 | 10.7 | >100 | 6.14 | >50 |
| 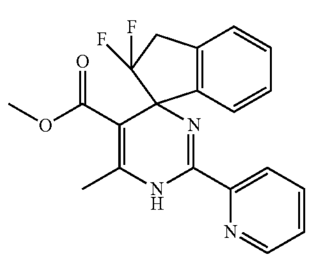 [SMILES: COC(=O)C1=C(C)NC(c2ccccn2)=NC12c1ccccc1CC2(F)F] | 111 | 81.8 | >100 | >50 | >50 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 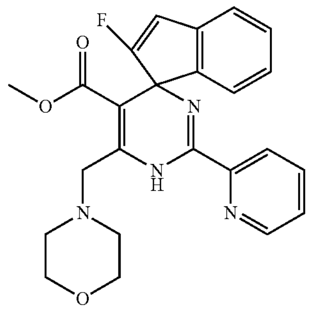 [SMILES: COC(=O)C1=C(CN2CCOCC2)NC(c2ccccn2)=NC12C(F)=Cc1ccccc12] | 112 | 0.624 | >100 | 0.410 | >50 |
| 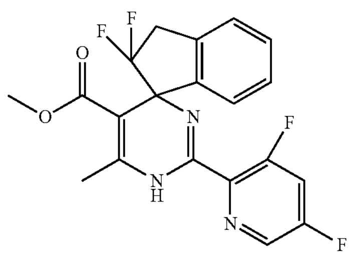 [SMILES: COC(=O)C1=C(C)NC(c2ncc(F)cc2F)=NC12c1ccccc1CC2(F)F] | 115 | >100 | >100 | >25 | >25 |
| 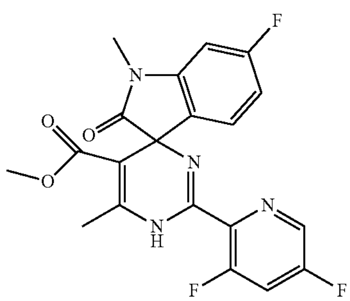 [SMILES: COC(=O)C1=C(C)NC(c2ncc(F)cc2F)=NC12C(=O)N(C)c1cc(F)ccc12] | 118 | 40.7 | >100 | >50 | >50 |
| 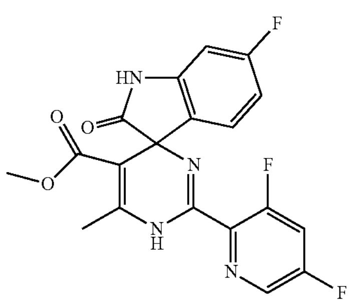 [SMILES: COC(=O)C1=C(C)NC(c2ncc(F)cc2F)=NC12C(=O)Nc1cc(F)ccc12] | 123 | >100 | | >25 | >25 |
| 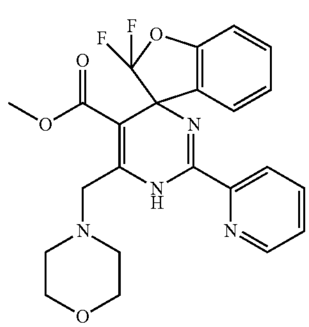 | 124 | 13.0 | 48.4 | 2.41 | >25 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| (structure) | 128 | 9.10 | 63.8 | 2.47 | >50 |
| (structure) | 132 | 2.03 | | 0.88 | >25 |
| | 132a | >100 | | >25 | 21.1 |
| | 132b | 0.784 | | 0.474 | >25 |
| | 132b •MsOH | 0.694 | | 0.803 | >25 |
| | 132b (−)-camphanic acid | 0.489 | | | |
| (structure) | 133 | 17.3 | | 4.33 | >25 |
| (structure) | 134 | | | | |
| | 134a | 91.2 | 53.0 | >50 | >50 |
| | 134b | 41.9 | 35.8 | >50 | >50 |

TABLE 1-continued

| | anti-HBV activity of compounds of formula I | | | | |
|---|---|---|---|---|---|
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
| | 139 •TFA | 0.99 | | 0.707 | >25 |
| | 142 | 11.5 | | 3.37 | >25 |
| | 143 | | | 0.222 | >25 |
| | 144 | | | 4.94 | >10 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 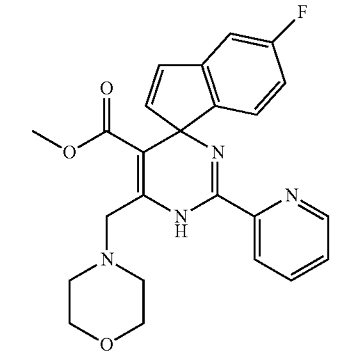 [SMILES: COC(=O)C1=C(CN2CCOCC2)NC(c2ccccn2)=NC12C=Cc1cc(F)ccc12] | 145 | 0.360 |  | 0.620 | >25 |
| 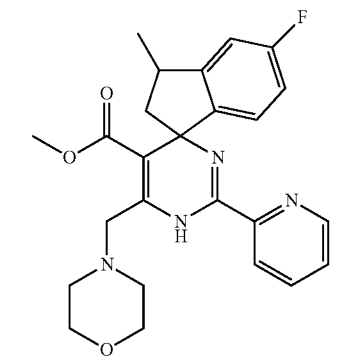 [SMILES: COC(=O)C1=C(CN2CCOCC2)NC(c2ccccn2)=NC12CC(C)c1cc(F)ccc12] | 146 | 1.36 |  | 2.62 | >25 |
| 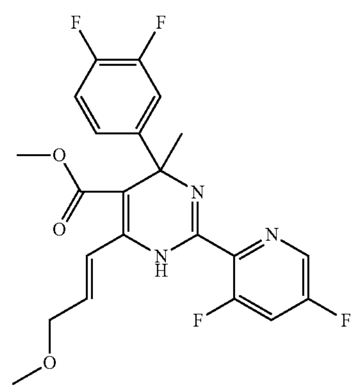 [SMILES: COC/C=C/C1=C(C(=O)OC)C(C)(c2ccc(F)c(F)c2)N=C(c2ncc(F)cc2F)N1] | 147 | 2.73 |  | 3.17 | >25 |
| 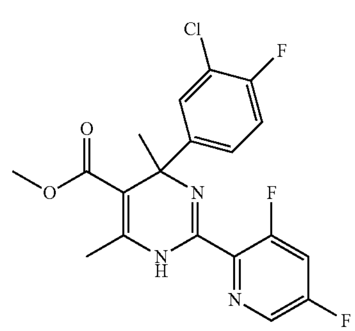 | 148 |  | >25 |  | 17.2 |

TABLE 1-continued
anti-HBV activity of compounds of formula I
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 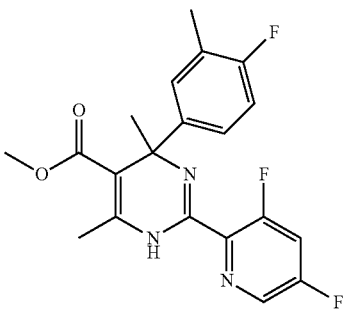 [SMILES: COC(=O)C1=C(C)NC(c2ncc(F)cc2F)=NC1(C)c1ccc(F)c(C)c1] | 149 | 23.8 | | 3.26 | >25 |
| 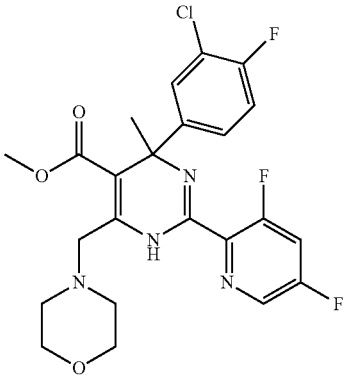 [SMILES: COC(=O)C1=C(CN2CCOCC2)NC(c2ncc(F)cc2F)=NC1(C)c1ccc(F)c(Cl)c1] | 150 | 1.35 | | 0.694 | >25 |
| 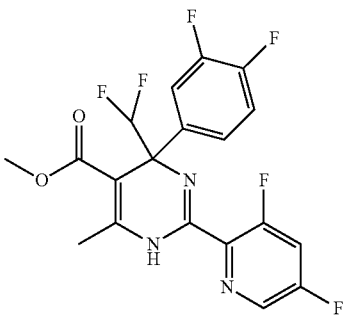 [SMILES: COC(=O)C1=C(C)NC(c2ncc(F)cc2F)=NC1(c1ccc(F)c(F)c1)C(F)F] | 151 | | | | |
| | 151a | >100 | | >25 | >25 |
| | 151b | 4.25 | | 3.68 | >25 |
| 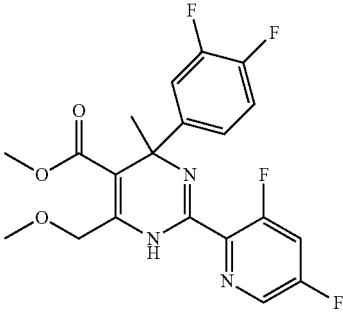 [SMILES: COCC1=C(C(=O)OC)C(C)(c2ccc(F)c(F)c2)N=C(c2ncc(F)cc2F)N1] | 152 | 3.38 | | 2.88 | >25 |

TABLE 1-continued

| | anti-HBV activity of compounds of formula I | | | |
|---|---|---|---|---|
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
| | 153 | 12.9 | | 3.31 | >25 |
| | 154 | 27.5 | | 17.6 | >25 |
| | 155 | 0.744 | | 14.0 | >25 |
| | 155a | 0.983 | | 17.1 | >25 |
| | 155b | >100 | | >25 | >25 |
| | 156 | 1.11 | | 0.669 | >25 |
| | 156·MsOH | 1.93 | | 1.09 | >25 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| (structure) | 157 | 9.52 | | 3.06 | >25 |
| (structure) | 158 | | | 4.56 | >25 |
| | 158a | | | 2.44 | >25 |
| | 158b | >100 | | >25 | >25 |
| (structure) | 159 | | | | |
| | 159a | 37.5 | | 25.0 | >25 |
| | 159b | >100 | | >25 | >25 |
| (structure) | 160 | 0.717 | | 23.7 | >25 |
| | 160a | >50 | | >25 | >25 |
| | 160b | 0.451 | | 10.5 | >25 |

TABLE 1-continued
anti-HBV activity of compounds of formula I
| STRUCTURE | Compound nr. | HBV-HepG2 2.15 EC50 (μM) | HepG2 6 days CC50 (μM) | HepG2 117 EC50 (μM) | HepG2 4 days CC50 (μM) |
| --- | --- | --- | --- | --- | --- |
| 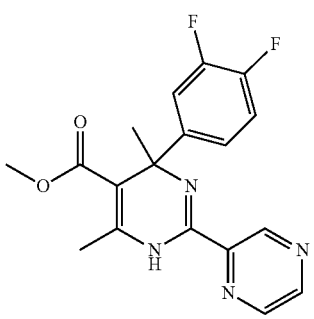 [SMILES: COC(=O)C1=C(C)NC(c2cnccn2)=NC1(C)c1ccc(F)c(F)c1] | 161 | | | >25 | |
| 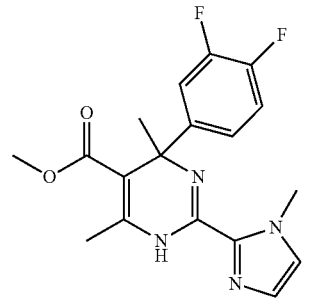 [SMILES: COC(=O)C1=C(C)NC(c2nccn2C)=NC1(C)c1ccc(F)c(F)c1] | 162 | >25 | | >25 | >25 |
| 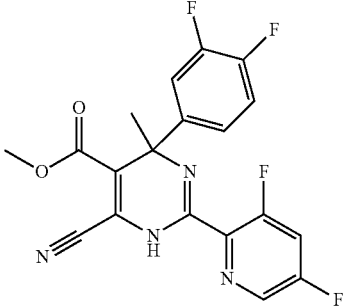 [SMILES: COC(=O)C1=C(C#N)NC(c2ncc(F)cc2F)=NC1(C)c1ccc(F)c(F)c1] | 163 | | | | |
| | 163a | 69.5 | | >25 | >25 |
| | 163b | >100 | | >25 | >25 |
| 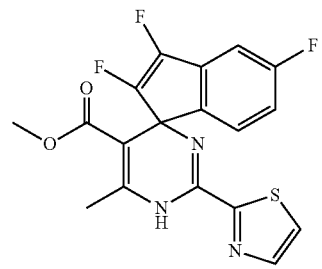 [SMILES: COC(=O)C1=C(C)NC(c2nccs2)=NC12C(F)=C(F)c1cc(F)ccc12] | 166 | 0.24 | | 14.2 | >25 |
| | 166a | >50 | | >25 | >25 |
| | 166b | 0.197 | | 15.5 | >25 |

TABLE 1-continued anti-HBV activity of compounds of formula I

| STRUCTURE | Compound nr. | HBV-HepG2 2.15 EC50 (μM) | HepG2 6 days CC50 (μM) | HepG2 117 EC50 (μM) | HepG2 4 days CC50 (μM) |
|---|---|---|---|---|---|
| 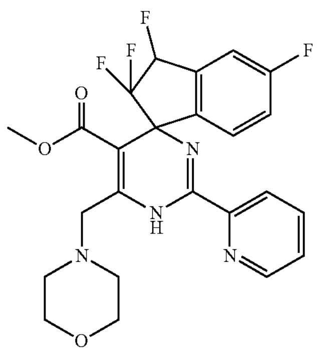 [SMILES: COC(=O)C1=C(CN2CCOCC2)NC(c2ccccn2)=NC12c1ccc(F)cc1C(F)C2(F)F] | 168 | | | | |
| | 168A | 9.64 | | 3.51 | >25 |
| | 168B | 5.73 | | 1.49 | >25 |
| 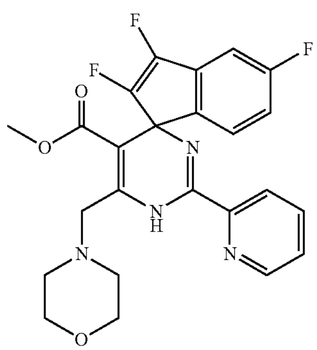 [SMILES: COC(=O)C1=C(CN2CCOCC2)NC(c2ccccn2)=NC12C(F)=C(F)c1cc(F)ccc12] | 169 | | | 0.137 | >25 |
| 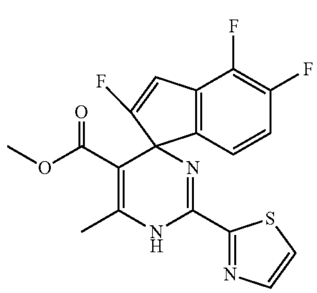 [SMILES: COC(=O)C1=C(C)NC(c2nccs2)=NC12C(F)=Cc1c2ccc(F)c1F] | 174 | | | 13.4 | >25 |
| | 174a | | | 8.97 | >25 |
| | 174b | | | >25 | >25 |
| 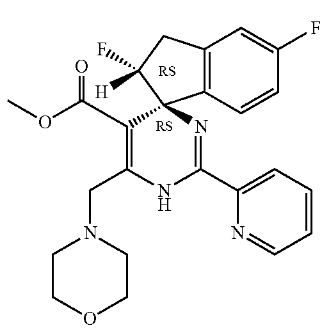 [SMILES: COC(=O)C1=C(CN2CCOCC2)NC(c2ccccn2)=N[C@@]12c1ccc(F)cc1C[C@H]2F] | 175 | <0.195 | | 0.146 | >25 |

The invention claimed is:

1. A compound of Formula I

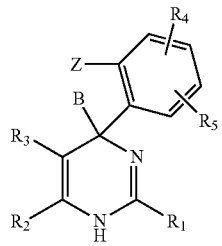

(I)

including any possible stereoisomers or tautomeric forms thereof, wherein:

B is selected from the group consisting of $C_1$-$C_3$ alkyl and $C_1$-$C_3$ alkyl substituted with one or more Fluoro atoms;

Z is selected from H or halogen;

Or B and Z together with the carbons to which they are attached form a 4-7 membered ring, optionally containing one or more heteroatoms, wherein the 4-7 membered ring optionally is substituted with one or more substituents selected from the group consisting of $C_1$-$C_3$ alkyl, oxo, OH and halogen;

$R_1$ is selected from the group comprising heteroaryl and phenyl, optionally substituted with one or more substituents selected from the group consisting of halogen and $C_1$-$C_3$ alkyl;

$R_2$ is selected from the group consisting of —$R_6$-$R_7$, C≡N, cyclopropyl and $CF_3$;

$R_3$ is selected from the group consisting of $C_1$-$C_3$alkoxycarbonyl and C≡N;

$R_4$ and $R_5$ independently are selected from the group consisting of H, methyl and halogen;

$R_6$ is $C_1$-$C_3$ alkyl or $C_2$-$C_3$alkenyl, both optionally substituted with one or more Fluoro;

$R_7$ is selected from the group consisting of hydrogen, a hetero $C_{3-7}$cycloalkyl, cyclopropyl, $C_1$-$C_3$alkoxy and $CF_3$;

or a pharmaceutically acceptable salt or a solvate thereof.

2. A compound according to claim 1 wherein B is selected from the group consisting of $C_1$-$C_3$ alkyl optionally substituted with one or more Fluoro atoms;

Z is selected from H or halogen;

Or B and Z together with the carbons to which they are attached form a 4-7 membered ring, optionally containing one or more heteroatoms, wherein the 4-7 membered ring optionally is substituted with one or more substituents selected from the group consisting of $C_1$-$C_3$ alkyl oxo and halogen; and $R_1$ is selected from the group consisting of heteroaryl and phenyl, optionally substituted with one or more halogen atoms.

3. A compound according to claim 1, wherein B and Z together with the carbons to which they are attached form a 5- or 6-membered ring, optionally substituted with one or more substituents selected from the group consisting of $C_1$-$C_3$ alkyl, oxo and halogen.

4. A compound according to claim 1, wherein B and Z together with the carbons to which they are attached form a 5- or 6-membered ring, optionally substituted with one or more $CH_3$ substituents.

5. A compound according to claim 1, wherein $R_1$ is selected from pyridinyl optionally substituted with one ore two Fluoro, or thiazolyl.

6. A compound according to claim 1, wherein $R_3$ is $C_1$- or $C_2$-alkyloxycarbonyl.

7. A compound according to claim 1, wherein $R_6$ is $CH_2$ and $R_7$ is selected from morpholinyl or piperidinyl.

8. The compound according to claim 1, wherein formula I is formula (Ia)

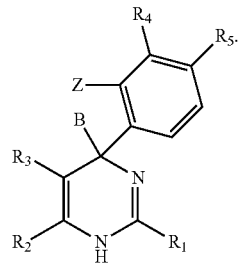

9. A compound according to claim 1 wherein $R_4$ and $R_5$ independently are selected from the group H and Fluoro.

10. A pharmaceutical composition comprising a compound according to claim 1, and a pharmaceutically acceptable carrier.

11. A product containing (a) a compound of claim 1, and (b) another HBV inhibitor, as a combined preparation for simultaneous, separate or sequential use in the treatment of HBV infections.

12. The compound according to claim 1, wherein $R_2$ is Cl.

13. A method of treating an HBV infection in a mammal, comprising administering to said mammal the compound of claim 1.

* * * * *